US008076469B2

(12) United States Patent
Andersen et al.

(10) Patent No.: US 8,076,469 B2
(45) Date of Patent: Dec. 13, 2011

(54) **TB DIAGNOSTIC BASED ON ANTIGENS FROM *M. TUBERCULOSIS***

(75) Inventors: Peter Andersen, Bronshoj (DK); Karin Weldingh, Vaerlose (DK); Christina Veggerby Hansen, Manchester (GB); Walter Florio, Carrara (IT); Li Mei Meng Okkels, Bagsværd (DK); Rikke Louise Vinther Skjot, Hedehusene (DK); Peter Birk Rasmussen, Frederiksberg (DK)

(73) Assignee: Statens Serum Institut, Copenhagen (DK)

( * ) Notice: Subject to any disclaimer, the term of this patent is extended or adjusted under 35 U.S.C. 154(b) by 461 days.

(21) Appl. No.: 11/934,048

(22) Filed: Nov. 1, 2007

(65) Prior Publication Data

US 2008/0267990 A1    Oct. 30, 2008

Related U.S. Application Data

(60) Continuation of application No. 11/196,018, filed on Aug. 2, 2005, now abandoned, which is a division of application No. 10/138,473, filed on May 2, 2002, now Pat. No. 6,982,085, which is a continuation-in-part of application No. 10/060,428, filed on Jan. 29, 2002, now abandoned, which is a continuation-in-part of application No. 09/415,884, filed on Oct. 8, 1999, now abandoned.

(60) Provisional application No. 60/116,673, filed on Jan. 21, 1999.

(30) Foreign Application Priority Data

| Apr. 2, 1997 | (DK) | 1997 00376 |
| Nov. 10, 1997 | (DK) | 1997 01277 |
| Oct. 8, 1998 | (DK) | 1998 01281 |

(51) Int. Cl.
C07H 21/04    (2006.01)
C07H 21/02    (2006.01)
A61K 39/04    (2006.01)

(52) U.S. Cl. .................... 536/23.7; 536/23.1; 424/248.1; 530/300; 530/350

(58) Field of Classification Search ................ 536/23.1, 536/23.7; 424/248.1; 530/300, 350
See application file for complete search history.

(56) References Cited

U.S. PATENT DOCUMENTS

| 4,891,315 | A | 1/1990 | Watson |
| 4,952,395 | A | 8/1990 | Shinnick |
| 4,976,395 | A | 12/1990 | von Kozierowski |
| 5,026,546 | A | 6/1991 | Hilgers |
| 5,330,754 | A | 7/1994 | Kapoor |
| 5,559,011 | A | 9/1996 | Kapoor |

FOREIGN PATENT DOCUMENTS

| WO | WO 92/14823 | 9/1992 |
| WO | WO-95/01441 | 1/1995 |
| WO | WO 95/14713 | 6/1995 |
| WO | WO-96/37219 | 11/1996 |
| WO | WO-97/09428 | 3/1997 |
| WO | WO-97/09429 | 3/1997 |
| WO | WO-98/16645 | 4/1998 |
| WO | WO-98/16646 | 4/1998 |
| WO | WO 98/44119 | 10/1998 |
| WO | WO 98/53075 | 11/1998 |
| WO | WO 98/53076 | 11/1998 |

OTHER PUBLICATIONS

Infection and Immunity 62(6) Jun. 1994 p. 2536-2544, Andersen, P "Effective vaccination of mice against *Mycobacterium tuberculosis* infection . . . . "
Journal of Immunological Methods 161(1993) p. 29-39, Andersen, P et al. "Simultaneous electroelution of whole SDS-Polyacrylamide gels for the . . . . "
The Journal of Immunology 154(1995) p. 3359-3372, Andersen, P et al. "Recall of long-lived immunity to *Mycobacterium tuberculosis* infection in mice".
J. Mol. Biol. 215(1990) p. 403-410, Altschul, S et al. "Basic local alignment search tool".
Infection and Immunity 66(5) Jun. 1998 p. 2951-2959, Baldwin, S et al. "Evaluation of new vaccines in the mouse and guinea pig model . . . . "
Infection and Immunity 63(4) Apr. 1995 p. 1491-1497, Boesen, H et al "Huamn t-cell responses to secreted antigen fractions . . . . "
J. Exp. Med. 178 (Dec. 1993) p. 2243-2247 Cooper A et al. "Disseminated tuberculosis in interferon . . . . "
Immunology and Cell Biology 75(1997) p. 595-603 Elhay, M et al. "Immunological requirements for a subunit vaccine . . . . "
The Journal of Immunology 138 (Jun. 15, 1987) p. 4408-4413 Flesch, I et al. "Mycobacterial growth inhibition by interferon . . . . "
J. Exp. Med. 178 (Dec. 1993)p. 2249-2254 Flynn, J et al. "An essential role for interferon . . . . "
Proc. Natl. Acad. Sci. USA 92 (Feb. 1995) p. 1530-1534 Horwitz, M et al. "Protective immunity against tuberculosis induced . . . . "
Advances in Applied Mathematics 12 (1991) p. 337-357 Huang, X et al. "A time-efficient, linear-space local similarity algorithm".
Tetrahedron 54 (1998) p. 3607-3630 Koshkin, A et al. "LNA(Locked Nucleic Acids): Synthesis of the adenine, cytosine, guanine, 5-methylcytosine . . . . "
Immunology 25 (1973) p. 703-715 Lefford, M et al. "Properties of lymphocytes which confer adoptive immunity to tuberculosis in rats".
J. Am. Chem. Soc. 120(22) 1998 p. 5458-5463 Christensen, N et al. "A novel class of olionucleotide analogues containing . . . . "
Science 254 (Dec. 1991) p. 1497-1500 Nielsen, P et al. "Sequence-selective recognition of DNA by strand displacement . . . . "
Infection and Immunity 56(12) Dec. 1988, p. 3310-3312 Orme, I "Induction of nonspecific acquired resistance and delayed-type . . . . "
The Journal of Immunology 140(10) May 15, 1988 p. 3589-3593 Orme, I "Characteristics and specificity of acquired immunologic memory . . . . "

(Continued)

*Primary Examiner* — Rodney P. Swartz
(74) *Attorney, Agent, or Firm* — Birch, Stewart, Kolasch and Birch, LLP

(57) ABSTRACT

The present invention is based on the identification and characterization of a number of novel *M. tuberculosis* derived proteins and protein fragments. The invention is directed to the polypeptides and immunologically active fragments thereof, the genes encoding them, immunological compositions such as diagnostic reagents containing the polypeptides.

37 Claims, No Drawings

OTHER PUBLICATIONS

The Journal of Infectious Diseases 167(1993) p. 1481-1497 Orme, I et al. "T cell rsponse to *Mycobacterium tuberculosis*".
Infection and Immunity 60(11) Nov. 1992 p. 4781-4792 Pal, P et al. "Immunization with extracellular proteins . . . ."
Proc. Natl. Acad. Sci. USA 85(Apr. 1988)p. 2444-2448 Pearson, W et al. "Improved tools for biological sequence comparison".
The Journal of Infectious Diseases 179(3) Mar. 1999 Ravn, P et al. "Human T cell responses to ESAT-6 antigen . . . ."
Res. Microbiol. 5th Forum in Microbiology, 141(1990) p. 253-256 Rook, G "The role of activated macrophages in protection and . . . ."
Synthetic Oligonucleotide Probes 1989 p. 11.45-11.49 Sambrook et al. "Conditions for hybridization of oligonucleotide probes".
Clin. Infect. Dis. 25(Sep. 1997) p. 617-620 Sodhi, A et al. "Clinical correlates of interferon . . . ."
Nature 393(Jun. 11, 1998) 537-44 [erratum: 396(Nov. 12, 1998) 190-98] Cole et al "Deciphering the biology of *Mycobacterium tuberculosis* from . . . ."
Molecular Microbiology 7(2)(1993) 197-206 Eiglmeier et al "Use of an ordered cosmid library to deduce the genomic organization of *Mycobacterium leprae*".
Ploug, Michael et al.; "Determination of Amino.." Analytical Biochemistry 181, 33-39 (1989).
Ohara, N. et al.; "Characterization of the Gene.." Scand J. Immunol. 41, 433-442, 1995.
Oettinger, Thomas et al.;"Cloning and B-cell-epitope.." Infection and Immunity May 1994, vol. 62, No. 5.
Nagai, Sadamu et al.; "Isolation and Partial.." Infection and Immunity, Jan. 1991, p. 372-382 vol. 59, No. 1.
Rosenkrands, Ida et al.;"Indentifcation and Characterization of.." Infection and Immunity Jun. 1998, p. 2728-2735 vol. 66, No. 6.
Roberts, A.D. eta I.; "Characteristics of protective immunity.." Immunology 1995 85 502-508.
Porath, Jerker et al.; "Thiophilic adsorption-0a new method.." FEBS Letters vol. 185, No. 2 FEBS 2631 Jun. 1985.
Valdes-Stauber, Natalia et al.; "Nucleotide Sequence and Taxonomical.." Applie dand Environmental Microbiology, Apr. 1996, p. 1283-1286 vol. 62.
Hochestrasser, Denis F. et al.; "Methods for increasing.." Analytical Biochemistry 173, 424-435 (1988).
Von Heijne, Gunanr; "How Signal Sequences maintain Cleavage Specificity" J. Moi. Bioi. (1984) 173, 243-251.
Harboe, Morten et al.; "Evidence for occurrence of the.." Infection and Immunity Jan. 1996, p. 16-22.
Gosselin, Edmund et al.;"Enhabnced antigen presentation.." Journal of Immunology vol. 149, 3477-3481 No. 11 Dec. 1, 1992.
Mahairas, Gregory G. et al.; "Molecular Analysis of.." American Society for Microbiology Oct. 20, 1995.
Lindblad, Erik B. et al.; "Adjuvant Modulation of.." Infection Immunity Feb. 1997, p. 623-629 vol. 65, No. 2.
Huayi, Li et al.; "Evidence for absence of the.." Ibfection and Immunity May 1993, p. 1730-1734 vol. 61, No. 5.
Kohler, G. et al.; "Continuous cultures of.." Nature vol. 256 Aug. 7, 1975.
Valdes-Stauber, Natalia et al.;"Isolation and Characterization.." A[pplied and Environmental Microbiology, Oct. 1994, vol. 60, No. 10 pp. 3809-3814.
Theisen, Michael eta I.;"Antigenicity and Immunogenicity.." Clinical and Diagnostic Lab. Immun. Jan. 1995, pp. 30-34 vol. 2, No. 1.
Sorensen, Anne L. et al.:"Purification and Characterization of a.." Insection and immunity May 1995, p. 1710-1717 vol. 63, No. 5.
Young, Richard et al.;"Dissection of *Mycobacterium tuberculosis*.." Proc. natl. Acad. Sci. vol. 82, pp. 2583-2587, May 1985.
Barkholt, Vibeke et al.;"Amino Acid Analysis:.." Analytical Biochemistry 177, 318-322 (1989).
Borodovsky, Mark et al.;"Genmark: Parallel Gene.."Computers Chem vol. 17, pp. 123-133, 1993.
Andersen, A.B. et al.;"Structure and Function.." Infection Immunity Jun. 1992, pp. 2317-2323 vol. 60, No. 6.

Article "Europeans move on from Yeast to TB" Science vol. 272, Apr. 5, 1996.
Van Dyke, M.W. et al.; "Single-step purification.." Gene pp. 99-104. (1992).
Brown, D. B. eta I.; "*Mycobacterium tuberculosis* cosmid v035" Feb. 20, 1998 EMBL Sequence Database.
Rosenkrands, Ida et al.;"*Mycobacterium tuberculosis* cfp29 gene" Jun. 30, 1997 EMBL:Y12820.
Churcher, C.M.C.; "*Mycobacterium tuberculosis* cosmid v035" Feb. 20, 1998 EMBL:Y12820.
Crabtree, J.C. et al.; *Homo sapiens* clone 137c7 Mar. 19, 1997 EMBL sequence database.
Abstract. Accession No. 053519, Database EMBL [Online], Rv2185c, Jun. 1, 1998. XP002274823.
Abstract. Accession No. 069575, Database EMBL [Online], ML0889, Aug. 1, 1998. XP002274824.
Andersen, Peter et al. XP-002300140.
Wiegesbaus, Ernst H. et al., "Evaluation of the Protective Potency of New Tuberculosis Vaccines," Reviews of Infectious Diseases, Mar.-Apr. 1989, vol. 2, Supplement 2, pp. S484-S490.
Orme, Jan M., "New vaccines against tuberculosis," New Vaccines and New Vaccine Technology, Mar. 1999, vol. 13, No. 1, pp. 169-185.
Rambukkana, et al., Infection and Immunity, (1992), vol. 60(12), pp. 5172-5181.
Andersen, et al, Scand J Immunol, (1997), vol. 45, pp. 115-131.
Cole, et al., (1998), EMBL-Sequence XP-002092185, ID #: MTV012, Accession #: AL0231298.
Phillip, et al., PNAS, (1996), vol. 93, pp. 3132-3137.
North, et al., Cell Immon, (1973), vol. 7, pp. 166-176.
Rammensee, et al., Immunogen, (1995), vol. 41, pp. 178-228.
Rammensee, et al., Curr Op Immun, (1995), vol. 7, pp. 85-96.
Engelhard, et al., Annu Rev Immunol, (1994) vol, 12, pp. 181-207.
Lee, et al., Infect Immun, (1992), vol. 60(5), pp. 2066-2074.
Mayr, et al., J Bacteriology, (1996), vol. 178(10), pp. 2916-2925.
Andersen, et al., Scan J Immunol, (1992), vol. 36, pp. 823-831.
Andersen, et al., Infect Immun, (1993), vol. 61(3), pp. 844-851.
Andersen, et al., Infect Immun, (1991), vol. 59(4), pp. 1558-1563.
Huygen, et al., Infect Immun, (1992), vol. 60(7), pp. 2880-2886.
Andersen, et al., Infect Immun, (1991), vol. 59(6), pp. 1905-1910.
Abou-Zeid, et al., Infect Immun, (1988), vol. 56(12), pp. 3046-3051.
Borremans, et al., Infect Immun, (1989), vol. 57(10), pp. 3123-3130.
Boswell, et al., Computation Molecular Biology, (1988), pp. 161-178.
Lefford, et al., Cellular Immunol, (1974), vol. 14, pp. 417-428.
Sanger, et al., PNAS, (1977), vol. 74(12), pp. 5463-5467.
Kaufman, Microbiol Sciences, (1987), vol. 4(11), pp. 324-328.
Lazar, et al., Molecular Cell Biol, (1988), vol. 8(3), pp. 1247-1252.
Burgess, et al., J Cell Biol, (1990), vol. 3, pp. 2129-2138.
Salgaller, et al., Cancer Immuno Immunother, (1994), vol. 39, pp. 105-116.
Man, et al., J Immunol Methods, (1989), vol. 125(1-2), pp. 251-259.
Andersen, et al., Scand J Immunol, 1991 , vol. 34, pp. 365-372.
Worsaae, et al., Infect Immun, (1987), pp. 2922-2927.
Yamaguchi, et al., Infect Immun, (1989), vol. 57(1), pp. 283-288.
Wiker, et al., Scand J Immunol, (1992), vol. 36, pp. 307-319.
Leao, et al., Brazilian J Med Biol Res, (1993), vol. 26, pp. 827-833.
Brandt, et al., J Immunol, (1996), vol. 157, pp. 3527-3533.
Brandt, et al., Infect Immun, (2000), vol. 68(2), pp. 791-795.
Olsen, et al, Eur J Immunol, (2000), vol. 30(6), pp. 1724-1732.
Roche, et al., Infect Immun, (1994), vol. 62(12), pp. 5319-5326.
Skjot, et al, Infect Immun, (2000), vol. 68(1), pp. 214-220.
Ulrichs, Eur J Immunol, (1998), vol. 28, pp. 3949-3958.
Stryhn, et al., Eur J Immunol, (1996), vol. 26, pp. 1911-1918.
Nielsen, et al., Database EMBL EBI accession No. 053693, May 30, 2000.
Harth, et al., Infect Immun, (1996), vol. 64(8), pp. 3038-3047.
Leal, et al., "Failure to induce enhanced protection against tuberculosis by increasing T-cell-dependent interferon-γ generation" Immunology, (2001), vol, 104, pp. 157-161.

SEQUENCE LISTING

<160> NUMBER OF SEQ ID NOS: 174

<210> SEQ ID NO 1
<211> LENGTH: 381
<212> TYPE: DNA
<213> ORGANISM: Mycobacterium tuberculosis

<400> SEQUENCE: 1

```
ggccgccggt acctatgtgg ccgccgatgc tgcggacgcg tcgacctata ccggggttctg    60 atcgaaccct gctgacagag aggacttgtg atgtcgcaaa tcatgtacaa ctaccccgcg   120
atgttgggtc acgccgggga tatggccgga tatgccggca cgctgcagag cttgggtgcc   180
gagatcgccg tggagcaggc cgcgttgcag agtgcgtggc agggcgatac cgggatcacg   240
tatcaggcgt ggcaggcaca gtggaaccag gccatggaag atttggtgcg ggcctatcat   300
gcgatgtcca gcacccatga agccaacacc atggcgatga tggcccgcga caccgccgaa   360
gccgccaaat ggggcggcta g                                             381
```

<210> SEQ ID NO 2
<211> LENGTH: 96
<212> TYPE: PRT
<213> ORGANISM: Mycobacterium tuberculosis

<400> SEQUENCE: 2

```
Met Ser Gln Ile Met Tyr Asn Tyr Pro Ala Met Leu Gly His Ala Gly
1               5                   10                  15

Asp Met Ala Gly Tyr Ala Gly Thr Leu Gln Ser Leu Gly Ala Glu Ile
            20                  25                  30

Ala Val Glu Gln Ala Ala Leu Gln Ser Ala Trp Gln Gly Asp Thr Gly
        35                  40                  45

Ile Thr Tyr Gln Ala Trp Gln Ala Gln Trp Asn Gln Ala Met Glu Asp
    50                  55                  60

Leu Val Arg Ala Tyr His Ala Met Ser Ser Thr His Glu Ala Asn Thr
65                  70                  75                  80

Met Ala Met Met Ala Arg Asp Thr Ala Glu Ala Ala Lys Trp Gly Gly
                85                  90                  95
```

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7
<211> LENGTH: 441
<212> TYPE: DNA
<213> ORGANISM: Mycobacterium tuberculosis
<220> FEATURE:
<221> NAME/KEY: CDS
<222> LOCATION: (1)...(438)

<400> SEQUENCE: 7

```
atg agc gcc tat aag acc gtg gtg gta gga acc gac ggt tcg gac tcg      48
Met Ser Ala Tyr Lys Thr Val Val Val Gly Thr Asp Gly Ser Asp Ser
1               5                   10                  15 tcg atg cga gcg gta gat cgc gct gcc cag atc gcc ggc gca gac gcc      96
Ser Met Arg Ala Val Asp Arg Ala Ala Gln Ile Ala Gly Ala Asp Ala
            20                  25                  30 aag ttg atc atc gcc tcg gca tac cta cct cag cac gag gac gct cgc     144
Lys Leu Ile Ile Ala Ser Ala Tyr Leu Pro Gln His Glu Asp Ala Arg
        35                  40                  45 gcc gcc gac att ctg aag gac gaa agc tac aag gtg acg ggc acc gcc     192
Ala Ala Asp Ile Leu Lys Asp Glu Ser Tyr Lys Val Thr Gly Thr Ala
    50                  55                  60 ccg atc tac gag atc ttg cac gac gcc aag gaa cga gcg cac aac gcc     240
Pro Ile Tyr Glu Ile Leu His Asp Ala Lys Glu Arg Ala His Asn Ala
65                  70                  75                  80 ggt gcg aaa aac gtc gag gaa cgg ccg atc gtc ggc gcc ccg gtc gac     288
Gly Ala Lys Asn Val Glu Glu Arg Pro Ile Val Gly Ala Pro Val Asp
                85                  90                  95 gcg ttg gtg aac ctg gcc gat gag gag aag gcg gac ctg ctg gtc gtc     336
Ala Leu Val Asn Leu Ala Asp Glu Glu Lys Ala Asp Leu Leu Val Val
            100                 105                 110 ggc aat gtc ggt ctg agc acg atc gcg ggt cgg ctg ctc gga tcg gta     384
Gly Asn Val Gly Leu Ser Thr Ile Ala Gly Arg Leu Leu Gly Ser Val
        115                 120                 125 ccg gcc aat gtg tca cgc cgg gcc aag gtc gac gtg ctg atc gtg cac     432
Pro Ala Asn Val Ser Arg Arg Ala Lys Val Asp Val Leu Ile Val His
    130                 135                 140 acc acc tag                                                          441
Thr Thr
145
```

<210> SEQ ID NO 8
<211> LENGTH: 146
<212> TYPE: PRT
<213> ORGANISM: Mycobacterium tuberculosis

<400> SEQUENCE: 8

```
Met Ser Ala Tyr Lys Thr Val Val Gly Thr Asp Gly Ser Asp Ser
 1               5                   10                  15

Ser Met Arg Ala Val Asp Arg Ala Ala Gln Ile Ala Gly Ala Asp Ala
             20                  25                  30

Lys Leu Ile Ile Ala Ser Ala Tyr Leu Pro Gln His Glu Asp Ala Arg
             35                  40                  45

Ala Ala Asp Ile Leu Lys Asp Glu Ser Tyr Lys Val Thr Gly Thr Ala
         50                  55                  60

Pro Ile Tyr Glu Ile Leu His Asp Ala Lys Glu Arg Ala His Asn Ala
 65                  70                  75                  80

Gly Ala Lys Asn Val Glu Glu Arg Pro Ile Val Gly Ala Pro Val Asp
                 85                  90                  95

Ala Leu Val Asn Leu Ala Asp Glu Glu Lys Ala Asp Leu Leu Val Val
                100                 105                 110

Gly Asn Val Gly Leu Ser Thr Ile Ala Gly Arg Leu Leu Gly Ser Val
            115                 120                 125

Pro Ala Asn Val Ser Arg Arg Ala Lys Val Asp Val Leu Ile Val His
        130                 135                 140

Thr Thr
145
```

<210> SEQ ID NO 9
<211> LENGTH: 1054
<212> TYPE: DNA
<213> ORGANISM: Mycobacterium tuberculosis
<220> FEATURE:
<221> NAME/KEY: CDS
<222> LOCATION: (201)...(854)

<400> SEQUENCE: 9

```
ataatcagct caccgttggg accgacctcg accaggggtc ctttgtgact gccgggcttg        60
acgcggacga ccacagagtc ggtcatcgcc taaggctacc gttctgacct ggggctgcgt       120
gggcgccgac gacgtgaggc acgtcatgtc tcagcggccc accgccacct cggtcgccgg       180
cagtatgtca gcatgtgcag atg act cca cgc agc ctt gtt cgc atc gtt           230
                      Met Thr Pro Arg Ser Leu Val Arg Ile Val
                      -32         -30                 -25 ggt gtc gtg gtt gcg acg acc ttg gcg ctg gtg agc gca ccc gcc ggc         278
Gly Val Val Val Ala Thr Thr Leu Ala Leu Val Ser Ala Pro Ala Gly
        -20                 -15                 -10 ggt cgt gcc gcg cat gcg gat ccg tgt tcg gac atc gcg gtc gtt ttc         326
Gly Arg Ala Ala His Ala Asp Pro Cys Ser Asp Ile Ala Val Val Phe
 -5                   1                   5                   10 gct cgc ggc acg cat cag gct tct ggt ctt ggc gac gtc ggt gag gcg         374
Ala Arg Gly Thr His Gln Ala Ser Gly Leu Gly Asp Val Gly Glu Ala
                 15                  20                  25 ttc gtc gac tcg ctt acc tcg caa gtt ggc ggg cgg tcg att ggg gtc         422
Phe Val Asp Ser Leu Thr Ser Gln Val Gly Gly Arg Ser Ile Gly Val
             30                  35                  40 tac gcg gtg aac tac cca gca agc gac gac tac cgc gcg agc gcg tca         470
Tyr Ala Val Asn Tyr Pro Ala Ser Asp Asp Tyr Arg Ala Ser Ala Ser
         45                  50                  55 aac ggt tcc gat gat gcg agc gcc cac atc cag cgc acc gtc gcc agc         518
```

```
              Asn Gly Ser Asp Asp Ala Ser Ala His Ile Gln Arg Thr Val Ala Ser
                   60                  65                  70 tgc ccg aac acc agg att gtg ctt ggt ggc tat tcg cag ggt gcg acg    566
Cys Pro Asn Thr Arg Ile Val Leu Gly Gly Tyr Ser Gln Gly Ala Thr
75                  80                  85                  90 gtc atc gat ttg tcc acc tcg gcg atg ccg ccc gcg gtg gca gat cat    614
Val Ile Asp Leu Ser Thr Ser Ala Met Pro Pro Ala Val Ala Asp His
                95                 100                 105 gtc gcc gct gtc gcc ctt ttc ggc gag cca tcc agt ggt ttc tcc agc    662
Val Ala Ala Val Ala Leu Phe Gly Glu Pro Ser Ser Gly Phe Ser Ser
            110                 115                 120 atg ttg tgg ggc ggc ggg tcg ttg cca aca atc ggt ccg ctg tat agc    710
Met Leu Trp Gly Gly Gly Ser Leu Pro Thr Ile Gly Pro Leu Tyr Ser
        125                 130                 135 tct aag acc ata aac ttg tgt gct ccc gac gat cca ata tgc acc gga    758
Ser Lys Thr Ile Asn Leu Cys Ala Pro Asp Asp Pro Ile Cys Thr Gly
    140                 145                 150 ggc ggc aat att atg gcg cat gtt tcg tat gtt cag tcg ggg atg aca    806
Gly Gly Asn Ile Met Ala His Val Ser Tyr Val Gln Ser Gly Met Thr
155                 160                 165                 170 agc cag gcg gcg aca ttc gcg gcg aac agg ctc gat cac gcc gga tga    854
Ser Gln Ala Ala Thr Phe Ala Ala Asn Arg Leu Asp His Ala Gly
                175                 180                 185 tcaaagactg ttgtccctat accgctgggg ctgtagtcga tgtacaccgg ctggaatctg   914
aagggcaaga acccggtatt catcaggccg gatgaaatga cggtcgggcg gtaatcgttt   974
gtgttgaacg cgtagagccg atcaccgccg gggctggtgt agacctcaat gtttgtgttc  1034
gccggcaggg ttccggatcc                                              1054

<210> SEQ ID NO 10
<211> LENGTH: 217
<212> TYPE: PRT
<213> ORGANISM: Mycobacterium tuberculosis

<400> SEQUENCE: 10

Met Thr Pro Arg Ser Leu Val Arg Ile Val Gly Val Val Ala Thr
-32         -30                 -25                 -20

Thr Leu Ala Leu Val Ser Ala Pro Ala Gly Gly Arg Ala His Ala
        -15                 -10                  -5

Asp Pro Cys Ser Asp Ile Ala Val Val Phe Ala Arg Gly Thr His Gln
  1               5                  10                  15

Ala Ser Gly Leu Gly Asp Val Gly Glu Ala Phe Val Asp Ser Leu Thr
                 20                  25                  30

Ser Gln Val Gly Gly Arg Ser Ile Gly Val Tyr Ala Val Asn Tyr Pro
         35                  40                  45

Ala Ser Asp Asp Tyr Arg Ala Ser Ala Ser Asn Gly Ser Asp Asp Ala
     50                  55                  60

Ser Ala His Ile Gln Arg Thr Val Ala Ser Cys Pro Asn Thr Arg Ile
 65                  70                  75                  80

Val Leu Gly Gly Tyr Ser Gln Gly Ala Thr Val Ile Asp Leu Ser Thr
                 85                  90                  95

Ser Ala Met Pro Pro Ala Val Ala Asp His Val Ala Ala Val Ala Leu
            100                 105                 110

Phe Gly Glu Pro Ser Ser Gly Phe Ser Ser Met Leu Trp Gly Gly Gly
        115                 120                 125

Ser Leu Pro Thr Ile Gly Pro Leu Tyr Ser Ser Lys Thr Ile Asn Leu
    130                 135                 140
```

```
Cys Ala Pro Asp Asp Pro Ile Cys Thr Gly Gly Gly Asn Ile Met Ala
145                 150                 155                 160

His Val Ser Tyr Val Gln Ser Gly Met Thr Ser Gln Ala Ala Thr Phe
                165                 170                 175

Ala Ala Asn Arg Leu Asp His Ala Gly
            180                 185

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000
```

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29
<211> LENGTH: 435
<212> TYPE: DNA
<213> ORGANISM: Mycobacterium tuberculosis
<220> FEATURE:
<221> NAME/KEY: CDS
<222> LOCATION: (1)...(435)

<400> SEQUENCE: 29

```
gtg gcg gac aag acg aca cag acg att tac atc gac gcg gat cca ggc        48
Val Ala Asp Lys Thr Thr Gln Thr Ile Tyr Ile Asp Ala Asp Pro Gly
 1               5                  10                  15 gag gtg atg aag gcg atc gcc gac atc gaa gcc tac ccg caa tgg att        96
Glu Val Met Lys Ala Ile Ala Asp Ile Glu Ala Tyr Pro Gln Trp Ile
            20                  25                  30 tcg gag tat aag gaa gtc gag atc cta gag gcc gac gac gag ggc tac       144
Ser Glu Tyr Lys Glu Val Glu Ile Leu Glu Ala Asp Asp Glu Gly Tyr
        35                  40                  45 ccg aaa cga gcg cga atg ttg atg gac gca gcc atc ttc aaa gac acc       192
Pro Lys Arg Ala Arg Met Leu Met Asp Ala Ala Ile Phe Lys Asp Thr
```

```
                50                   55                    60
ttg atc atg tcc tac gag tgg ccg gaa gac cgc caa tcg ctt agc tgg       240
Leu Ile Met Ser Tyr Glu Trp Pro Glu Asp Arg Gln Ser Leu Ser Trp
 65              70                  75                  80 act ctc gaa tcc agc tcg ctg cta aag tcc ctc gaa ggc acg tat cgc       288
Thr Leu Glu Ser Ser Ser Leu Leu Lys Ser Leu Glu Gly Thr Tyr Arg
                 85                  90                  95 ttg gcg ccc aag ggt tct ggc act gag gtc acc tac gag ctt gcc gtc       336
Leu Ala Pro Lys Gly Ser Gly Thr Glu Val Thr Tyr Glu Leu Ala Val
                100                 105                 110 gac ctt gct gtc ccc atg atc ggg atg ctc aag cgt aag gcg gaa cgc       384
Asp Leu Ala Val Pro Met Ile Gly Met Leu Lys Arg Lys Ala Glu Arg
            115                 120                 125 agg ttg ata gac ggc gcg ttg aag gat ctg aag aaa cga gtc gag ggc       432
Arg Leu Ile Asp Gly Ala Leu Lys Asp Leu Lys Lys Arg Val Glu Gly
130                 135                 140 tga                                                                   435
```

<210> SEQ ID NO 30
<211> LENGTH: 144
<212> TYPE: PRT
<213> ORGANISM: Mycobacterium tuberculosis

<400> SEQUENCE: 30

```
Met Ala Asp Lys Thr Thr Gln Thr Ile Tyr Ile Asp Ala Asp Pro Gly
  1               5                  10                  15

Glu Val Met Lys Ala Ile Ala Asp Ile Glu Ala Tyr Pro Gln Trp Ile
                 20                  25                  30

Ser Glu Tyr Lys Glu Val Glu Ile Leu Glu Ala Asp Asp Glu Gly Tyr
                 35                  40                  45

Pro Lys Arg Ala Arg Met Leu Met Asp Ala Ala Ile Phe Lys Asp Thr
 50                  55                  60

Leu Ile Met Ser Tyr Glu Trp Pro Glu Asp Arg Gln Ser Leu Ser Trp
 65                  70                  75                  80

Thr Leu Glu Ser Ser Ser Leu Leu Lys Ser Leu Glu Gly Thr Tyr Arg
                 85                  90                  95

Leu Ala Pro Lys Gly Ser Gly Thr Glu Val Thr Tyr Glu Leu Ala Val
                100                 105                 110

Asp Leu Ala Val Pro Met Ile Gly Met Leu Lys Arg Lys Ala Glu Arg
            115                 120                 125

Arg Leu Ile Asp Gly Ala Leu Lys Asp Leu Lys Lys Arg Val Glu Gly
130                 135                 140
```

<210> SEQ ID NO 31

<400> SEQUENCE: 31

000

<210> SEQ ID NO 32

<400> SEQUENCE: 32

000

<210> SEQ ID NO 33
<211> LENGTH: 894
<212> TYPE: DNA
<213> ORGANISM: Mycobacterium tuberculosis
<220> FEATURE:
<221> NAME/KEY: CDS

<222> LOCATION: (1)...(891)

<400> SEQUENCE: 33

| | | | | | | | | | | | | | | | | |
|---|---|---|---|---|---|---|---|---|---|---|---|---|---|---|---|---|
| atg | tca | tcg | ggc | aat | tca | tct | ctg | gga | att | atc | gtc | ggg | atc | gac | gat | 48 |
| Met | Ser | Ser | Gly | Asn | Ser | Ser | Leu | Gly | Ile | Ile | Val | Gly | Ile | Asp | Asp | |
| 1 | | | | 5 | | | | | 10 | | | | | 15 | | |
| tca | ccg | gcc | gca | cag | gtt | gcg | gtg | cgg | tgg | gca | gct | cgg | gat | gcg | gag | 96 |
| Ser | Pro | Ala | Ala | Gln | Val | Ala | Val | Arg | Trp | Ala | Ala | Arg | Asp | Ala | Glu | |
| | | | 20 | | | | | 25 | | | | | 30 | | | |
| ttg | cga | aaa | atc | cct | ctg | acg | ctc | gtg | cac | gcg | gtg | tcg | ccg | gaa | gta | 144 |
| Leu | Arg | Lys | Ile | Pro | Leu | Thr | Leu | Val | His | Ala | Val | Ser | Pro | Glu | Val | |
| | 35 | | | | | 40 | | | | | 45 | | | | | |
| gcc | acc | tgg | ctg | gag | gtg | cca | ctg | ccg | ccg | ggc | gtg | ctg | cga | tgg | cag | 192 |
| Ala | Thr | Trp | Leu | Glu | Val | Pro | Leu | Pro | Pro | Gly | Val | Leu | Arg | Trp | Gln | |
| 50 | | | | | 55 | | | | | 60 | | | | | | |
| cag | gat | cac | ggg | cgc | cac | ctg | atc | gac | gac | gca | ctc | aag | gtg | gtt | gaa | 240 |
| Gln | Asp | His | Gly | Arg | His | Leu | Ile | Asp | Asp | Ala | Leu | Lys | Val | Val | Glu | |
| 65 | | | | | 70 | | | | | 75 | | | | | 80 | |
| cag | gct | tcg | ctg | cgc | gct | ggt | ccc | ccc | acg | gtc | cac | agt | gaa | atc | gtt | 288 |
| Gln | Ala | Ser | Leu | Arg | Ala | Gly | Pro | Pro | Thr | Val | His | Ser | Glu | Ile | Val | |
| | | | 85 | | | | | 90 | | | | | 95 | | | |
| ccg | gcg | gca | gcc | gtt | ccc | aca | ttg | gtc | gac | atg | tcc | aaa | gac | gca | gtg | 336 |
| Pro | Ala | Ala | Ala | Val | Pro | Thr | Leu | Val | Asp | Met | Ser | Lys | Asp | Ala | Val | |
| | | | 100 | | | | | 105 | | | | | 110 | | | |
| ctg | atg | gtc | gtg | ggt | tgt | ctc | gga | agt | ggg | cgg | tgg | ccg | ggc | cgg | ctg | 384 |
| Leu | Met | Val | Val | Gly | Cys | Leu | Gly | Ser | Gly | Arg | Trp | Pro | Gly | Arg | Leu | |
| | 115 | | | | | 120 | | | | | 125 | | | | | |
| ctc | ggt | tcg | gtc | agt | tcc | ggc | ctg | ctc | cgc | cac | gcg | cac | tgt | ccg | gtc | 432 |
| Leu | Gly | Ser | Val | Ser | Ser | Gly | Leu | Leu | Arg | His | Ala | His | Cys | Pro | Val | |
| 130 | | | | | 135 | | | | | 140 | | | | | | |
| gtg | atc | atc | cac | gac | gaa | gat | tcg | gtg | atg | ccg | cat | ccc | cag | caa | gcg | 480 |
| Val | Ile | Ile | His | Asp | Glu | Asp | Ser | Val | Met | Pro | His | Pro | Gln | Gln | Ala | |
| 145 | | | | | 150 | | | | | 155 | | | | | 160 | |
| ccg | gtg | cta | gtt | ggc | gtt | gac | ggc | tcg | tcg | gcc | tcc | gag | ctg | gcg | acc | 528 |
| Pro | Val | Leu | Val | Gly | Val | Asp | Gly | Ser | Ser | Ala | Ser | Glu | Leu | Ala | Thr | |
| | | | 165 | | | | | 170 | | | | | 175 | | | |
| gca | atc | gca | ttc | gac | gaa | gcg | tcg | cgg | cga | aac | gtg | gac | ctg | gtg | gcg | 576 |
| Ala | Ile | Ala | Phe | Asp | Glu | Ala | Ser | Arg | Arg | Asn | Val | Asp | Leu | Val | Ala | |
| | | | 180 | | | | | 185 | | | | | 190 | | | |
| ctg | cac | gca | tgg | agc | gac | gtc | gat | gtg | tcg | gag | tgg | ccc | gga | atc | gat | 624 |
| Leu | His | Ala | Trp | Ser | Asp | Val | Asp | Val | Ser | Glu | Trp | Pro | Gly | Ile | Asp | |
| | 195 | | | | | 200 | | | | | 205 | | | | | |
| tgg | ccg | gca | act | cag | tcg | atg | gcc | gag | cag | gtg | ctg | gcc | gag | cgg | ttg | 672 |
| Trp | Pro | Ala | Thr | Gln | Ser | Met | Ala | Glu | Gln | Val | Leu | Ala | Glu | Arg | Leu | |
| 210 | | | | | 215 | | | | | 220 | | | | | | |
| gcg | ggt | tgg | cag | gag | cgg | tat | ccc | aac | gta | gcc | ata | acc | cgc | gtg | gtg | 720 |
| Ala | Gly | Trp | Gln | Glu | Arg | Tyr | Pro | Asn | Val | Ala | Ile | Thr | Arg | Val | Val | |
| 225 | | | | | 230 | | | | | 235 | | | | | 240 | |
| gtg | cgc | gat | cag | ccg | gcc | cgc | cag | ctc | gtc | caa | cgc | tcc | gag | gaa | gcc | 768 |
| Val | Arg | Asp | Gln | Pro | Ala | Arg | Gln | Leu | Val | Gln | Arg | Ser | Glu | Glu | Ala | |
| | | | 245 | | | | | 250 | | | | | 255 | | | |
| cag | ctg | gtc | gtg | gtc | ggc | agc | cgg | ggc | cgc | ggc | ggc | tac | gcc | gga | atg | 816 |
| Gln | Leu | Val | Val | Val | Gly | Ser | Arg | Gly | Arg | Gly | Gly | Tyr | Ala | Gly | Met | |
| | | | 260 | | | | | 265 | | | | | 270 | | | |
| ctg | gtg | ggg | tcg | gta | ggc | gaa | acc | gtt | gct | cag | ctg | gcg | cgg | acg | ccg | 864 |
| Leu | Val | Gly | Ser | Val | Gly | Glu | Thr | Val | Ala | Gln | Leu | Ala | Arg | Thr | Pro | |
| | 275 | | | | | 280 | | | | | 285 | | | | | |
| gtc | atc | gtg | gca | cgc | gag | tcg | ctg | act | tag | | | | | | | 894 |
| Val | Ile | Val | Ala | Arg | Glu | Ser | Leu | Thr | | | | | | | | |
| | 290 | | | | | 295 | | | | | | | | | | |

<210> SEQ ID NO 34
<211> LENGTH: 297
<212> TYPE: PRT
<213> ORGANISM: Mycobacterium tuberculosis

<400> SEQUENCE: 34

Met Ser Ser Gly Asn Ser Ser Leu Gly Ile Ile Val Gly Ile Asp Asp
1               5                   10                  15

Ser Pro Ala Ala Gln Val Ala Val Arg Trp Ala Ala Arg Asp Ala Glu
            20                  25                  30

Leu Arg Lys Ile Pro Leu Thr Leu Val His Ala Val Ser Pro Glu Val
        35                  40                  45

Ala Thr Trp Leu Glu Val Pro Leu Pro Pro Gly Val Leu Arg Trp Gln
    50                  55                  60

Gln Asp His Gly Arg His Leu Ile Asp Asp Ala Leu Lys Val Val Glu
65                  70                  75                  80

Gln Ala Ser Leu Arg Ala Gly Pro Pro Thr Val His Ser Glu Ile Val
                85                  90                  95

Pro Ala Ala Ala Val Pro Thr Leu Val Asp Met Ser Lys Asp Ala Val
            100                 105                 110

Leu Met Val Val Gly Cys Leu Gly Ser Gly Arg Trp Pro Gly Arg Leu
        115                 120                 125

Leu Gly Ser Val Ser Ser Gly Leu Leu Arg His Ala His Cys Pro Val
    130                 135                 140

Val Ile Ile His Asp Glu Asp Ser Val Met Pro His Pro Gln Gln Ala
145                 150                 155                 160

Pro Val Leu Val Gly Val Asp Gly Ser Ala Ser Glu Leu Ala Thr
                165                 170                 175

Ala Ile Ala Phe Asp Glu Ala Ser Arg Arg Asn Val Asp Leu Val Ala
            180                 185                 190

Leu His Ala Trp Ser Asp Val Asp Val Ser Glu Trp Pro Gly Ile Asp
        195                 200                 205

Trp Pro Ala Thr Gln Ser Met Ala Glu Gln Val Leu Ala Glu Arg Leu
    210                 215                 220

Ala Gly Trp Gln Glu Arg Tyr Pro Asn Val Ala Ile Thr Arg Val Val
225                 230                 235                 240

Val Arg Asp Gln Pro Ala Arg Gln Leu Val Gln Arg Ser Glu Glu Ala
                245                 250                 255

Gln Leu Val Val Val Gly Ser Arg Gly Arg Gly Gly Tyr Ala Gly Met
            260                 265                 270

Leu Val Gly Ser Val Gly Glu Thr Val Ala Gln Leu Ala Arg Thr Pro
        275                 280                 285

Val Ile Val Ala Arg Glu Ser Leu Thr
    290                 295

<210> SEQ ID NO 35

<400> SEQUENCE: 35

000

<210> SEQ ID NO 36

<400> SEQUENCE: 36

000

<210> SEQ ID NO 37
<211> LENGTH: 1401
<212> TYPE: DNA
<213> ORGANISM: Mycobacterium tuberculosis
<220> FEATURE:
<221> NAME/KEY: CDS
<222> LOCATION: (1)...(1398)

<400> SEQUENCE: 37

| gtg aag agc acc gtc gag cag ttg agc ccc acc cgg gtt cgt atc aac | 48 |
| Val Lys Ser Thr Val Glu Gln Leu Ser Pro Thr Arg Val Arg Ile Asn | |
| 1               5                   10                  15 | |

| gtg gag gtg cca ttc gcc gag ctt gag ccg gat ttc cag cgg gcc tac | 96 |
| Val Glu Val Pro Phe Ala Glu Leu Glu Pro Asp Phe Gln Arg Ala Tyr | |
|             20                  25                  30 | |

| aaa gag ctg gcc aaa cag gtg cgg ctg ccc ggc ttc cgg ccc ggg aag | 144 |
| Lys Glu Leu Ala Lys Gln Val Arg Leu Pro Gly Phe Arg Pro Gly Lys | |
|         35                  40                  45 | |

| gcg ccg gcc aaa cta ctc gaa gcc cgc atc ggc cgg gag gcc atg ctg | 192 |
| Ala Pro Ala Lys Leu Leu Glu Ala Arg Ile Gly Arg Glu Ala Met Leu | |
|     50                  55                  60 | |

| gat caa atc gtc aac gat gcg ctg ccc agc cgg tac gga cag gcg gtg | 240 |
| Asp Gln Ile Val Asn Asp Ala Leu Pro Ser Arg Tyr Gly Gln Ala Val | |
| 65                  70                  75                  80 | |

| gcc gag tcg gat gtc caa ccg ctc ggc cgg ccc aac atc gag gtg acc | 288 |
| Ala Glu Ser Asp Val Gln Pro Leu Gly Arg Pro Asn Ile Glu Val Thr | |
|                 85                  90                  95 | |

| aag aag gag tac ggc cag gac ctg caa ttc acc gcc gag gtc gac atc | 336 |
| Lys Lys Glu Tyr Gly Gln Asp Leu Gln Phe Thr Ala Glu Val Asp Ile | |
|             100                 105                 110 | |

| cgc ccg aag atc agt ccc ccg gac ctg agc gcg ctg acg gtc tcg gtg | 384 |
| Arg Pro Lys Ile Ser Pro Pro Asp Leu Ser Ala Leu Thr Val Ser Val | |
|         115                 120                 125 | |

| gat ccg atc gaa atc ggt gag gac gac gtc gac gcc gaa ctg cag tcg | 432 |
| Asp Pro Ile Glu Ile Gly Glu Asp Asp Val Asp Ala Glu Leu Gln Ser | |
|     130                 135                 140 | |

| tta cgt acc cgg ttc ggc acc ctg acc gcg gtg gac cgg ccg gtg gcc | 480 |
| Leu Arg Thr Arg Phe Gly Thr Leu Thr Ala Val Asp Arg Pro Val Ala | |
| 145                 150                 155                 160 | |

| gtc ggc gac gtc gtc tcg atc gac ttg tct gcc acg gtc gac gga gag | 528 |
| Val Gly Asp Val Val Ser Ile Asp Leu Ser Ala Thr Val Asp Gly Glu | |
|                 165                 170                 175 | |

| gac ata ccg aac gca gcc gct gag gga ctc tcc cac gag gtc ggc tcc | 576 |
| Asp Ile Pro Asn Ala Ala Ala Glu Gly Leu Ser His Glu Val Gly Ser | |
|             180                 185                 190 | |

| ggc cgg ctc atc gca ggt ctc gac gac gcg gtt gtt ggt ctg tcc gcc | 624 |
| Gly Arg Leu Ile Ala Gly Leu Asp Asp Ala Val Val Gly Leu Ser Ala | |
|         195                 200                 205 | |

| gac gag tcc cgg gtc ttc acc gcc aag ctg gca gcc ggc gag cac gcc | 672 |
| Asp Glu Ser Arg Val Phe Thr Ala Lys Leu Ala Ala Gly Glu His Ala | |
|     210                 215                 220 | |

| ggg cag gaa gct cag gtt acc gtc acg gtc agg tcg gtt aag gag cgc | 720 |
| Gly Gln Glu Ala Gln Val Thr Val Thr Val Arg Ser Val Lys Glu Arg | |
| 225                 230                 235                 240 | |

| gaa cta cca gag ccc gac gac gaa ttc gcg cag tta gcc agc gag ttc | 768 |
| Glu Leu Pro Glu Pro Asp Asp Glu Phe Ala Gln Leu Ala Ser Glu Phe | |
|                 245                 250                 255 | |

| gac agc atc gac gaa ttg cgg gcc agc ctc agc gac cag gtg cgc cag | 816 |
| Asp Ser Ile Asp Glu Leu Arg Ala Ser Leu Ser Asp Gln Val Arg Gln | |
|             260                 265                 270 | |

| gcc aag cgc gcc cag cag gcc gag cag att cga aac gcc acc atc gat | 864 |
| Ala Lys Arg Ala Gln Gln Ala Glu Gln Ile Arg Asn Ala Thr Ile Asp | |

```
                275                 280                 285
gcg cta ctc gaa cag gtc gac gtg ccg ttg ccg gag tcg tat gtg cag         912
Ala Leu Leu Glu Gln Val Asp Val Pro Leu Pro Glu Ser Tyr Val Gln
    290                 295                 300 gcc caa ttc gac agc gtg ctg cac agc gcg ctc agc ggt ctt aat cac         960
Ala Gln Phe Asp Ser Val Leu His Ser Ala Leu Ser Gly Leu Asn His
305                 310                 315                 320 gac gaa gcc cgg ttc aat gag ttg ctc gtc gag caa ggc tcg tca cgc        1008
Asp Glu Ala Arg Phe Asn Glu Leu Leu Val Glu Gln Gly Ser Ser Arg
                325                 330                 335 gcg gcg ttc gat gcc gag gcg cgc acc gcc tca gaa aag gac gtc aag        1056
Ala Ala Phe Asp Ala Glu Ala Arg Thr Ala Ser Glu Lys Asp Val Lys
            340                 345                 350 agg cag ctg ttg cta gac gcc ctg gcc gat gag ctg cag gtc caa gtt        1104
Arg Gln Leu Leu Leu Asp Ala Leu Ala Asp Glu Leu Gln Val Gln Val
        355                 360                 365 ggc cag gat gat ctg acc gaa cga ctg gtg acg acg tct cgg caa tac        1152
Gly Gln Asp Asp Leu Thr Glu Arg Leu Val Thr Thr Ser Arg Gln Tyr
370                 375                 380 ggc atc gag ccg cag cag ctg ttc ggc tac ctc caa gag cgc aac cag        1200
Gly Ile Glu Pro Gln Gln Leu Phe Gly Tyr Leu Gln Glu Arg Asn Gln
385                 390                 395                 400 ctg ccg acc atg ttc gct gac gtg cgg cgc gag ctg gcg atc agg gcc        1248
Leu Pro Thr Met Phe Ala Asp Val Arg Arg Glu Leu Ala Ile Arg Ala
                405                 410                 415 gca gtg gag gcg gcg acg gtc acc gac agt gac gga aac acg atc gat        1296
Ala Val Glu Ala Ala Thr Val Thr Asp Ser Asp Gly Asn Thr Ile Asp
            420                 425                 430 acc agt gag ttc ttc ggc aag cgt gtg tcg gcc ggt gag gct gag gag        1344
Thr Ser Glu Phe Phe Gly Lys Arg Val Ser Ala Gly Glu Ala Glu Glu
        435                 440                 445 gcc gaa ccg gca gac gag ggt gcc gcg cgg gcg gcg tcc gac gaa gcg        1392
Ala Glu Pro Ala Asp Glu Gly Ala Ala Arg Ala Ala Ser Asp Glu Ala
450                 455                 460 aca acg tga                                                            1401
Thr Thr
465

<210> SEQ ID NO 38
<211> LENGTH: 466
<212> TYPE: PRT
<213> ORGANISM: Mycobacterium tuberculosis

<400> SEQUENCE: 38

Met Lys Ser Thr Val Glu Gln Leu Ser Pro Thr Arg Val Arg Ile Asn
1               5                   10                  15

Val Glu Val Pro Phe Ala Glu Leu Glu Pro Asp Phe Gln Arg Ala Tyr
            20                  25                  30

Lys Glu Leu Ala Lys Gln Val Arg Leu Pro Gly Phe Arg Pro Gly Lys
        35                  40                  45

Ala Pro Ala Lys Leu Leu Glu Ala Arg Ile Gly Arg Glu Ala Met Leu
    50                  55                  60

Asp Gln Ile Val Asn Asp Ala Leu Pro Ser Arg Tyr Gly Gln Ala Val
65                  70                  75                  80

Ala Glu Ser Asp Val Gln Pro Leu Gly Arg Pro Asn Ile Glu Val Thr
                85                  90                  95

Lys Lys Glu Tyr Gly Gln Asp Leu Gln Phe Thr Ala Glu Val Asp Ile
            100                 105                 110

Arg Pro Lys Ile Ser Pro Pro Asp Leu Ser Ala Leu Thr Val Ser Val
```

```
            115                 120                 125
Asp Pro Ile Glu Ile Gly Glu Asp Val Asp Ala Glu Leu Gln Ser
130                 135                 140
Leu Arg Thr Arg Phe Gly Thr Leu Thr Ala Val Asp Arg Pro Val Ala
145                 150                 155                 160
Val Gly Asp Val Val Ser Ile Asp Leu Ser Ala Thr Val Asp Gly Glu
                    165                 170                 175
Asp Ile Pro Asn Ala Ala Ala Glu Gly Leu Ser His Glu Val Gly Ser
                180                 185                 190
Gly Arg Leu Ile Ala Gly Leu Asp Asp Ala Val Val Gly Leu Ser Ala
            195                 200                 205
Asp Glu Ser Arg Val Phe Thr Ala Lys Leu Ala Ala Gly Glu His Ala
210                 215                 220
Gly Gln Glu Ala Gln Val Thr Val Thr Val Arg Ser Val Lys Glu Arg
225                 230                 235                 240
Glu Leu Pro Glu Pro Asp Asp Glu Phe Ala Gln Leu Ala Ser Glu Phe
                    245                 250                 255
Asp Ser Ile Asp Glu Leu Arg Ala Ser Leu Ser Asp Gln Val Arg Gln
                260                 265                 270
Ala Lys Arg Ala Gln Gln Ala Glu Gln Ile Arg Asn Ala Thr Ile Asp
            275                 280                 285
Ala Leu Leu Glu Gln Val Asp Val Pro Leu Pro Glu Ser Tyr Val Gln
290                 295                 300
Ala Gln Phe Asp Ser Val Leu His Ser Ala Leu Ser Gly Leu Asn His
305                 310                 315                 320
Asp Glu Ala Arg Phe Asn Glu Leu Leu Val Glu Gln Gly Ser Ser Arg
                    325                 330                 335
Ala Ala Phe Asp Ala Glu Ala Arg Thr Ala Ser Glu Lys Asp Val Lys
                340                 345                 350
Arg Gln Leu Leu Leu Asp Ala Leu Ala Asp Glu Leu Gln Val Gln Val
            355                 360                 365
Gly Gln Asp Asp Leu Thr Glu Arg Leu Val Thr Thr Ser Arg Gln Tyr
370                 375                 380
Gly Ile Glu Pro Gln Gln Leu Phe Gly Tyr Leu Gln Glu Arg Asn Gln
385                 390                 395                 400
Leu Pro Thr Met Phe Ala Asp Val Arg Arg Glu Leu Ala Ile Arg Ala
                    405                 410                 415
Ala Val Glu Ala Ala Thr Val Thr Asp Ser Asp Gly Asn Thr Ile Asp
                420                 425                 430
Thr Ser Glu Phe Phe Gly Lys Arg Val Ser Ala Gly Glu Ala Glu Glu
            435                 440                 445
Ala Glu Pro Ala Asp Glu Gly Ala Ala Arg Ala Ala Ser Asp Glu Ala
450                 455                 460
Thr Thr
465

<210> SEQ ID NO 39

<400> SEQUENCE: 39

000

<210> SEQ ID NO 40

<400> SEQUENCE: 40
```

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55
<211> LENGTH: 950
<212> TYPE: DNA
<213> ORGANISM: Mycobacterium tuberculosis
<220> FEATURE:
<221> NAME/KEY: CDS
<222> LOCATION: (133)...(918)

<400> SEQUENCE: 55

```
tgggctcggc actggctctc ccacggtggc gcgctgattt ctccccacgg taggcgttgc      60
gacgcatgtt cttcaccgtc tatccacagc taccgacatt tgctccggct ggatcgcggg     120
taaaattccg tc gtg aac aat cga ccc atc cgc ctg ctg aca tcc ggc agg     171
            Met Asn Asn Arg Pro Ile Arg Leu Leu Thr Ser Gly Arg
                -30                 -25 gct ggt ttg ggt gcg ggc gca ttg atc acc gcc gtc gtc ctg ctc atc      219
Ala Gly Leu Gly Ala Gly Ala Leu Ile Thr Ala Val Val Leu Leu Ile
-20              -15              -10               -5 gcc ttg ggc gct gtt tgg acc ccg gtt gcc ttc gcc gat gga tgc ccg      267
Ala Leu Gly Ala Val Trp Thr Pro Val Ala Phe Ala Asp Gly Cys Pro
                  1               5                10 gac gcc gaa gtc acg ttc gcc cgc ggc acc ggc gag ccg ccc gga atc      315
Asp Ala Glu Val Thr Phe Ala Arg Gly Thr Gly Glu Pro Pro Gly Ile
         15                  20                  25 ggg cgc gtt ggc cag gcg ttc gtc gac tcg ctg cgc cag cag act ggc      363
Gly Arg Val Gly Gln Ala Phe Val Asp Ser Leu Arg Gln Gln Thr Gly
     30                  35                  40 atg gag atc gga gta tac ccg gtg aat tac gcc gcc agc cgc cta cag      411
Met Glu Ile Gly Val Tyr Pro Val Asn Tyr Ala Ala Ser Arg Leu Gln
 45                  50                  55                  60 ctg cac ggg gga gac ggc gcc aac gac gcc ata tcg cac att aag tcc      459
Leu His Gly Gly Asp Gly Ala Asn Asp Ala Ile Ser His Ile Lys Ser
                 65                  70                  75 atg gcc tcg tca tgc ccg aac acc aag ctg gtc ttg ggc ggc tat tcg      507
Met Ala Ser Ser Cys Pro Asn Thr Lys Leu Val Leu Gly Gly Tyr Ser
             80                  85                  90 cag ggc gca acc gtg atc gat atc gtg gcc ggg gtt ccg ttg ggc agc      555
Gln Gly Ala Thr Val Ile Asp Ile Val Ala Gly Val Pro Leu Gly Ser
         95                 100                 105 atc agc ttt ggc agt ccg cta cct gcg gca tac gca gac aac gtc gca      603
Ile Ser Phe Gly Ser Pro Leu Pro Ala Ala Tyr Ala Asp Asn Val Ala
    110                 115                 120 gcg gtc gcg gtc ttc ggc aat ccg tcc aac cgc gcc ggc gga tcg ctg      651
Ala Val Ala Val Phe Gly Asn Pro Ser Asn Arg Ala Gly Gly Ser Leu
125                 130                 135                 140 tcg agc ctg agc ccg cta ttc ggt tcc aag gcg att gac ctg tgc aat      699
```

```
Ser Ser Leu Ser Pro Leu Phe Gly Ser Lys Ala Ile Asp Leu Cys Asn
            145                 150                 155 ccc acc gat ccg atc tgc cat gtg ggc ccc ggc aac gaa ttc agc gga      747
Pro Thr Asp Pro Ile Cys His Val Gly Pro Gly Asn Glu Phe Ser Gly
            160                 165                 170 cac atc gac ggc tac ata ccc acc tac acc acc cag gcg gct agt ttc      795
His Ile Asp Gly Tyr Ile Pro Thr Tyr Thr Thr Gln Ala Ala Ser Phe
            175                 180                 185 gtc gtg cag agg ctc cgc gcc ggg tcg gtg cca cat ctg cct gga tcc      843
Val Val Gln Arg Leu Arg Ala Gly Ser Val Pro His Leu Pro Gly Ser
        190                 195                 200 gtc ccg cag ctg ccc ggg tct gtc ctt cag atg ccc ggc act gcc gca      891
Val Pro Gln Leu Pro Gly Ser Val Leu Gln Met Pro Gly Thr Ala Ala
205                 210                 215                 220 ccg gct ccc gaa tcg ctg cac ggt cgc tgacgctttg tcagtaagcc cataaaa    945
Pro Ala Pro Glu Ser Leu His Gly Arg
                    225 tcgcg                                                                950

<210> SEQ ID NO 56
<211> LENGTH: 262
<212> TYPE: PRT
<213> ORGANISM: Mycobacterium tuberculosis

<400> SEQUENCE: 56

Met Asn Asn Arg Pro Ile Arg Leu Leu Thr Ser Gly Arg Ala Gly Leu
            -30                 -25                 -20

Gly Ala Gly Ala Leu Ile Thr Ala Val Val Leu Leu Ile Ala Leu Gly
        -15                 -10                  -5

Ala Val Trp Thr Pro Val Ala Phe Ala Asp Gly Cys Pro Asp Ala Glu
  1               5                  10                  15

Val Thr Phe Ala Arg Gly Thr Gly Glu Pro Pro Gly Ile Gly Arg Val
                 20                  25                  30

Gly Gln Ala Phe Val Asp Ser Leu Arg Gln Gln Thr Gly Met Glu Ile
             35                  40                  45

Gly Val Tyr Pro Val Asn Tyr Ala Ala Ser Arg Leu Gln Leu His Gly
         50                  55                  60

Gly Asp Gly Ala Asn Asp Ala Ile Ser His Ile Lys Ser Met Ala Ser
     65                  70                  75

Ser Cys Pro Asn Thr Lys Leu Val Leu Gly Gly Tyr Ser Gln Gly Ala
 80                  85                  90                  95

Thr Val Ile Asp Ile Val Ala Gly Val Pro Leu Gly Ser Ile Ser Phe
                100                 105                 110

Gly Ser Pro Leu Pro Ala Ala Tyr Ala Asp Asn Val Ala Ala Val Ala
            115                 120                 125

Val Phe Gly Asn Pro Ser Asn Arg Ala Gly Gly Ser Leu Ser Ser Leu
        130                 135                 140

Ser Pro Leu Phe Gly Ser Lys Ala Ile Asp Leu Cys Asn Pro Thr Asp
    145                 150                 155                 160

Pro Ile Cys His Val Gly Pro Gly Asn Glu Phe Ser Gly His Ile Asp
                165                 170                 175

Gly Tyr Ile Pro Thr Tyr Thr Thr Gln Ala Ala Ser Phe Val Val Gln
            180                 185                 190

Arg Leu Arg Ala Gly Ser Val Pro His Leu Pro Gly Ser Val Pro Gln
        195                 200                 205

Leu Pro Gly Ser Val Leu Gln Met Pro Gly Thr Ala Ala Pro Ala Pro
    210                 215                 220
```

```
Glu Ser Leu His Gly Arg
    225

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63
<211> LENGTH: 550
<212> TYPE: DNA
<213> ORGANISM: Mycobacterium tuberculosis
<220> FEATURE:
<221> NAME/KEY: CDS
<222> LOCATION: (101)...(490)

<400> SEQUENCE: 63
ggcccggctc gcggccgccc tgcaggaaaa gaaggcctgc ccaggcccag actcagccga       60
gtagtcaccc agtaccccac accaggaagg accgcccatc atg gca aag ctc tcc      115
                                              Met Ala Lys Leu Ser
                                                1               5 acc gac gaa ctg ctg gac gcg ttc aag gaa atg acc ctg ttg gag ctc      163
Thr Asp Glu Leu Leu Asp Ala Phe Lys Glu Met Thr Leu Leu Glu Leu
             10                  15                  20 tcc gac ttc gtc aag aag ttc gag gag acc ttc gag gtc acc gcc gcc      211
Ser Asp Phe Val Lys Lys Phe Glu Glu Thr Phe Glu Val Thr Ala Ala
         25                  30                  35 gct cca gtc gcc gtc gcc gcc gcc ggt gcc gcc ccg gcc ggt gcc gcc      259
Ala Pro Val Ala Val Ala Ala Ala Gly Ala Ala Pro Ala Gly Ala Ala
     40                  45                  50 gtc gag gct gcc gag gag cag tcc gag ttc gac gtg atc ctt gag gcc      307
Val Glu Ala Ala Glu Glu Gln Ser Glu Phe Asp Val Ile Leu Glu Ala
 55                  60                  65 gcc ggc gac aag aag atc ggc gtc atc aag gtg gtc cgg gag atc gtt      355
```

```
                Ala Gly Asp Lys Lys Ile Gly Val Ile Lys Val Val Arg Glu Ile Val
                 70                  75                  80                  85 tcc ggc ctg ggc ctc aag gag gcc aag gac ctg gtc gac ggc gcg ccc          403
Ser Gly Leu Gly Leu Lys Glu Ala Lys Asp Leu Val Asp Gly Ala Pro
         90                  95                 100 aag ccg ctg ctg gag aag gtc gcc aag gag gcc gcc gac gag gcc aag          451
Lys Pro Leu Leu Glu Lys Val Ala Lys Glu Ala Ala Asp Glu Ala Lys
                105                 110                 115 gcc aag ctg gag gcc gcc ggc gcc acc gtc acc gtc aag tagctctgcc ca        502
Ala Lys Leu Glu Ala Ala Gly Ala Thr Val Thr Val Lys
        120                 125                 130 gcgtgttctt ttgcgtctgc tcggcccgta gcgaacactg cgcccgct                     550
```

<210> SEQ ID NO 64
<211> LENGTH: 130
<212> TYPE: PRT
<213> ORGANISM: Mycobacterium tuberculosis

<400> SEQUENCE: 64

```
Met Ala Lys Leu Ser Thr Asp Glu Leu Leu Asp Ala Phe Lys Glu Met
  1               5                  10                  15

Thr Leu Leu Glu Leu Ser Asp Phe Val Lys Lys Phe Glu Glu Thr Phe
             20                  25                  30

Glu Val Thr Ala Ala Ala Pro Val Ala Val Ala Ala Gly Ala Ala
         35                  40                  45

Pro Ala Gly Ala Ala Val Glu Ala Ala Glu Glu Gln Ser Glu Phe Asp
     50                  55                  60

Val Ile Leu Glu Ala Ala Gly Asp Lys Lys Ile Gly Val Ile Lys Val
 65                  70                  75                  80

Val Arg Glu Ile Val Ser Gly Leu Gly Leu Lys Glu Ala Lys Asp Leu
                 85                  90                  95

Val Asp Gly Ala Pro Lys Pro Leu Leu Glu Lys Val Ala Lys Glu Ala
            100                 105                 110

Ala Asp Glu Ala Lys Ala Lys Leu Glu Ala Ala Gly Ala Thr Val Thr
        115                 120                 125

Val Lys
    130
```

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69
<400> SEQUENCE: 69
000

<210> SEQ ID NO 70
<400> SEQUENCE: 70
000

<210> SEQ ID NO 71
<400> SEQUENCE: 71
000

<210> SEQ ID NO 72
<400> SEQUENCE: 72
000

<210> SEQ ID NO 73
<400> SEQUENCE: 73
000

<210> SEQ ID NO 74
<400> SEQUENCE: 74
000

<210> SEQ ID NO 75
<400> SEQUENCE: 75
000

<210> SEQ ID NO 76
<400> SEQUENCE: 76
000

<210> SEQ ID NO 77
<400> SEQUENCE: 77
000

<210> SEQ ID NO 78
<400> SEQUENCE: 78
000

<210> SEQ ID NO 79
<400> SEQUENCE: 79
000

<210> SEQ ID NO 80

<400> SEQUENCE: 80

000

<210> SEQ ID NO 81
<400> SEQUENCE: 81

000

<210> SEQ ID NO 82
<400> SEQUENCE: 82

000

<210> SEQ ID NO 83
<400> SEQUENCE: 83

000

<210> SEQ ID NO 84
<400> SEQUENCE: 84

000

<210> SEQ ID NO 85
<400> SEQUENCE: 85

000

<210> SEQ ID NO 86
<400> SEQUENCE: 86

000

<210> SEQ ID NO 87
<211> LENGTH: 450
<212> TYPE: DNA
<213> ORGANISM: Mycobacterium tuberculosis
<220> FEATURE:
<221> NAME/KEY: CDS
<222> LOCATION: (107)...(400)

<400> SEQUENCE: 87

```
agcccggtaa tcgagttcgg gcaatgctga ccatcgggtt tgtttccggc tataaccgaa      60
cggtttgtgt acgggataca aatacaggga gggaagaagt aggcaa atg gaa aaa       115
                                                     Met Glu Lys
                                                       1 atg tca cat gat ccg atc gct gcc gac att ggc acg caa gtg agc gac       163
Met Ser His Asp Pro Ile Ala Ala Asp Ile Gly Thr Gln Val Ser Asp
  5                  10                  15 aac gct ctg cac ggc gtg acg gcc ggc tcg acg gcg ctg acg tcg gtg       211
Asn Ala Leu His Gly Val Thr Ala Gly Ser Thr Ala Leu Thr Ser Val
 20                  25                  30                  35 acc ggg ctg gtt ccc gcg ggg gcc gat gag gtc tcc gcc caa gcg gcg       259
Thr Gly Leu Val Pro Ala Gly Ala Asp Glu Val Ser Ala Gln Ala Ala
             40                  45                  50 acg gcg ttc aca tcg gag ggc atc caa ttg ctg gct tcc aat gca tcg       307
Thr Ala Phe Thr Ser Glu Gly Ile Gln Leu Leu Ala Ser Asn Ala Ser
         55                  60                  65 gcc caa gac cag ctc cac cgt gcg ggc gaa gcg gtc cag gac gtc gcc       355
```

```
Ala Gln Asp Gln Leu His Arg Ala Gly Glu Ala Val Gln Asp Val Ala
         70                  75                  80 cgc acc tat tcg caa atc gac gac ggc gcc gcc ggc gtc ttc gcc taata      405
Arg Thr Tyr Ser Gln Ile Asp Asp Gly Ala Ala Gly Val Phe Ala
         85                  90                  95 ggcccccaac acatcggagg gagtgatcac catgctgtgg cacgc                      450

<210> SEQ ID NO 88
<211> LENGTH: 98
<212> TYPE: PRT
<213> ORGANISM: Mycobacterium tuberculosis

<400> SEQUENCE: 88

Met Glu Lys Met Ser His Asp Pro Ile Ala Ala Asp Ile Gly Thr Gln
 1               5                  10                  15

Val Ser Asp Asn Ala Leu His Gly Val Thr Ala Gly Ser Thr Ala Leu
                20                  25                  30

Thr Ser Val Thr Gly Leu Val Pro Ala Gly Ala Asp Glu Val Ser Ala
         35                  40                  45

Gln Ala Ala Thr Ala Phe Thr Ser Glu Gly Ile Gln Leu Leu Ala Ser
     50                  55                  60

Asn Ala Ser Ala Gln Asp Gln Leu His Arg Ala Gly Glu Ala Val Gln
 65                  70                  75                  80

Asp Val Ala Arg Thr Tyr Ser Gln Ile Asp Asp Gly Ala Ala Gly Val
                 85                  90                  95

Phe Ala

<210> SEQ ID NO 89
<400> SEQUENCE: 89

000

<210> SEQ ID NO 90
<400> SEQUENCE: 90

000

<210> SEQ ID NO 91
<400> SEQUENCE: 91

000

<210> SEQ ID NO 92
<400> SEQUENCE: 92

000

<210> SEQ ID NO 93
<400> SEQUENCE: 93

000

<210> SEQ ID NO 94
<400> SEQUENCE: 94

000
```

```
<210> SEQ ID NO 95
<400> SEQUENCE: 95
000

<210> SEQ ID NO 96
<400> SEQUENCE: 96
000

<210> SEQ ID NO 97
<400> SEQUENCE: 97
000

<210> SEQ ID NO 98
<400> SEQUENCE: 98
000

<210> SEQ ID NO 99
<400> SEQUENCE: 99
000

<210> SEQ ID NO 100
<400> SEQUENCE: 100
000

<210> SEQ ID NO 101
<400> SEQUENCE: 101
000

<210> SEQ ID NO 102
<400> SEQUENCE: 102
000

<210> SEQ ID NO 103
<400> SEQUENCE: 103
000

<210> SEQ ID NO 104
<400> SEQUENCE: 104
000

<210> SEQ ID NO 105
<400> SEQUENCE: 105
000

<210> SEQ ID NO 106
<400> SEQUENCE: 106
```

000

<210> SEQ ID NO 107
<400> SEQUENCE: 107
000

<210> SEQ ID NO 108
<400> SEQUENCE: 108
000

<210> SEQ ID NO 109
<400> SEQUENCE: 109
000

<210> SEQ ID NO 110
<400> SEQUENCE: 110
000

<210> SEQ ID NO 111
<400> SEQUENCE: 111
000

<210> SEQ ID NO 112
<400> SEQUENCE: 112
000

<210> SEQ ID NO 113
<400> SEQUENCE: 113
000

<210> SEQ ID NO 114
<400> SEQUENCE: 114
000

<210> SEQ ID NO 115
<400> SEQUENCE: 115
000

<210> SEQ ID NO 116
<400> SEQUENCE: 116
000

<210> SEQ ID NO 117
<400> SEQUENCE: 117
000

```
<210> SEQ ID NO 118
<400> SEQUENCE: 118
000

<210> SEQ ID NO 119
<400> SEQUENCE: 119
000

<210> SEQ ID NO 120
<400> SEQUENCE: 120
000

<210> SEQ ID NO 121
<400> SEQUENCE: 121
000

<210> SEQ ID NO 122
<400> SEQUENCE: 122
000

<210> SEQ ID NO 123
<400> SEQUENCE: 123
000

<210> SEQ ID NO 124
<400> SEQUENCE: 124
000

<210> SEQ ID NO 125
<400> SEQUENCE: 125
000

<210> SEQ ID NO 126
<400> SEQUENCE: 126
000

<210> SEQ ID NO 127
<400> SEQUENCE: 127
000

<210> SEQ ID NO 128
<400> SEQUENCE: 128
000

<210> SEQ ID NO 129
```

<400> SEQUENCE: 129

000

<210> SEQ ID NO 130
<400> SEQUENCE: 130

000

<210> SEQ ID NO 131
<400> SEQUENCE: 131

000

<210> SEQ ID NO 132
<400> SEQUENCE: 132

000

<210> SEQ ID NO 133
<400> SEQUENCE: 133

000

<210> SEQ ID NO 134
<400> SEQUENCE: 134

000

<210> SEQ ID NO 135
<400> SEQUENCE: 135

000

<210> SEQ ID NO 136
<400> SEQUENCE: 136

000

<210> SEQ ID NO 137
<400> SEQUENCE: 137

000

<210> SEQ ID NO 138
<400> SEQUENCE: 138

000

<210> SEQ ID NO 139
<400> SEQUENCE: 139

000

<210> SEQ ID NO 140
<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148
<211> LENGTH: 540
<212> TYPE: DNA
<213> ORGANISM: Mycobacterium tuberculosis
<220> FEATURE:
<221> NAME/KEY: CDS
<222> LOCATION: (105)...(491)

<400> SEQUENCE: 148

```
atcgtgtcgt atcgagaacc ccggccggta tcagaacgcg ccagagcgca aacctttata     60
acttcgtgtc ccaaatgtga cgaccatgga ccaaggttcc tgag atg aac cta cgg     116
                                                 Met Asn Leu Arg
                                                   1 cgc cat cag acc ctg acg ctg cga ctg ctg gcg gca tcc gcg ggc att      164
Arg His Gln Thr Leu Thr Leu Arg Leu Leu Ala Ala Ser Ala Gly Ile
  5                  10                  15                  20 ctc agc gcc gcg gcc ttc gcc gcg cca gca cag gca aac ccc gtc gac      212
Leu Ser Ala Ala Ala Phe Ala Ala Pro Ala Gln Ala Asn Pro Val Asp
                 25                  30                  35 gac gcg ttc atc gcc gcg ctg aac aat gcc ggc gtc aac tac ggc gat      260
Asp Ala Phe Ile Ala Ala Leu Asn Asn Ala Gly Val Asn Tyr Gly Asp
             40                  45                  50 ccg gtc gac gcc aaa gcg ctg ggt cag tcc gtc tgc ccg atc ctg gcc      308
```

```
Pro Val Asp Ala Lys Ala Leu Gly Gln Ser Val Cys Pro Ile Leu Ala
         55                  60                  65 gag ccc ggc ggg tcg ttt aac acc gcg gta gcc agc gtt gtg gcg cgc       356
Glu Pro Gly Gly Ser Phe Asn Thr Ala Val Ala Ser Val Val Ala Arg
 70                  75                  80 gcc caa ggc atg tcc cag gac atg gcg caa acc ttc acc agt atc gcg       404
Ala Gln Gly Met Ser Gln Asp Met Ala Gln Thr Phe Thr Ser Ile Ala
 85                  90                  95                 100 att tcg atg tac tgc ccc tcg gtg atg gca gac gtc gcc agc ggc aac       452
Ile Ser Met Tyr Cys Pro Ser Val Met Ala Asp Val Ala Ser Gly Asn
                105                 110                 115 ctg ccg gcc ctg cca gac atg ccg ggg ctg ccc ggg tcc taggcgtgcg cg     503
Leu Pro Ala Leu Pro Asp Met Pro Gly Leu Pro Gly Ser
            120                 125 gctcctagcc ggtccctaac ggatcgatcg tggatgc                              540
```

<210> SEQ ID NO 149
<211> LENGTH: 129
<212> TYPE: PRT
<213> ORGANISM: Mycobacterium tuberculosis

<400> SEQUENCE: 149

```
Met Asn Leu Arg Arg His Gln Thr Leu Thr Leu Arg Leu Leu Ala Ala
 1               5                  10                  15

Ser Ala Gly Ile Leu Ser Ala Ala Ala Phe Ala Ala Pro Ala Gln Ala
                20                  25                  30

Asn Pro Val Asp Asp Ala Phe Ile Ala Ala Leu Asn Asn Ala Gly Val
            35                  40                  45

Asn Tyr Gly Asp Pro Val Asp Ala Lys Ala Leu Gly Gln Ser Val Cys
        50                  55                  60

Pro Ile Leu Ala Glu Pro Gly Gly Ser Phe Asn Thr Ala Val Ala Ser
 65                  70                  75                  80

Val Val Ala Arg Ala Gln Gly Met Ser Gln Asp Met Ala Gln Thr Phe
                85                  90                  95

Thr Ser Ile Ala Ile Ser Met Tyr Cys Pro Ser Val Met Ala Asp Val
            100                 105                 110

Ala Ser Gly Asn Leu Pro Ala Leu Pro Asp Met Pro Gly Leu Pro Gly
        115                 120                 125

Ser
```

<210> SEQ ID NO 150
<211> LENGTH: 15
<212> TYPE: PRT
<213> ORGANISM: Artificial Sequence
<220> FEATURE:
<223> OTHER INFORMATION: N-terminal sequence of CFP21
<220> FEATURE:
<221> NAME/KEY: MISC_FEATURE
<222> LOCATION: (3)..(3)
<223> OTHER INFORMATION: Xaa = any amino acid, unknown, or other

<400> SEQUENCE: 150

```
Asp Pro Xaa Ser Asp Ile Ala Val Val Phe Ala Arg Gly Thr His
 1               5                  10                  15
```

<210> SEQ ID NO 151
<211> LENGTH: 26
<212> TYPE: DNA
<213> ORGANISM: Artificial Sequence
<220> FEATURE:
<223> OTHER INFORMATION: OPBR-55 primer used for cloning of CFP21

```
<400> SEQUENCE: 151
acagatctgc gcatgcggat ccgtgt                                          26

<210> SEQ ID NO 152
<211> LENGTH: 28
<212> TYPE: DNA
<213> ORGANISM: Artificial Sequence
<220> FEATURE:
<223> OTHER INFORMATION: OPBR-56 primer used for cloning of CFP21

<400> SEQUENCE: 152
ttttccatgg tcatccggcg tgatcgag                                        28

<210> SEQ ID NO 153
<211> LENGTH: 25
<212> TYPE: DNA
<213> ORGANISM: Artificial Sequence
<220> FEATURE:
<223> OTHER INFORMATION: Sense oligonucleotide of RD1-ORF3f

<400> SEQUENCE: 153
cttcccggga tggaaaaaat gtcac                                           25

<210> SEQ ID NO 154
<211> LENGTH: 28
<212> TYPE: DNA
<213> ORGANISM: Artificial Sequence
<220> FEATURE:
<223> OTHER INFORMATION: Antisense oligonucleotide of RD1-ORF3r

<400> SEQUENCE: 154
gatgccatgg ttaggcgaag acgccggc                                        28

<210> SEQ ID NO 155
<211> LENGTH: 15
<212> TYPE: PRT
<213> ORGANISM: Artificial Sequence
<220> FEATURE:
<223> OTHER INFORMATION: N-terminal sequence of CFP8A

<400> SEQUENCE: 155

Asp Pro Val Asp Asp Ala Phe Ile Ala Lys Leu Asn Thr Ala Gly
 1               5                  10                  15

<210> SEQ ID NO 156
<211> LENGTH: 15
<212> TYPE: PRT
<213> ORGANISM: Artificial Sequence
<220> FEATURE:
<223> OTHER INFORMATION: N-terminal sequence of CFP16

<400> SEQUENCE: 156

Ala Lys Leu Ser Thr Asp Glu Leu Leu Asp Ala Phe Lys Glu Met
 1               5                  10                  15

<210> SEQ ID NO 157
<211> LENGTH: 25
<212> TYPE: DNA
<213> ORGANISM: Artificial Sequence
<220> FEATURE:
<223> OTHER INFORMATION: Gene specific primer CFP8A-F used for cloning
      of the individual antigens

<400> SEQUENCE: 157
ctgagatcta tgaacctacg gcgcc                                           25
```

```
<210> SEQ ID NO 158
<211> LENGTH: 35
<212> TYPE: DNA
<213> ORGANISM: Artificial Sequence
<220> FEATURE:
<223> OTHER INFORMATION: Gene specific primer CFP8A-R used for cloning
      of the individual antigens

<400> SEQUENCE: 158
ctcccatggt accctaggac ccgggcagcc ccggc                              35

<210> SEQ ID NO 159
<211> LENGTH: 33
<212> TYPE: DNA
<213> ORGANISM: Artificial Sequence
<220> FEATURE:
<223> OTHER INFORMATION: Gene specific primer OPBR-104 used for cloning
      of the individual antigens

<400> SEQUENCE: 159
ccgggagatc tatggcaaag ctctccaccg acg                                33

<210> SEQ ID NO 160
<211> LENGTH: 32
<212> TYPE: DNA
<213> ORGANISM: Artificial Sequence
<220> FEATURE:
<223> OTHER INFORMATION: Gene specific primer OPBR-105 used for cloning
      of the individual antigens

<400> SEQUENCE: 160
cgctgggcag agctacttga cggtgacggt gg                                 32

<210> SEQ ID NO 161
<211> LENGTH: 28
<212> TYPE: DNA
<213> ORGANISM: Artificial Sequence
<220> FEATURE:
<223> OTHER INFORMATION: Gene specific primer OPBR-86 used for cloning
      of the individual antigens

<400> SEQUENCE: 161
ccttgggaga tctttggacc ccggttgc                                      28

<210> SEQ ID NO 162
<211> LENGTH: 25
<212> TYPE: DNA
<213> ORGANISM: Artificial Sequence
<220> FEATURE:
<223> OTHER INFORMATION: Gene specific primer OPBR-87 used for cloning
      of the individual antigens

<400> SEQUENCE: 162
gacgagatct tatgggctta ctgac                                         25

<210> SEQ ID NO 163
<211> LENGTH: 15
<212> TYPE: PRT
<213> ORGANISM: Artificial Sequence
<220> FEATURE:
<223> OTHER INFORMATION: N-terminal sequence of TB15A
<220> FEATURE:
<221> NAME/KEY: MISC_FEATURE
<222> LOCATION: (13)..(15)
<223> OTHER INFORMATION: any Xaa = any amino acid, unknown, or other

<400> SEQUENCE: 163

Ser Ala Tyr Lys Thr Val Val Val Gly Thr Asp Asp Xaa Ser Xaa
1               5                   10                  15
```

<210> SEQ ID NO 164
<211> LENGTH: 15
<212> TYPE: PRT
<213> ORGANISM: Artificial Sequence
<220> FEATURE:
<223> OTHER INFORMATION: N-terminal sequence of TB16

<400> SEQUENCE: 164

Ala Asp Lys Thr Thr Gln Thr Ile Tyr Ile Asp Ala Asp Pro Gly
1               5                   10                  15

<210> SEQ ID NO 165
<211> LENGTH: 14
<212> TYPE: PRT
<213> ORGANISM: Artificial Sequence
<220> FEATURE:
<223> OTHER INFORMATION: N-terminal sequence of TB32

<400> SEQUENCE: 165

Ser Gly Asn Ser Ser Leu Gly Ile Ile Val Gly Ile Asp Asp
1               5                   10

<210> SEQ ID NO 166
<211> LENGTH: 15
<212> TYPE: PRT
<213> ORGANISM: Artificial Sequence
<220> FEATURE:
<223> OTHER INFORMATION: N-terminal sequence of TB51

<400> SEQUENCE: 166

Met Lys Ser Thr Val Glu Gln Leu Ser Pro Thr Arg Val Arg Ile
1               5                   10                  15

<210> SEQ ID NO 167
<211> LENGTH: 28
<212> TYPE: DNA
<213> ORGANISM: Artificial Sequence
<220> FEATURE:
<223> OTHER INFORMATION: Primer TB15A-F used for cloning of TB15A

<400> SEQUENCE: 167
ctgccatggc taggtggtgt gcacgatc                                      28

<210> SEQ ID NO 168
<211> LENGTH: 27
<212> TYPE: DNA
<213> ORGANISM: Artificial Sequence
<220> FEATURE:
<223> OTHER INFORMATION: Primer TB15A-R used for cloning of TB15A

<400> SEQUENCE: 168
ctgaagctta tgagcgccta taagacc                                       27

<210> SEQ ID NO 169
<211> LENGTH: 27
<212> TYPE: DNA
<213> ORGANISM: Artificial Sequence
<220> FEATURE:
<223> OTHER INFORMATION: Primer TB16A-F used for cloning of TB16

<400> SEQUENCE: 169
ctgagatctg cggacaagac gacacag                                       27

<210> SEQ ID NO 170
<211> LENGTH: 27
<212> TYPE: DNA

```
<213> ORGANISM: Artificial Sequence
<220> FEATURE:
<223> OTHER INFORMATION: Primer TB16A-R used for cloning of TB16

<400> SEQUENCE: 170
ctcccatggt accggaatca ctcagcc                                      27

<210> SEQ ID NO 171
<211> LENGTH: 27
<212> TYPE: DNA
<213> ORGANISM: Artificial Sequence
<220> FEATURE:
<223> OTHER INFORMATION: Primer TB32-F used for cloning TB32

<400> SEQUENCE: 171
ctgagatcta tgtcatcggg caattca                                      27

<210> SEQ ID NO 172
<211> LENGTH: 31
<212> TYPE: DNA
<213> ORGANISM: Artificial Sequence
<220> FEATURE:
<223> OTHER INFORMATION: Primer TB32-R used for cloning TB32

<400> SEQUENCE: 172
ctcccatggc tacctaagtc agcgactcgc g                                 31

<210> SEQ ID NO 173
<211> LENGTH: 27
<212> TYPE: DNA
<213> ORGANISM: Artificial Sequence
<220> FEATURE:
<223> OTHER INFORMATION: Primer TB51-F used for cloning TB51

<400> SEQUENCE: 173
ctgagatctg tgaagagcac cgtcgag                                      27

<210> SEQ ID NO 174
<211> LENGTH: 27
<212> TYPE: DNA
<213> ORGANISM: Artificial Sequence
<220> FEATURE:
<223> OTHER INFORMATION: Primer TB32-R used for cloning TB32

<400> SEQUENCE: 174
ctcccatggg tcatacggtc acgttgt                                      27
```

TB DIAGNOSTIC BASED ON ANTIGENS FROM M. TUBERCULOSIS

This application is a continuation application of now abandoned U.S. patent application Ser. No. 11/196,018, filed Aug. 2, 2005, which is a divisional of:

U.S. application Ser. No. 10/138,473, filed on May 2, 2002 now U.S. Pat. No. 6,982,085, which is a continuation-in-part of U.S. patent application Ser. No. 10/060,428, filed Jan. 29, 2002 now abandoned, which is a continuation-in-part of U.S. application Ser. No. 09/415,884, filed Oct. 8, 1999 now abandoned, which is a non-provisional of U.S. Application No. 60/116,673, filed Jan. 21, 1999, which claims priority to U.S. patent application Ser. No. 09/050,739, filed 30 Mar. 1998, which claims priority from U.S. Provisional Application No. 60/044,624, filed 18 Apr. 1997, U.S. Provisional Application No. 60/070,488, filed 5 Jan. 1998, and Danish Patent Applications Nos. DK 1997 00376, filed 2 Apr. 1997, and DK 1997 01277, filed 10 Nov. 1997;

U.S. patent application Ser. No. 09/791,171, filed 20 Feb. 2001, which is a divisional of the above mentioned U.S. patent application Ser. No. 09/050,739, claiming the same priorities; and U.S. patent application Ser. No. 09/415,884, filed 8 Oct. 1999, which claims priority from U.S. Provisional Application No. 60/116,673, filed 21 Jan. 1999 and Danish Patent Application No. DK 1998 01281, filed 8 Oct. 1998.

Each of these patent applications as well as all documents cited in the text of this application, and references cited in the documents referred to in this application (including references cited in the aforementioned patent applications or during their prosecution) are hereby incorporated herein by reference and for which priority is claimed under 35 U.S.C. §120.

FIELD OF INVENTION

The present invention relates to a number of immunologically active, novel polypeptide fragments derived from *Mycobacterium tuberculosis*, diagnostics and other immunologic compositions containing the fragments as immunogenic components, and methods of production and use of the polypeptides. The invention also relates to novel nucleic acid fragments derived from *M. tuberculosis* which are useful in the preparation of the polypeptide fragments of the invention or in the diagnosis of infection with *M. tuberculosis*. The invention further relates to certain fusion polypeptides.

GENERAL BACKGROUND

Human tuberculosis caused by *Mycobacterium tuberculosis* (*M. tuberculosis*) is a severe global health problem, responsible for approx. 3 million deaths annually, according to the WHO. The worldwide incidence of new tuberculosis (TB) cases had been falling during the 1960s and 1970s but during recent years this trend has markedly changed in part due to the advent of AIDS and the appearance of multidrug resistant strains of *M. tuberculosis*.

In 1998 Cole et al published the complete genome sequence of *M. tuberculosis* and predicted the presence of approximately 4000 open reading frames (Cole et al 1998). Nucleotide sequences are described, and putative protein sequences. However importantly, this sequence information cannot be used to predict if the DNA is translated and expressed as proteins in vivo. More importantly, it is not possible on the basis of the sequences, to predict whether a given sequence will encode an immunogenic or an inactive protein. The only way to determine if a protein is recognized by the immune system during or after an infection with *M. tuberculosis* is to produce the given protein and test it in an appropriate assay as described herein.

Short term-culture filtrate (ST-CF) is a complex mixture of proteins released from *M. tuberculosis* during the first few days of growth in a liquid medium (Andersen et al., 1991). Culture filtrates has been suggested to hold protective antigens recognized by the host in the first phase of TB infection (Andersen et al. 1991, Orme et al. 1993). Recent data from several laboratories have demonstrated that experimental subunit vaccines based on culture filtrate antigens can provide high levels of acquired resistance to TB (Pal and Horwitz, 1992; Roberts et al., 1995; Andersen, 1994; Lindblad et al., 1997). Culture filtrates are, however, complex protein mixtures and until now very limited information has been available on the molecules responsible for this protective immune response.

It is thus an object of the present invention to provide a composition for the determination of an immune response against a virulent *Mycobacterium* such as a diagnostic reagent for the diagnosis of an infection with a virulent *Mycobacterium*.

SUMMARY OF THE INVENTION

The present invention is i.a. based on the identification and characterization of a number of previously uncharacterized culture filtrate antigens from *M. tuberculosis*. In animal models of TB, T cells mediating immunity are focused predominantly to antigens in the regions 6-12 and 17-30 kDa of STCF. In the present invention 8 antigens in the low molecular weight region (CFP7, CFP7A, CFP7B, CFP8A, CFP8B, CFP9, CFP10A, and CFP11) and 18 antigens (CFP16, CFP17, CFP19, CFP19B, CFP20, CFP21, CFP22, CFP22A, CFP23, CFP23A, CFP23B, CFP25, CFP26, CFP27, CFP28, CFP29, CFP30A, and CFP30B) in the 17-30 kDa region have been identified.

Finally, the invention is based on the surprising discovery that fusions between ESAT-6 and MPT59 are superior immunogens compared to the unfused proteins, respectively.

The following table lists the antigens of the invention by the names used herein as well as by reference to relevant SEQ ID NOs of N-terminal sequences, full amino acid sequences and sequences of DNA encoding the antigens:

| Antigen | N-terminal sequence SEQ ID NO: | Nucleotide sequence SEQ ID NO: | Amino acid sequence SEQ ID NO: |
|---|---|---|---|
| CFP7 | | 1 | 2 |

It is well-known in the art that T-cell epitopes are responsible for the elicitation of the acquired immunity against TB, whereas B-cell epitopes are without any significant influence on acquired immunity and recognition of mycobacteria in vivo. Since such T-cell epitopes are linear and are known to have a minimum length of 6 amino acid residues, the present invention is especially concerned with the identification and utilisation of such T-cell epitopes.

Hence, in its broadest aspect the invention relates to a substantially pure polypeptide fragment which
a) comprises an amino acid sequence selected from the sequences shown in SEQ ID NO: 2,
b) comprises a subsequence of the polypeptide fragment defined in a) which has a length of at least 6 amino acid residues, said subsequence being immunologically equivalent to the polypeptide defined in a) with respect to the ability of evoking a protective immune response against infections with mycobacteria belonging to the tuberculosis complex or with respect to the ability of eliciting a diagnostically significant immune response indicating previous or ongoing sensitization with antigens derived from mycobacteria belonging to the tuberculosis complex, or
c) comprises an amino acid sequence having a sequence identity with the polypeptide defined in a) or the subsequence defined in b) of at least 70% and at the same time being immunologically equivalent to the polypeptide defined in a) with respect to the ability of evoking a protective immune response against infections with mycobacteria belonging to the tuberculosis complex or with respect to the ability of eliciting a diagnostically significant immune response indicating previous or ongoing sensitization with antigens derived from mycobacteria belonging to the tuberculosis complex, with the proviso that
i) the polypeptide fragment is in essentially pure form when consisting of the amino acid sequence 1-96 of SEQ ID NO: 2,
ii) the degree of sequence identity in c) is at least 95% when the polypeptide comprises a homologue of a polypeptide which has the amino acid sequence SEQ ID NO: 2 or a subsequence thereof as defined in b), and Other parts of the invention pertains to the DNA fragments encoding a polypeptide with the above definition as well as to DNA fragments useful for determining the presence of DNA encoding such polypeptides has a length of at least 10 nucleotides and hybridizes readily under stringent hybridization conditions.

It is surprisingly demonstrated herein that several polypeptides isolated from the cell wall, cell membrane or cytosol and short term culture filtrate (STCF) are recognized by human tuberculosis antisera.

Therefore it is considered likely that these polypeptides, either alone or in combination, can be useful as diagnostic reagents in the diagnosis of tuberculosis.

The present inventors contemplate that in order to achieve a very high sensitivity for a serodiagnostic TB reagent it is important to combine two or more TB antigens, or alternatively, to use recombinant fusions proteins comprising at least two proteins or B cell epitopes. The antibody response of tuberculosis is heterogeneous with considerable person-to-person variance to which antigens that are recognized by the antibodies and therefore it can be an advantage to use combinations of proteins (e.g. in protein cocktails) which may increase the sensitivity and be recognized by sera from a high proportion of infected individuals. Especially, it is advantageous to combine from two to four antigens which will give a higher sensitivity than the single antigen and still a high specificity (more than 90%).

Thus, the invention is related to detection of infections caused by species of the tuberculosis complex (*M. tuberculosis, M. bovis, M. africanum*) by the use of a combination of two or more polypeptides comprising a *M. tuberculosis* antigen or an immunogenic portion or other variant thereof, or by the use of two or more DNA sequences encoding a *M. tuberculosis* antigen or an immunogenic portion or other variant thereof.

DETAILED DISCLOSURE OF THE INVENTION

The invention relates to polypeptides which induce specific antibody responses in a TB patient as determined by an ELISA technique or a western blot when the whole blood is diluted 1:20 in PBS and stimulated with the polypeptide in a concentration of at the most 20 μg/ml and induces an OD of at least 0.1 in ELISA, or a visual response in western blot.

Any polypeptide fulfilling the above property and which is obtainable from either the cell wall, cell membrane, the cytosol or STCF of the tuberculosis complex is within the scope of the present invention.

In an important embodiment, the invention relates to a composition comprising a combination of two or more (e.g. 2, 3, 4, 5, 6, 7 or more) substantially pure polypeptides, which comprises one or more amino acid sequences selected from (a) Rv0652, Rv2462c, Rv1984c, Rv2185c, Rv1636, Rv3451, Rv3872, Rv3354 and Rv2623

(b) an immunogenic portion of any one of the sequences in (a); and/or (c) an amino acid sequence analogue having at least 70% sequence identity to any one of the sequences in (a) or (b) and at the same time being immunogenic;

for use as a pharmaceutical or diagnostic reagent.

Also, the invention relates to a composition comprising one or more fusion polypeptides, which comprises one or more amino acid sequences selected from (a) Rv0652, Rv2462c, Rv1984c, Rv2185c, Rv1636, Rv3451, Rv3872, Rv3354 and Rv2623

(b) an immunogenic portion of any one of the sequences in (a); and/or (c) an amino acid sequence analogue having at least 70% sequence identity to any one of the sequences in (a) or (b) and at the same time being immunogenic;

and at least one fusion partner.

The fusion partner comprises preferably a polypeptide fragment selected from (a) a polypeptide fragment derived from a virulent mycobacterium, such as ESAT-6, MPB64, MPT64, TB10.4, CFP10, RD1-ORF5, RD1-ORF2, Rv1036, Ag85A, Ag85B, Ag85C, 19 kDa lipoprotein, MPT32, MPB59 and alpha-crystallin;

(b) a polypeptide as defined above; and/or (c) at least one immunogenic portion of any of such polypeptides in (a) or (b).

In another embodiment, the invention relates to an immunogenic composition comprising a composition according to the invention.

In a further embodiment, the invention relates to the use of a composition as defined above for the preparation of a pharmaceutical composition, e.g. for diagnosis of tuberculosis caused by virulent mycobacteria, e.g. by *Mycobacterium tuberculosis, Mycobacterium africanum* or *Mycobacterium bovis.*

In a still further embodiment, the invention relates to a diagnostic tool comprising a combination of two or more substantially pure polypeptides, which comprises one or more amino acid sequences selected from (a) Rv0652, Rv2462c, Rv1984c, Rv2185c, Rv1636, Rv3451, Rv3872, Rv3354 and Rv2623

(b) an immunogenic portion of any one of the sequences in (a); and/or (c) an amino acid sequence analogue having at least 70% sequence identity to any one of the sequences in (a) or (b) and at the same time being immunogenic Also, the invention relates to a substantially pure polypeptide, which comprises an amino acid sequence selected from (a) Rv0652, Rv2462c, Rv1984c, Rv2185c, Rv1636, Rv3451, Rv3872, Rv3354 and Rv2623
(b) an immunogenic portion of any one of the sequences in (a); and/or
(c) an amino acid sequence analogue having at least 70% sequence identity to any one of the sequences in (a) or (b) and at the same time being immunogenic
for use in preparing a composition according to the invention or a diagnostic tool according to the invention.

The polypeptide fragments of the invention preferably comprises an amino acid sequence of at least 6 amino acid residues in length which has a higher sequence identity than 70 percent with SEQ ID NO: 2. A preferred minimum percentage of sequence identity is at least 80%, such as at least 85%, at least 90%, at least 91%, at least 92%, at least 93%, at least 94%, at least 95%, at least 96%, at least 97%, at least 98%, at least 99%, and at least 99.5%.

In a further embodiment, the invention relates to a nucleic acid fragments in isolated form which
(a) comprises one or more nucleic acid sequences which encodes a polypeptide as defined above, or comprises a nucleic acid sequence complementary thereto; or
(b) has a length of at least 10 nucleotides and hybridizes readily under stringent hybridization conditions with a nucleotide sequence selected from Rv0652, Rv2462c, Rv1984c, Rv2185c, Rv1636, Rv3451, Rv3872, Rv3354 and Rv2623 nucleotide sequences or a sequence complementary thereto, or with a nucleotide sequence selected from a sequence in (a).

The nucleic acid fragment is preferably a DNA fragment.

It is preferred that the nucleic acid fragment is a DNA fragment.

It is preferred that the nucleic acid fragment is longer than 10 nucleotides, such as at least 15, at least 20, at least 25, at least 30, at least 35, at least 40, at least 45, at least 50, at least 55, at least 60, at least 65, at least 70, and at least 80 nucleotides long, and the sequence identity should preferable also be higher than 70%, such as higher than 70%, such as at least 75%, at least 80%, at least 85%, at least 90%, at least 92%, at least 94%, at least 96%, and at least 98%. It is most preferred that the sequence identity is 100%.

In another embodiment, the invention relates to the use of a nucleic acid fragment according to the invention for the preparation of a composition for the diagnosis of tuberculosis caused by virulent mycobacteria, e.g. by *Mycobacterium tuberculosis*, *Mycobacterium africanum* or *Mycobacterium bovis*.

The invention also relates to a replicable expression vector, which comprises a nucleic acid, fragment according to the invention, and to a transformed cell harbouring at least one such vector.

In another embodiment, the invention relates to a method for producing a polypeptide according to the invention, comprising
(a) inserting a nucleic acid fragment according to the invention into a vector which is able to replicate in a host cell, introducing the resulting recombinant vector into the host cell, culturing the host cell in a culture medium under conditions sufficient to effect expression of the polypeptide, and recovering the polypeptide from the host cell or culture medium;
(b) isolating the polypeptide from a whole mycobacterium, e.g. *Mycobacterium tuberculosis*, *Mycobacterium africanum* or *Mycobacterium bovis*, from culture filtrate or from lysates or fractions thereof; or
(c) synthesizing the polypeptide e.g. by solid or liquid phase peptide synthesis.

In a preferred embodiment of the invention, the polypeptide fragment of the invention comprises an epitope for a T-helper cell.

The invention also relates to a method of diagnosing tuberculosis caused by virulent mycobacteria, e.g. by *Mycobacterium tuberculosis*, *Mycobacterium africanum* or *Mycobacterium bovis*, in an animal, including a human being, comprising intradermally injecting, in the animal, a composition according to the invention, a positive skin response at the location of injection being indicative of the animal having tuberculosis, and a negative skin response at the location of injection being indicative of the animal not having tuberculosis.

A monoclonal or polyclonal antibody, which is specifically reacting with a polypeptide according to the invention in an immuno assay, or a specific binding fragment of said antibody for use as a diagnostic reagent, is also a part of the invention.

In line with the disclosure above pertaining to vaccine preparation and use, the invention also pertains to a method for immunising an animal, including a human being, against TB caused by mycobacteria belonging to the tuberculosis complex, comprising administering to the animal the polypeptide of the invention, or a vaccine composition of the invention as described above, or a living vaccine described above. Preferred routes of administration are the parenteral (such as intravenous and intraarterially), intraperitoneal, intramuscular, subcutaneous, intradermal, oral, buccal, sublingual, nasal, rectal or transdermal route.

the sample from the animal with the polypeptide of the invention, a significant release into the extracellular phase of at least one cytokine by mononuclear cells in the blood sample being indicative of the animal being sensitized. By the term "significant release" is herein meant that the release of the cytokine is significantly higher than the cytokine release polypeptide fragments of the invention and using well-known methods for visualizing the reaction between the antibody and antigen.

In a further embodiment, the invention relates to a method for diagnosing previous or ongoing infection with a virulent mycobacterium, said method comprising
(a) contacting a subject sample, e.g. a blood sample, with a composition according to the invention or a diagnostic tool according to the invention,
(b) detecting binding of an antibody, said binding being an indication that said subject is infected by *Mycobacterium tuberculosis* or is susceptible to *Mycobacterium tuberculosis* infection.

In an important embodiment, the invention relates to a serodiagnostic composition comprising a combination of two or more substantially pure polypeptides, which comprises one or more amino acid sequences selected from
(a) Rv0652, Rv2462c, Rv1984c, Rv2185c, Rv1636, Rv3451, Rv3872, Rv3354 and Rv2623;
(b) an immunogenic portion of any one of the sequences in (a); and/or
(c) an amino acid sequence analogue having at least 70% sequence identity to any one of the sequences in (a) or (b) and at the same time being immunogenic.

Thus, an important embodiment of the invention is a polypeptide fragment defined above which
1) induces a release of IFN-γ from primed memory T-lymphocytes withdrawn from a mouse within 2 weeks of primary infection or within 4 days after the mouse has been rechallenge infected with mycobacteria belonging to the tuberculosis complex, the induction performed by the addition of the polypeptide to a suspension comprising about 200,000 spleen cells per ml, the addition of the polypeptide resulting in a concentration of 1-4 .mu.g polypeptide per ml suspension, the release of IFN-.gamma. being assessable by determination of IFN-γ in supernatant harvested 2 days after the addition of the polypeptide to the suspension, and/or 2) induces a release of IFN-γ of at least 1,500 pg/ml above background level from about 1,000,000 human PBMC (peripheral blood mononuclear cells) per ml isolated from TB patients in the first phase of infection, or from healthy BCG vaccinated donors, or from healthy contacts to TB patients, the induction being performed by the addition of the polypeptide to a suspension comprising the about 1,000,000 PBMC per ml, the addition of the polypeptide resulting in a concentration of 1-4 .mu.g polypeptide per ml suspension, the release of IFN-gamma. being assessable by determination of IFN-.gamma. in supernatant harvested 2 days after the addition of the polypeptide to the suspension; and/or 3) induces an IFN-γ release from bovine PBMC derived from animals previously sensitized with mycobacteria belonging to the tuberculosis complex, said release being at least two times the release observed from bovine PBMC derived from animals not previously sensitized with mycobacteria belonging to the tuberculosis complex.

Hence, the invention also relates to a vaccine comprising a nucleic acid fragment according to the invention, the vaccine effecting in vivo expression of antigen by an animal, including a human being, to whom the vaccine has been administered, the amount of expressed antigen being effective to confer substantially increased resistance to infections with mycobacteria of the tuberculosis complex in an animal, including a human being.

Apart from their use as starting points for the synthesis of polypeptides of the invention and for hybridization probes (useful for direct hybridization assays or as primers in e.g. PCR or other molecular amplification methods) the nucleic acid fragments of the invention may be used for effecting in vivo expression of antigens, i.e. the nucleic acid fragments may be used in so-called DNA vaccines. Recent research have revealed that a DNA fragment cloned in a vector which is non-replicative in eukaryotic cells may be introduced into an animal (including a human being) by e.g. intramuscular injection or percutaneous administration (the so-called "gene gun" approach). The DNA is taken up by e.g. muscle cells and the gene of interest is expressed by a promoter which is functioning in eukaryotes, e.g. a viral promoter, and the gene product thereafter stimulates the immune system. These newly discovered methods are reviewed in Ulmer et al., 1993, which hereby is included by reference.

Hence, the invention also relates to a vaccine comprising a nucleic acid fragment according to the invention, the vaccine effecting in vivo expression of antigen by an animal, including a human being, to whom the vaccine has been administered, the amount of expressed antigen being effective to confer substantially increased resistance to infections with mycobacteria of the tuberculosis complex in an animal, including a human being.

Therefore, another important aspect of the present invention is an improvement of the living BCG vaccine presently available, which is a vaccine for immunizing an animal, including a human being, against TB caused by mycobacteria belonging to the tuberculosis-complex, comprising as the effective component a microorganism, wherein one or more copies of a DNA sequence encoding a polypeptide as defined above has been incorporated into the genome of the microorganism in a manner allowing the microorganism to express and secrete the polypeptide.

Throughout this specification, unless the context requires otherwise, the word "comprise", or variations thereof such as "comprises" or "comprising", will be understood to imply the inclusion of a stated element or integer or group of elements or integers but not the exclusion of any other element or integer or group of elements or integers.

By the term "a polypeptide" in the present application is generally understood a polypeptide of the invention, as will be described later. It is also within the meaning of "a polypeptide" that several polypeptides can be used, i.e. in the present context "a" means "at least one" unless explicitly indicated otherwise. The "polypeptide" is used to refer to short peptides with a length of at least two amino acid residues and at most 10 amino acid residues, oligopeptides (11-100 amino acid residues), and longer peptides (the usual interpretation of "polypeptide", i.e. more than 100 amino acid residues in length) as well as proteins (the functional entity comprising at least one peptide, oligopeptide, or polypeptide which may be chemically modified by being phosphorylated, glycosylated, by being lipidated, or by comprising prosthetic groups). The definition of polypeptides comprises native forms of peptides/proteins in *Mycobacteria* as well as recombinant proteins or peptides in any type of expression vectors transforming any kind of host, and also chemically synthesized polypeptides. Within the scope of the invention is a polypeptide which is at least 6 amino acids long, preferably 7, such as 8, 9, 10, 11, 12, 13, 14 amino acids long, preferably at least 15 amino acids, such as 15, 16, 17, 18, 19, 20 amino acids long. However, also longer polypeptides having a length of e.g. 25, 50, 75, 100, 125, 150, 175 or 200 amino acids are within the scope of the present invention.

In the present context the term "purified polypeptide" and substantially pure polypeptide fragment" means a polypeptide preparation which contains at most 5% by weight of other polypeptide material with which it is natively associated (lower percentages of other polypeptide material are preferred, e.g. at most 4%, at most 3%, at most 2%, at most 1%, and at most ½%). It is preferred that the substantially pure polypeptide is at least 96% pure, i.e. that the polypeptide constitutes at least 96% by weight of total polypeptide material present in the preparation, and higher percentages are preferred, such as at least 97%, at least 98%, at least 99%, at least 99.25%, at least 99.5%, and at least 99.75%. It is especially preferred that the polypeptide is in "essentially pure form", i.e. that the polypeptide is essentially free of any other antigen with which it is natively associated, i.e. free of any other antigen from bacteria belonging to the tuberculosis complex. This can be accomplished by preparing the polypeptide by means of recombinant methods in a non-mycobacterial host cell as will be described in detail below, or by synthesizing the polypeptide by the well-known methods of solid or liquid phase peptide synthesis, e.g. by the method described by Merrifield or variations thereof.

By the terms "somatic protein" or "protein derived from the cell wall, the cell membrane or the cytosol", or by the abbreviation "SPE" is understood a polypeptide or a protein extract obtainable from a cell or a part.

When referring to an "immunologically equivalent" polypeptide is herein meant that the polypeptide, when formulated in a vaccine or a diagnostic agent (i.e. together with a pharmaceutically acceptable carrier or vehicle and optionally an adjuvant), will I) confer, upon administration (either alone or as an immunologically active constituent together with other antigens), an acquired increased specific resistance in a mouse and/or in a quinea pig and/or in a primate such as a human being against infections with bacteria belonging to the tuberculosis complex by *Mycobacterium bovis* BCG and also at least 20% of the acquired increased resistance conferred by the parent polypeptide comprising SEQ ID NO: 2.

By the terms "culture filtrate protein", or by the abbreviation "STCF" is understood a complex mixture of proteins released from *M. tuberculosis* during the first few days of growth in a liquid medium.

By the term "non-naturally occurring polypeptide" is understood a polypeptide that does not occur naturally. This means that the polypeptide is substantially pure, and/or that the polypeptide has been synthesized in the laboratory, and/or that the polypeptide has been produced by means of recombinant technology.

The "tuberculosis-complex" has its usual meaning, i.e. the complex of mycobacteria causing TB which are *Mycobacterium tuberculosis, Mycobacterium bovis, Mycobacterium bovis* BCG, and *Mycobacterium africanum.*

By the term "virulent *Mycobacterium*" is understood a bacterium capable of causing the tuberculosis disease in a mammal including a human being. Examples of virulent *Mycobacteria* are *M. tuberculosis, M. africanum*, and *M. bovis.*

By "a TB patient" is understood an individual with culture or microscopically proven infection with virulent *Mycobacteria*, and/or an individual clinically diagnosed with TB and who is responsive to anti-TB chemotherapy. Culture, microscopy and clinical diagnosis of TB is well known by the person skilled in the art.

By the term "PPD positive individual" is understood an individual with a positive Mantoux test or an individual where PPD induces an increase in in vitro recall response determined by release of IFN-γ of at least 1,000 pg/ml from Peripheral Blood Mononuclear Cells (PBMC) or whole blood, the induction being performed by the addition of 2.5 to 5 μg PPD/ml to a suspension comprising about 1.0 to $2.5\times10^5$ PBMC, the release of IFN-γ being assessable by determination of IFN-γ in supernatant harvested 5 days after the addition of PPD to the suspension compared to the release of IFN-γ without the addition of PPD.

By the term "delayed type hypersensitivity reaction" is understood a T-cell mediated inflammatory response elicited after the injection of a polypeptide into or application to the skin, said inflammatory response appearing 72-96 hours after the polypeptide injection or application.

By the term "IFN-γ" is understood interferon-gamma.

By the terms "analogue" and "subsequence" when used in connection with polypeptides is meant any polypeptide having the same immunological characteristics as the polypeptides of the invention shown in any of SEQ ID NOs: 8, 30, 34, 38, 149, 64, 10 or 88. Thus, included is also a polypeptide from a different source, such as from another bacterium or even from a eukaryotic cell.

When referring to an "immunologically equivalent" polypeptide is herein meant that the polypeptide, when formulated in a diagnostic agent (i.e. together with a pharmaceutically acceptable carrier or vehicle and optionally an adjuvant), will elicit a diagnostically significant immune response in a mammal indicating previous or ongoing sensitization with antigens derived from mycobacteria belonging to the tuberculosis complex; this diagnostically significant immune response can be in the form of a delayed type hypersensitivity reaction which can e.g. be determined by a skin test, or a serological test. A diagnostically significant response in a skin test setup will be a reaction which gives rise to a skin reaction which is at least 5 mm in diameter and which is at least 65% (preferably at least 75% such as at the least 85%) of the skin reaction (assessed as the skin reaction diameter) elicited by the parent polypeptide comprising SEQ ID NO: 8, 30, 34, 38, 149, 64, 10 and 88.

When the term "nucleotide" is used in the following, it should be understood in the broadest sense. That is, most often the nucleotide should be considered as DNA. However, when DNA can be substituted with RNA, the term nucleotide should be read to include RNA embodiments which will be apparent for the person skilled in the art. For the purposes of hybridization, PNA or LNA may be used instead of DNA. PNA has been shown to exhibit a very dynamic hybridization profile and is described in Nielsen P E et al., 1991, Science 254: 1497-1500). LNA (Locked Nucleic Acids) is a recently introduced oligonucleotide analogue containing bicyclo nucleoside monomers (Koshkin et al., 1998, 54, 3607-3630; Nielsen, N. K. et al. J. Am. Chem. Soc 1998, 120, 5458-5463).

The term "stringent" when used in conjunction with hybridization conditions is as defined in the art, i.e. the hybridization is performed at a temperature not more than 15-20° C. under the melting point Tm, cf. Sambrook et al, 1989, pages 11.45-11.49. Preferably, the conditions are "highly stringent", i.e. 5-10° C. under the melting point Tm.

The terms "analogue" or "subsequence" when used in connection with the nucleotide fragments of the invention are thus intended to indicate a nucleotide sequence which encodes a polypeptide exhibiting identical or substantially identical immunological properties to a polypeptide encoded by the nucleotide fragment of the invention shown in any of SEQ ID NOs: 7, 29, 33, 37, 148, 63, 9 or 87 allowing for minor variations which do not have an adverse effect on the ligand binding properties and/or biological function and/or immunogenicity as compared to any of the polypeptides of the invention or which give interesting and useful novel binding properties or biological functions and immunogenicities etc. of the analogue and/or subsequence. The analogous nucleotide fragment or nucleotide sequence may be derived from a bacterium, a mammal, or a human or may be partially or completely of synthetic origin. The analogue and/or subsequence may also be derived through the use of recombinant nucleotide techniques.

The term "subsequence" when used in connection with the nucleic acid fragments of the invention is intended to indicate a continuous stretch of at least 10 nucleotides which exhibits the above hybridization pattern. Normally this will require a minimum sequence identity of at least 70% with a subsequence of the hybridization partner having SEQ ID NO: 7, 29, 33, 37, 148, 63, 9 or 87. It is preferred that the nucleic acid fragment is longer than 10 nucleotides, such as at least 15, at least 20, at least 25, at least 30, at least 35, at least 40, at least 45, at least 50, at least 55, at least 60, at least 65, at least 70, and at least 80 nucleotides long, and the sequence identity should preferable also be higher than 70%, such as at least 75%, at least 80%, at least 85%, at least 90%, at least 92%, at least 94%, at least 96%, and at least 98%. It is most preferred that the sequence identity is 100%. Such fragments may be readily prepared by, for example, directly synthesizing the fragment by chemical means, by application of nucleic acid reproduction technology, such as the PCR technology of U.S. Pat. No. 4,603,102, or by introducing selected sequences into recombinant vectors for recombinant production.

Furthermore, the terms "analogue" and "subsequence" are intended to allow for variations in the sequence such as substitution, insertion (including introns), addition, deletion and rearrangement of one or more nucleotides, which variations do not have any substantial effect on the polypeptide encoded by a nucleotide fragment or a subsequence thereof. The term "substitution" is intended to mean the replacement of one or more nucleotides in the full nucleotide sequence with one or more different nucleotides, "addition" is understood to mean the addition of one or more nucleotides at either end of the full nucleotide sequence, "insertion" is intended to mean the introduction of one or more nucleotides within the full nucleotide sequence, "deletion" is intended to indicate that one or more nucleotides have been deleted from the full nucleotide sequence whether at either end of the sequence or at any suitable point within it, and "rearrangement" is intended to mean that two or more nucleotide residues have been exchanged with each other.

It is well known that the same amino acid may be encoded by various codons, the codon usage being related, inter alia, to the preference of the organisms in question expressing the nucleotide sequence. Thus, at least one nucleotide or codon of a nucleotide fragment of the invention may be exchanged by others which, when expressed, results in a polypeptide identical or substantially identical to the polypeptide encoded by the nucleotide fragment in question.

The term "sequence identity" indicates a quantitative measure of the degree of homology between two amino acid sequences of equal length or between two nucleotide sequences of equal length. If the two sequences to be compared are not of equal length, they must be aligned to best possible fit. The sequence identity can be calculated as $$\frac{(N_{ref} - N_{dif})100}{N_{ref}},$$

wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}=2$ and $N_{ref}=8$). A gap is counted as non-identity of the specific residue(s), i.e. the DNA sequence AGTGTC will have a sequence identity of 75% with the DNA sequence AGTCAGTC ($N_{dif}=2$ and $N_{ref}=8$). Sequence identity can alternatively be calculated by the BLAST program e.g. the BLASTP program or the BLASTN program (Pearson W. R and D. J. Lipman (1988) PNAS USA 85:2444-2448) (www.ncbi.nlm.nih.gov/BLAST). In one aspect of the invention, alignment is performed with the global align algorithm with default parameters as described by X. Huang and W. Miller. Adv. Appl. Math. (1991) 12:337-357, available at http://www.ch.embnet.org/software/LALIGN_form.html.

The sequence identity is used here to illustrate the degree of identity between the amino acid sequence of a given polypeptide and the amino acid sequence shown in SEQ ID NO: 8, 30, 34, 38, 149, 64, 10 and 88. The amino acid sequence to be compared with the amino acid sequence shown in SEQ ID NO: 8, 30, 34, 38, 149, 64, 10 and 88 may be deduced from a DNA sequence, e.g. obtained by hybridization as defined below, or may be obtained by conventional amino acid sequencing methods. The sequence identity is preferably determined on the amino acid sequence of a mature polypeptide, i.e. without taking any leader sequence into consideration.

As appears from the above disclosure, polypeptides which are not identical to the polypeptides having SEQ ID NO: 8, 30, 34, 38, 149, 64, 10 and 88 are embraced by the present invention. The invention allows for minor variations which do not have an adverse effect on immunogenicity compared to the parent sequences and which may give interesting and useful novel binding properties or biological functions and immunogenicities etc.

Each polypeptide fragment may thus be characterized by specific amino acid and nucleic acid sequences. It will be understood that such sequences include analogues and variants produced by recombinant methods wherein such nucleic acid and polypeptide sequences have been modified by substitution, insertion, addition and/or deletion of one or more nucleotides in said nucleic acid sequences to cause the substitution, insertion, addition or deletion of one or more amino acid residues in the recombinant polypeptide. When the term DNA is used in the following, it should be understood that for the number of purposes where DNA can be substituted with RNA, the term DNA should be read to include RNA embodiments which will be apparent for the man skilled in the art. For the purposes of hybridization, PNA may be used instead of DNA, as PNA has been shown to exhibit a very dynamic hybridization profile (PNA is described in Nielsen P E et al., 1991, Science 254: 1497-1500).

The nucleotide sequence to be modified may be of cDNA or genomic origin as discussed above, but may also be of synthetic origin. Furthermore, the sequence may be of mixed cDNA and genomic, mixed cDNA and synthetic or genomic and synthetic origin as discussed above. The sequence may have been modified, e.g. by site-directed mutagenesis, to result in the desired nucleic acid fragment encoding the desired polypeptide.

The nucleotide sequence may be modified using any suitable technique which results in the production of a nucleic acid fragment encoding a polypeptide of the invention.

The modification of the nucleotide sequence encoding the amino acid sequence of the polypeptide of the invention should be one which does not impair the immunological function of the resulting polypeptide.

In particular, the invention relates to a polypeptide obtained from *M. tuberculosis*, which polypeptide has at least one of the following properties:

i) it induces a specific antibody response in a TB patient as determined by an ELISA technique or a western blot when the whole blood is diluted 1:20 in PBS and stimulated with the polypeptide in a concentration of at the most 20 μg/ml and induces an OD of at least 0.1 in ELISA, or a visual response in western blot.

ii) it induces a positive DTH response determined by intradermal injection or local application patch of at most 100 μg of the polypeptide to an individual who is clinically or subclinically infected with a virulent *Mycobacterium*, a positive response having a diameter of at least 10 mm 72-96 hours after the injection or application, iii) it induces a positive DTH response determined by intradermal injection or local application patch of at most 100 μg of the polypeptide to an individual who is clinically or subclinically infected with a virulent *Mycobacterium*, a positive response having a diameter of at least 10 mm 72-96 hours after the injection, and preferably does not induce a such response in an individual who has a cleared infection with a virulent *Mycobacterium.*

Any polypeptide fulfilling one or more of the above properties and which is obtainable from either the cell wall, cell membrane, the cytosol or STCF is within the scope of the present invention.

The property described in i) will in particular be satisfied, if the ELISA is performed as follows: the polypeptide of interest in the concentration of 1 to 10 μg/ml is coated on a 96 wells polystyrene plate (NUNC, Denmark) and after a washing step with phosphate buffer pH 7.3, containing 0.37 M NaCl and 0.5% Tween-20 the serum or plasma from a TB patient is applied in dilution’s from 1:10 to 1:1000 in PBS with 1% Tween-20. Binding of an antibody to the polypeptide is determined by addition of a labeled (e.g. peroxidase labeled) secondary antibody and reaction is thereafter visualized by the use of OPD and $H_2O_2$ as described by the manufacturer (DAKO, Denmark). The OD value in each well is determined using an appropriate ELISA reader.

In a preferred embodiment the western blot is performed as follows: The polypeptide is applied in concentrations from 1-40 µg to a SDS-PAGE and after electrophoresis the polypeptide is transferred to a membrane e.g. nitrocellulose or PVDF. The membrane is thereafter washed in phosphate buffer, pH 7.3, containing 0.37 M NaCl and 0.5% Tween-20 for 30 min. The sera obtained from one or more TB patients were diluted 1:10 to 1:1000 in phosphate buffer pH 7.3 containing 0.37 M NaCl. The membrane is hereafter washed four times five minutes in binding buffer and incubated with peroxidase- or phosphates-labeled secondary antibody. Reaction is then visualized using the staining method recommended by the manufacture (DAKO, Denmark).

The property described in ii) will in particular be satisfied if the polypeptide does not induce such a response in an individual not infected with a virulent *Mycobacterium*, i.e. an individual who has been BCG vaccinated or infected with *Mycobacterium avium* or sensitized by non-tuberculosis *Mycobacterium*. In a preferred embodiment the amount of polypeptide intradermally injected or applied is 90 µg, such as 80 µg, 70 µg, 60 µg, 50 µg, 40 µg, or 30 µg. In another embodiment of the invention, the diameter of the positive response is at least 11 mm, such as 12 mm, 13 mm, 14 mm, or 15 mm. In a preferred embodiment the induration of erythema or both could be determined after administration of the polypeptide by intradermal injection, patch test or multipuncture. The reaction diameter could be positive after more than 48, such as 72 or 96 hours.

The property described in ii) will in particular be satisfied if the polypeptide does not induce such a response in an individual cleared of an infection with a virulent *Mycobacterium*, i.e. which does not have any positive culture or microscopically proven ongoing infection with virulent *Mycobacterium*. The comments on property ii) regarding the amount of polypeptide intradermally injected or applied and the diameter of the positive response are equally relevant to property iii).

In immunodiagnostics, it is often possible and practical to prepare antigens from segments of a known immunogenic protein or polypeptide. Certain epitopic regions may be used to produce responses similar to those produced by the entire antigenic polypeptide. Potential antigenic or immunogenic regions may be identified by any of a number of approaches, e.g., Jameson-Wolf or Kyte-Doolittle antigenicity analyses or Hopp and Woods (Hopp et Woods, (1981), Proc Natl Acad Sci USA 78/6:3824-8) hydrophobicity analysis (see, e.g., Jameson and Wolf, (1988) Comput Appl Biosci, 4(1):181-6; Kyte and Doolittle, (1982) J Mol Biol, 157(1):105-32; or U.S. Pat. No. 4,554,101). Hydrophobicity analysis assigns average hydrophilicity values to each amino acid residue; from these values average hydrophilicities can be calculated and regions of greatest hydrophilicity determined. Using one or more of these methods, regions of predicted antigenicity may be derived from the amino acid sequence assigned to the polypeptides of the invention. Alternatively, in order to identify relevant T-cell epitopes which are recognized during an immune response, it is also possible to use a "brute force" method: Since T-cell epitopes are linear, deletion mutants of polypeptides will, if constructed systematically, reveal what regions of the polypeptide are essential in immune recognition. A presently preferred method utilises overlapping oligomers (preferably synthetic ones having a length of e.g. 20 amino acid residues) derived from the polypeptide. A preferred T-cell epitope is a T-helper cell epitope or a cytotoxic T-cell epitope.

Although the minimum length of a T-cell epitope has been shown to be at least 6 amino acids, it is normal that such epitopes are constituted of longer stretches of amino acids. Hence it is preferred that the polypeptide fragment of the invention has a length of at least 7 amino acid residues, such as at least 8, at least 9, at least 10, at least 12, at least 14, at least 16, at least 18, at least 20, at least 22, at least 24, or at least 30 amino acid residues.

B-cell epitopes may be linear or spatial. The three-dimensional structure of a protein is often such that amino acids, which are located distant from each other in the one-dimensional structure, are located near to each other in the folded protein. Within the meaning of the present context, the expression epitope is intended to comprise the one- and three-dimensional structure as well as mimics thereof. The term is further intended to include discontinuous B-cell epitopes. The linear B-cell epitopes can be identified in a similar manner as described for the T-cell epitopes above. However, when identifying B-cell epitopes the assay should be an ELISA using overlapping oligomers derived from the polypeptide as the coating layer on a microtiter plate as described elsewhere.

A non-naturally occurring polypeptide, an analogue, a subsequence, a T-cell epitope and/or a B-cell epitope of any of the described polypeptides are defined as any non-naturally occurring polypeptide, analogue, subsequence, T-cell epitope and/or B-cell epitope of any of the polypeptides inducing a specific antibody response in a TB patient.

Preferred embodiments of the invention are the specific polypeptides which have been identified and analogues and subsequences thereof. It has been noted that none of the identified polypeptides in the examples include a signal sequence. Table 1 lists the antigens of the invention.

TABLE 1

The antigens of the invention by the names used herein as well as by reference to relevant SEQ ID NOs of N-terminal sequences, full amino acid sequences and sequences of nucleotides encoding the antigens

| Antigen | Sanger ID | Nucleotide sequence SEQ ID NO: | Amino acid sequence SEQ ID NO: |
|---------|-----------|-------------------------------|-------------------------------|
| TB15A   | Rv1636    | 7                             | 8                             |
| TB16    | Rv2185c   | 29                            | 30                            |
| TB32    | Rv2623    | 33                            | 34                            |
| TB51    | Rv2462c   | 37                            | 38                            |
| CFP8A   | Rv3354    | 148                           | 149                           |
| CFP16   | Rv0652    | 63                            | 64                            |
| CFP21   | Rv1984c   | 9                             | 10                            |
| CFP23   | Rv3451    | 55                            | 56                            |
| RD1-ORF3| Rv3872    | 87                            | 88                            |

Until the present invention was made, it was unknown that the polypeptides Rv1636, Rv2185c, Rv2623, Rv2462c, Rv3354, Rv0652, Rv1984c, Rv3451 or Rv3872 with the amino acid sequences disclosed in SEQ ID NOs: 8, 30, 34, 38, 149, 64, 10, 56 and 88 are expressed in live virulent *Mycobacterium*. These polypeptides in purified form, or non-naturally occurring, i.e. recombinantly or synthetically produced, are considered part of the invention. It is understood that a polypeptide which has the above mentioned property and has a sequence identity of at least 80% with any of the amino acid sequences shown in SEQ ID NOs: 8, 30, 34, 38, 149, 64, 10, 56 and 88 or has a sequence identity of at least 80% to any subsequence thereof is considered part of the invention. In a preferred embodiment the sequence identity is at least 80%, such as 81%, 82%, 83%, 84%, 85%, 86%, 87%, 88%, 89%, 90%, 91%, 92%, 93%, 94%, 95%, 96%, 97%, 98%, 99% or 99.5%. Furthermore, any T cell epitope of the polypeptides disclosed in SEQ ID NOs: 8, 30, 34, 38, 149, 64, 10 56, and 88 is considered part of the invention. Also, any B-cell epitope of the polypeptides disclosed in SEQ ID NOs: 8, 30, 34, 38, 149, 64, 10, 56 and 88 is considered part of the invention.

The invention also relates to a replicable expression vector which comprises a nucleic acid fragment defined above, especially a vector which comprises a nucleic acid fragment encoding a polypeptide fragment of the invention. The vector may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication; examples of such a vector are a plasmid, phage, cosmid, mini-chromosome and virus. Alternatively, the vector may be one which, when introduced in a host cell, is integrated in the host cell genome and replicated together with the chromosome(s) into which it has been integrated.

Expression vectors may be constructed to include any of the DNA segments disclosed herein. Such DNA might encode an antigenic protein specific for virulent strains of mycobacteria or even hybridization probes for detecting mycobacteria nucleic acids in samples. Longer or shorter DNA segments could be used, depending on the antigenic protein desired. Epitopic regions of the proteins expressed or encoded by the disclosed DNA could be included as relatively short segments of DNA. A wide variety of expression vectors is possible including, for example, DNA segments encoding reporter gene products useful for identification of heterologous gene products and/or resistance genes such as antibiotic resistance genes which may be useful in identifying transformed cells.

The vector of the invention may be used to transform cells so as to allow propagation of the nucleic acid fragments of the invention or so as to allow expression of the polypeptide fragments of the invention. Hence, the invention also pertains to a transformed cell harbouring at least one such vector according to the invention, said cell being one which does not natively harbour the vector and/or the nucleic acid fragment of the invention contained therein. Such a trans-formed cell (which is also a part of the invention) may be any suitable bacterial host cell or any other type of cell such as a unicellular eukaryotic organism, a fungus or yeast, or a cell derived from a multicellular organism, e.g. an animal or a plant. It is especially in cases where glycosylation is desired that a mammalian cell is used, although glycosylation of proteins is a rare event in prokaryotes. Normally, however, a prokaryotic cell is preferred such as a bacterium belonging to the genera *Mycobacterium, Salmonella, Pseudomonas, Bacillus* and *Eschericia*. It is preferred that the transformed cell is an *E. coli, B. subtilis*, or *M. bovis* BCG cell, and it is especially preferred that the transformed cell expresses a polypeptide according of the invention. The latter opens for the possibility to produce the polypeptide of the invention by simply recovering it from the culture containing the transformed cell. In the most preferred embodiment of this part of the invention the transformed cell is *Mycobacterium bovis* BCG strain: Danish 1331, which is the *Mycobacterium bovis* strain Copenhagen from the Copenhagen BCG Laboratory, Statens Seruminstitut, Denmark.

The nucleic acid fragments of the invention allow for the recombinant production of the polypeptides fragments of the invention. However, also isolation from the natural source is a way of providing the polypeptide fragments as is peptide synthesis.

Therefore, the invention also pertains to a method for the preparation of a polypeptide fragment of the invention, said method comprising inserting a nucleic acid fragment as described in the present application into a vector which is able to replicate in a host cell, introducing the resulting recombinant vector into the host cell (transformed cells may be selected using various techniques, including screening by differential hybridization, identification of fused reporter gene products, resistance markers, anti-antigen antibodies and the like), culturing the host cell in a culture medium under conditions sufficient to effect expression of the polypeptide (of course the cell may be cultivated under conditions appropriate to the circumstances, and if DNA is desired, replication conditions are used), and recovering the polypeptide from the host cell or culture medium; or isolating the polypeptide from a short-term culture filtrate; or isolating the polypeptide from whole mycobacteria of the tuberculosis complex or from lysates or fractions thereof, e.g. cell wall containing fractions, or synthesizing the polypeptide by solid or liquid phase peptide synthesis.

The medium used to grow the transformed cells may be any conventional medium suitable for the purpose. A suitable vector may be any of the vectors described above, and an appropriate host cell may be any of the cell types listed above. The methods employed to construct the vector and effect introduction thereof into the host cell may be any methods known for such purposes within the field of recombinant DNA. In the following a more detailed description of the possibilities will be given:

In general, of course, prokaryotes are preferred for the initial cloning of nucleic sequences of the invention and constructing the vectors useful in the invention. For example, in addition to the particular strains mentioned in the more specific disclosure below, one may mention by way of example, strains such as *E. Coli* K12 strain 294 (ATCC No. 31446), *E. coli* B, and *E. coli* X 1776 (ATCC No. 31537). These examples are, of course, intended to be illustrative and not limiting.

Prokaryotes are also preferred for expression. The aforementioned strains, as well as *E. coli* W3110 (F-, lambda-, prototrophic, ATCC No. 273325), bacilli such as *Bacillus subtilis*, or other enterobacteriaceae such as *Salmonella typhimurium* or *Serratia marcesans*, and various *Pseudomonas* species may be used. Especially interesting are rapid-growing mycobacteria, e.g. *M. smegmatis*, as these bacteria have a high degree of resemblance with mycobacteria of the tuberculosis complex and therefore stand a good chance of reducing the need of performing post-translational modifications of the expression product.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species (see, e.g., Bolivar et al., 1977, Gene 2: 95). The pBR322 plasmid contains genes for ampicillin and tetracycline resistance and thus provides easy means for identifying transformed cells. The pBR plasmid, or other microbial plasmids or phages must also contain, or be modified to contain, promoters which can be used by the microorganism for expression.

Those promoters most commonly used in recombinant DNA construction include the B-lactamase (penicillinase) and lactose promoter systems (Chang et al., (1978), Nature, 35:515; Itakura et al., (1977), Science 198:1056; Goeddel et al., (1979), Nature 281:544) and a tryptophan (trp) promoter system (Goeddel et al., (1979) Nature 281:544; EPO Appl. Publ. No. 0036776). While these are the most commonly used, other microbial promoters have been discovered and utilized, and details concerning their nucleotide sequences have been published, enabling a skilled worker to ligate them functionally with plasmid vectors (Siebwenlist et al., (1980), Cell, 20:269). Certain genes from prokaryotes may be expressed efficiently in *E. coli* from their own promoter sequences, precluding the need for addition of another promoter by artificial means.

After the recombinant preparation of the polypeptide according to the invention, the isolation of the polypeptide may for instance be carried out by affinity chromatography (or other conventional biochemical procedures based on chromatography), using a monoclonal antibody which substantially specifically binds the polypeptide according to the invention. Another possibility is to employ the simultaneous electroelution technique described by Andersen et al. in J. Immunol. Methods 161: 29-39.

According to the invention the post-translational modifications involves lipidation, glycosylation, cleavage, or elongation of the polypeptide.

Individuals infected with virulent *Mycobacteria* can generally be divided into two groups. The first group has an infection with a virulent *Mycobacterium* e.g. contacts of TB patients. The virulent *Mycobacterium* may have established colonies in the lungs, but the individual has, as yet, no symptoms of TB. The second group has clinical symptoms of TB, as a TB patient.

In one embodiment of the invention, any of the above mentioned polypeptides are used for the manufacture of a diagnostic reagent that preferably distinguishes a subclinically or clinically infected individual (group I and group II) from an individual who has been BCG vaccinated or infected with *Mycobacterium avium* or sensitized by non-tuberculosis *Mycobacterium* (NTM), and may distinguish a subclinically or clinically infected individual from an individual who has cleared a previous infection with a virulent *Mycobacterium*. It is most likely that specific polypeptides derived from SPE or ST-CF will identify group I and/or group II from individuals not infected with virulent *Mycobacteria* in the same way as ESAT-6 and CFP10 (P. Ravn et al., (1998), J. Infectious Disease 179:637-45).

In another embodiment of the invention, any of the above discussed polypeptides are used for the manufacture of a diagnostic reagent for the diagnosis of an infection with a virulent *Mycobacterium*. One embodiment of the invention provides a diagnostic reagent for differentiating an individual who is clinically or subclinically infected with a virulent *Mycobacterium* from an individual not infected with virulent *Mycobacterium*, i.e. an individual who has been BCG vaccinated or infected with *Mycobacterium avium* or sensitized by non-tuberculosis *Mycobacterium* (NTM). Such a diagnostic reagent will distinguish between an individual in group I and/or II of the infection stages above, from an individual who has been vaccinated against TB.

Another embodiment of the invention provides a diagnostic reagent for differentiating an individual who is clinically or subclinically infected with a virulent *Mycobacterium* from an individual who has a cleared infection with a virulent *Mycobacterium*. Such a diagnostic reagent will distinguish between an individual in group I and/or II of the infection stages above, from an individual who has cleared the infection.

Determination of an infection with virulent *Mycobacterium* will be instrumental in the, still very laborious, diagnostic process of tuberculosis. A number of possible diagnostic assays and methods can be envisaged (some more specifically described in the examples and the list of properties): a sample comprising whole blood or mononuclear cells (i.a. T-lymphocytes) from a patient could be contacted with a sample of one or more polypeptides of the invention. This contacting can be performed in vitro and a positive reaction could e.g. be proliferation of the T-cells or release of cytokines such as IFN-γ into the extracellular phase (e.g. into a culture supernatant).

Alternatively, a sample of a possibly infected organ may be contacted with an antibody raised against a polypeptide of the invention. The demonstration of the reaction by means of methods well-known in the art between the sample and the antibody will be indicative of ongoing infection and could be used to monitor treatment effect by reduction in responses.

It is of course also a possibility to demonstrate the presence of anti-Mycobacterial antibodies in serum by contacting a serum sample from a subject with at least one of the polypeptide fragments of the invention and using well-known methods for visualising the reaction between the antibody and antigen such as ELISA, Western blot, precipitation assays.

The invention also relates to a method of diagnosing infection caused by a virulent *Mycobacterium* in a mammal, including a human being, comprising locally applying (patch test) or intradermally injecting (Mantoux test) a polypeptide of the invention. These tests are both called a delayed hypersensitivity reaction (DTH). A positive skin response at the location of injection or application is indicative of the mammal including a human being, being infected with a virulent *Mycobacterium*, and a negative skin response at the location of injection or application is indicative of the mammal including a human being not having TB. A positive response is a skin reaction having a diameter of at least 5 mm larger than background, but larger reactions are preferred, such as at least 1 cm, 1.5 cm, and at least 2 cm in diameter. A skin reaction is here to mean erythema or induration of the skin, as directly measured. The composition used as the skin test reagent can be prepared in the same manner as described for the vaccines above.

In human volunteers, the generation of a significant immune response can alternatively be defined as the ability of the reagent being tested to stimulate an in vitro recall response by peripheral blood cells from at least 30% of PPD positive individuals previously vaccinated with that reagent or infected with a virulent *Mycobacterium*, said recall response being defined as proliferation of T cells or the production of cytokine(s) which is higher than the responses generated by cells from unimmunized or uninfected control individuals, with a 95% confidence interval as defined by an appropriate statistical analysis such as a Student's two-tailed T test.

The polypeptides according to the invention may be potential drug targets. The fact that certain of the disclosed antigens are not present in *M. bovis* BCG but are present in virulent mycobacteria point them out as interesting drug targets; the antigens may constitute receptor molecules or toxins which facilitate the infection by the mycobacterium, and if such functionalities are blocked the infectivity of the mycobacterium will be diminished.

To determine particularly suitable drug targets among the antigens of the invention, the gene encoding at least one of the polypeptides of the invention and the necessary control sequences can be introduced into avirulent strains of mycobacteria (e.g. BCG) so as to determine which of the polypeptides are critical for virulence. Once particular proteins are identified as critical for/contributory to virulence, anti-mycobacterial agents can be designed rationally to inhibit expression of the critical genes or to attack the critical gene products. For instance, antibodies or fragments thereof (such as Fab and (Fab')$_2$ fragments can be prepared against such critical polypeptides by methods known in the art and thereafter used as prophylactic or therapeutic agents. Alternatively, small molecules can be screened for their ability to selectively inhibit expression of the critical gene products, e.g. using recombinant expression systems which include the gene's endogenous promoter, or for their ability to directly interfere with the action of the target. These small molecules are then used as therapeutics or as prophylactic agents to inhibit mycobacterial virulence.

Alternatively, anti-mycobacterial agents which render a virulent mycobacterium avirulent can be operably linked to expression control sequences and used to transform a virulent mycobacterium. Such anti-mycobacterial agents inhibit the replication of a specified mycobacterium upon transcription or translation of the agent in the mycobacterium. Such a "newly avirulent" mycobacterium would constitute a superb alternative to the above described modified BCG for vaccine purposes since it would be immunologically very similar to a virulent mycobacterium compared to e.g. BCG.

Once a particular interesting polypeptide has been identified, the biological function of that polypeptide may be tested. The polypeptides may constitute receptor molecules or toxins which facilitates the infection by the *Mycobacterium* and if such functionality is blocked, the infectivity of the virulent *Mycobacterium* will be diminished.

The biological function of particular interesting polypeptides may be tested by studying the effect of inhibiting the expression of the polypeptides on the virulence of the virulent *Mycobacterium*. This inhibition may be performed at the gene level such as by blocking the expression using antisense nucleic acid, PNA or LNA or by interfering with regulatory sequences or the inhibition may be at the level of translation or post-translational processing of the polypeptide.

Once a particular polypeptide according to the invention is identified as critical for virulence, an anti-mycobacterial agent might be designed to inhibit the expression of that polypeptide. Such anti-mycobacterial agent might be used as a prophylactic or therapeutic agent. For instance, antibodies or fragments thereof, such as Fab and (Fab')$_2$ fragments, can be prepared against such critical polypeptides by methods known in the art and thereafter used as prophylactic or therapeutic agents A monoclonal or polyclonal antibody, which is specifically reacting with a polypeptide of the invention in an immuno assay, or a specific binding fragment of said antibody, is also a part of the invention. The production of such polyclonal antibodies requires that a suitable animal be immunized with the polypeptide and that these antibodies are subsequently isolated, suitably by immune affinity chromatography. The production of monoclonals can be effected by methods well-known in the art, since the present invention provides for adequate amounts of antigen for both immunization and screening of positive hybridomas.

As will appear from the examples, a number of the polypeptides of the invention are natively translation products which include a leader sequence (or other short peptide sequences), whereas the product which can be isolated from short-term culture filtrates from bacteria belonging to the tuberculosis complex are free of these sequences. Although it may in some applications be advantageous to produce these polypeptides recombinantly and in this connection facilitate export of the polypeptides from the host cell by including information encoding the leader sequence in the gene for the polypeptide, it is more often preferred to either substitute the leader sequence with one which has been shown to be superior in the host system for effecting export, or to totally omit the leader sequence (e.g. when producing the polypeptide by peptide synthesis. Hence, a preferred embodiment of the invention is a polypeptide which is free from amino acid residues −32 to −1 in SEQ ID NO: 10 and/or −33 to −1 in SEQ ID NO: 56.

In another preferred embodiment, the polypeptide fragment of the invention is free from any signal sequence; this is especially interesting when the polypeptide fragment is produced synthetically but even when the polypeptide fragments are produced recombinantly it is normally acceptable that they are not exported by the host cell to the periplasm or the extracellular space; the polypeptide fragments can be recovered by traditional methods (cf. the discussion below) from the cytoplasm after disruption of the host cells, and if there is need for refolding of the polypeptide fragments, general refolding schemes can be employed, cf. e.g. the disclosure in WO 94/18227 where such a general applicable refolding method is described.

As mentioned above, it will normally be interesting to omit the leader sequences from the polypeptide fragments of the invention. However, by producing fusion polypeptides, superior characteristics of the polypeptide fragments of the invention can be achieved. For instance, fusion partners which facilitate export of the polypeptide when produced recombinantly, fusion partners which facilitate purification of the polypeptide, and fusion partners which enhance the immunogenicity of the polypeptide fragment of the invention are all interesting possibilities. Therefore, the invention also pertains to a fusion polypeptide comprising at least one polypeptide fragment defined above and at least one fusion partner. The fusion partner can, in order to enhance immunogenicity, e.g. be selected from the group consisting of another polypeptide fragment as defined above (so as to allow for multiple expression of relevant epitopes), and an other polypeptide derived from a bacterium belonging to the tuberculosis complex, such as ESAT-6, MPB64, MPT64, and MPB59 or at least one T-cell epitope of any of these antigens. Other immunogenicity enhancing polypeptides which could serve as fusion partners are T-cell epitopes (e.g. derived from the polypeptides ESAT-6, MPB64, MPT64, or MPB59) or other immunogenic epitopes enhancing the immunogenicity of the target gene product, e.g. lymphokines such as IFN-γ, IL-2 and IL-12. In order to facilitate expression and/or purification the fusion partner can e.g. be a bacterial fimbrial protein, e.g. the pilus components pilin and papA; protein A; the ZZ-peptide (ZZ-fusions are marketed by Pharmacia in Sweden); the maltose binding protein; glutathione S-transferase; β-galactosidase; or polyhistidine.

Also a method of determining the presence of virulent *Mycobacterium* nucleic acids in a mammal, including a human being, or in a sample, comprising incubating the sample with a nucleic acid sequence of the invention or a nucleic acid sequence complementary thereto, and detecting the presence of hybridized nucleic acids resulting from the incubation (by using the hybridization assays which are well-known in the art), is included in the invention. Such a method of diagnosing TB might involve the use of a composition comprising at least a part of a nucleotide sequence as defined above and detecting the presence of nucleotide sequences in a sample from the animal or human being to be tested which hybridizes with the nucleic acid sequence (or a complementary sequence) by the use of PCR techniques.

In certain aspects, the DNA sequence information provided by this invention allows for the preparation of relatively short DNA (or RNA or PNA) sequences having the ability to specifically hybridize to mycobacterial gene sequences. In these aspects, nucleic acid probes of an appropriate length are prepared based on a consideration of the relevant sequence. The ability of such nucleic acid probes to specifically hybridize to the mycobacterial gene sequences lend them particular utility in a variety of embodiments. Most importantly, the probes can be used in a variety of diagnostic assays for detecting the presence of pathogenic organisms in a given sample. However, either uses are envisioned, including the use of the sequence information for the preparation of mutant species primers, or primers for use in preparing other genetic constructs.

In one embodiment of the invention a composition is produced comprising as the effective component a micro-organism, the micro-organism is a bacterium such as *Mycobacterium*, *Salmonella*, *Pseudomonas* and *Escherichia*, preferably *Mycobacterium bovis* BCG wherein at least one, such as at least 2 copies, such as at least 5 copies of a nucleotide fragment comprising a nucleotide sequence encoding a polypeptide of the invention has been incorporated into the genome of the micro-organism or introduced as a part of an expression vector in a manner allowing the micro-organism to express and optionally secrete the polypeptide. In a preferred embodiment, the composition comprises at least 2 different nucleotide sequences encoding at least 2 different polypeptides of the invention.

Another part of the invention pertains to a nucleic acid fragment in isolated form which
1) comprises a nucleic acid sequence which encodes a polypeptide or fusion polypeptide as defined above, or comprises a nucleic acid sequence complementary thereto, and/or
2) has a length of at least 10 nucleotides and hybridizes readily under stringent hybridization conditions (as defined in the art, i.e. 5-10° C. under the melting point $T_m$, cf. Sambrook et al, 1989, pages 11.45-11.49) with a nucleic acid fragment which has a nucleotide sequence selected from
   SEQ ID NO: 7 or a sequence complementary thereto,
   SEQ ID NO: 29 or a sequence complementary thereto,
   SEQ ID NO: 33 or a sequence complementary thereto,
   SEQ ID NO: 37 or a sequence complementary thereto,
   SEQ ID NO: 148 or a sequence complementary thereto,
   SEQ ID NO: 63 or a sequence complementary thereto,
   SEQ ID NO: 9 or a sequence complementary thereto,
   SEQ ID NO: 55 or a sequence complementary thereto,
   SEQ ID NO: 87 or a sequence complementary thereto
   It is preferred that the nucleic acid fragment is a DNA fragment.

To provide certainty of the advantages in accordance with the invention, the preferred nucleic acid sequence when employed for hybridization studies or assays includes sequences that are complementary to at least a 10 to 40, or so, nucleotide stretch of the selected sequence. A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained.

A preferred immunologic composition according to the present invention comprising at least two different polypeptide fragments, each different polypeptide fragment being a polypeptide or a fusion polypeptide defined above. It is preferred that the immunologic composition comprises between 3-20 different polypeptide fragments or fusion polypeptides.

EXAMPLES

Example 1A

Isolation of CFP21

ST-CF was precipitated with ammonium sulphate at 80% saturation. The precipitated proteins were removed by centrifugation and after resuspension washed with 8 M urea. CHAPS and glycerol were added to a final concentration of 0.5% (w/v) and 5% (v/v) respectively and the protein solution was applied to a Rotofor isoelectrical Cell (BioRad). The Rotofor Cell had been equilibrated with an 8 M urea buffer containing 0.5% (w/v) CHAPS, 5% (v/v) glycerol, 3% (v/v) Biolyt 3/5 and 1% (v/v) Biolyt 4/6 (BioRad). Isoelectric focusing was performed in a pH gradient from 3-6. The fractions were analyzed on silver-stained 10-20% SDS-PAGE. Fractions with similar band patterns were pooled and washed three times with PBS on a Centriprep concentrator (Amicon) with a 3 kDa cut off membrane to a final volume of 1-3 ml. An equal volume of SDS containing sample buffer was added and the protein solution boiled for 5 min before further separation on a Prep Cell (BioRad) in a matrix of 16% polyacrylamide under an electrical gradient. Fractions containing pure proteins with an molecular mass from 17-30 kDa were collected.
N-Terminal Sequencing and Amino Acid Analysis CFP21 was washed with water on a Centricon concentrator (Amicon) with cutoff at 10 kDa and then applied to a ProSpin concentrator (Applied Biosystems) where the proteins were collected on a PVDF membrane. The membrane was washed 5 times with 20% methanol before sequencing on a Procise sequencer (Applied Biosystems).

The following N-terminal sequence was obtained:

```
For CFP21:
D P X S D I A V V F A R G T H    (SEQ ID NO: 150)
```

"X" denotes an amino acid which could not be determined by the sequencing method used, whereas a "/" between two amino acids denotes that the sequencing method could not determine which of the two amino acids is the one actually present.
Homology Searches in the Sanger Database For CFP21 the N-terminal amino acid sequence was used for a homology search using the blast program of the Sanger *Mycobacterium tuberculosis* database:
http://www.sanger.ac.uk/pathogens/TB-blast-server.html.
Thereby, the following information was obtained:
CFP21

A sequence 100% identical to the 14 determined amino acids of CFP21 was found at MTCY39. From the N-terminal sequencing it was not possible to determine amino acid number 3; this amino acid is a C in MTCY39. The amino acid C can not be detected on a Sequencer which is probably the explanation of this difference.

Within the open reading frame the translated protein is 217 amino acids long. The N-terminally determined sequence from the protein purified from culture filtrate starts at amino acid 33 in agreement with the presence of a signal sequence that has been cleaved off. This gives a length of the mature protein of 185 amino acids, which corresponds to a theoretical molecular weigh at 18657 Da, and a theoretical pI at 4.6. The observed weight in a SDS-PAGE is 21 kDa.

In a 193 amino acids overlap the protein has 32.6% identity to a cutinase precursor with a length of 209 amino acids (CUTI_ALTBR P41744).

A comparison of the 14 N-terminal determined amino acids with the translated region (RD2) deleted in *M. bovis* BCG revealed a 100% identical sequence (mb3484) (Mahairas et al. (1996)).

Expression/Purification of Recombinant CFP21 Protein.

Expression and metal affinity purification of recombinant proteins was undertaken essentially as described by the manufacturers. For each protein, 1 l LB-media containing 100 μg/ml ampicillin, was inoculated with 10 ml of an overnight culture of XL1-Blue cells harbouring recombinant pMCT6 plasmids. Cultures were shaken at 37° C. until they reached a density of $OD_{600}$=0.4-0.6. IPTG was hereafter added to a final concentration of 1 mM and the cultures were further incubated 4-16 hours. Cells were harvested, resuspended in

```
CFP21:
                                          (SEQ ID NO: 10)
  1 MTPRSLVRIV GVVVATTLAL VSAPAGGRAA HADPCSDIAV

41 VFARGTHQAS GLGDVGEAFV DSLTSQVGGR SIGVYAVNYP ASDDYRASAS

91 NGSDDASAHI QRTVASCPNT RIVLGGYSQG ATVIDLSTSA MPPAVADHVA

141 AVALFGEPSS GFSSMLWGGG SLPTIGPLYS SKTINLCAPD DPICTGGGNI

191 MAHVSYVQSG MTSQAATFAA NRLDHAG
```

Cloning of the Gene Encoding CFP21

The gene encoding CFP21 was cloned into the expression vector pMCT6, by PCR amplification with gene specific primers, for recombinant expression in *E. coli* of the proteins.

PCR reactions contained 10 ng of *M. tuberculosis* chromosomal DNA in 1× low salt Taq+ buffer from Stratagene supplemented with 250 mM of each of the four nucleotides (Boehringer Mannheim), 0.5 mg/ml BSA (IgG technology), 1% DMSO (Merck), 5 pmoles of each primer and 0.5 unit Tag+ DNA polymerase (Stratagene) in 10 μl reaction volume. Reactions were initially heated to 94° C. for 25 sec. and run for 30 cycles according to the following program; 94° C. for 10 sec., 55° C. for 10 sec. and 72° C. for 90 sec, using thermocycler equipment from Idaho Technology.

The DNA fragments were subsequently run on 1% agarose gels, the bands were excised and purified by Spin-X spin columns (Costar) and cloned into pBluescript SK II+-T vector (Stratagene). Plasmid DNA was thereafter prepared from clones harbouring the desired fragments, digested with suitable restriction enzymes and subcloned into the expression vector pMCT6 in frame with 8 histidine residues which are added to the N-terminal of the expressed proteins. The resulting clones were hereafter sequenced by use of the dideoxy chain termination method adapted for supercoiled DNA using the Sequenase DNA sequencing kit version 1.0 (United States Biochemical Corp., USA) and by cycle sequencing using the Dye Terminator system in combination with an automated gel reader (model 373A; Applied Biosystems) according to the instructions provided. Both strands of the DNA were sequenced.

For cloning the following gene specific primers were used:

```
CFP21: Primers used for cloning of cfp21:
OPBR-55:
ACAGATCTGCGCATGCGGATCCGTGT       (SEQ ID NO: 151)

OPBR-56:
TTTTCCATGGTCATCCGGCGTGATCGAG     (SEQ ID NO: 152)
```

OPBR-55 and OPBR-56 create BglII and NcoI sites, respectively, used for the cloning in pMCT6.

1× sonication buffer+8 M urea and sonicated 5×30 sec. with 30 sec. pausing between the pulses.

After centrifugation, the lysate was applied to a column containing 25 ml of resuspended Talon resin (Clontech, Palo Alto, USA). The column was washed and eluted as described by the manufacturers.

After elution, all fractions (1.5 ml each) were subjected to analysis by SDS-PAGE using the Mighty Small (Hoefer Scientific Instruments, USA) system and the protein concentrations were estimated at 280 nm. Fractions containing recombinant protein were pooled and dialysed against 3 M urea in 10 mM Tris-HCl, pH 8.5. The dialysed protein was further purified by FPLC (Pharmacia, Sweden) using a 6 ml Resource-Q column, eluted with a linear 0-1 M gradient of NaCl. Fractions were analyzed by SDS-PAGE and protein concentrations were estimated at $OD_{280}$. Fractions containing protein were pooled and dialysed against 25 mM Hepes buffer, pH 8.5.

Finally the protein concentration and the LPS content were determined by the BCA (Pierce, Holland) and LAL (Endosafe, Charleston, USA) tests, respectively.

Example 1B

Identification of RD1-ORF3

In an effort to control the threat of TB, attenuated *bacillus* Calmette-Guérin (BCG) has been used as a live attenuated vaccine. BCG is an attenuated derivative of a virulent *Mycobacterium bovis*. The original BCG from the Pasteur Institute in Paris, France was developed from 1908 to 1921 by 231 passages in liquid culture and has never been shown to revert to virulence in animals, indicating that the attenuating mutation(s) in BCG are stable deletions and/or multiple mutations which do not readily revert. While physiological differences between BCG and *M. tuberculosis* and *M. bovis* has been noted, the attenuating mutations which arose during serial passage of the original BCG strain has been unknown until recently. The first mutations described are the loss of the gene encoding MPB64 in some BCG strains (Li et al., 1993, Oettinger and Andersen, 1994) and the gene encoding ESAT-6 in all BCG strain tested (Harboe et al., 1996), later 3 large deletions in BCG have been identified (Mahairas et al., 1996). The region named RD1 includes the gene encoding ESAT-6 and an other (RD2) the gene encoding MPT64. Both antigens have been shown to have diagnostic potential and ESAT-6 has been shown to have properties as a vaccine candidate (cf. PCT/DK94/00273 and PCT/DK/00270). In order to find new M. tuberculosis specific diagnostic antigens as well as antigens for a new vaccine against TB, the RD1 region (17.499 bp) of M. tuberculosis H37Rv has been analyzed for Open Reading Frames (ORF). ORFs with a minimum length of 96 bp have been predicted using the algorithm described by Borodovsky and McIninch (1993), in total 27 ORFs have been predicted, 20 of these have possible diagnostic and/or vaccine potential, as they are deleted from all known BCG strains. The predicted ORFs include ESAT-6 (RD1-ORF7) and CFP10 (RD1-ORF6) described previously (Sørensen et al., 1995), as a positive control for the ability of the algorithm. In the present is described the potential of 1 of the predicted antigens for diagnosis of TB.

Identification of rd1-orf3.

The nucleotide sequence of rd1-orf3 from M. tuberculosis H37Rv is set forth in SEQ ID NO: 87. The deduced amino acid sequence of RD1-ORF2 is set forth in SEQ ID NO: 88.

The DNA sequence rd1-orf3 (SEQ ID NO: 87) contained an open reading frame starting with an ATG codon at position 2807-2809 and ending with a termination codon (TAA) at position 3101-3103 (position numbers referring to the location in RD1). The deduced amino acid sequence (SEQ ID NO: 88) contains 98 residues corresponding to a molecular weight of 9,799.

Cloning of rd1-orf3.

Rd1-orf3 was PCR cloned in the pMST24 (Theisen et al., 1995) expression vector. Chromosomal DNA from M. tuberculosis H37Rv was used as template in the PCR reactions. Oligonucleotides were synthesized on the basis of the nucleotide sequence from the RD1 region (Accession no. U34848). The oligonucleotide primers were engineered to include an restriction enzyme site at the 5' end and at the 3' end by which a later subcloning was possible. Primers are listed in table 2. rd1-orf3. A SmaI site was engineered immediately 5' of the first codon of rd1-orf3, and a NcoI site was incorporated right after the stop codon at the 3' end. The gene rd1-orf3 was subcloned in pMST24, giving pTO87.

The PCR fragments were digested with the suitable restriction enzymes, purified from an agarose gel and cloned into pMST24. The construct was used to transform the E. coli XL1-Blue. Endpoints of the gene fusions were determined by the dideoxy chain termination method. Both strands of the DNA were sequenced.

Purification of Recombinant RD1-ORF3.

The rRD1-ORF3 was fused N-terminally to the (His)$_6$-tag. Recombinant antigen was prepared as described in example 1a Purification of recombinant antigen by Ni$^{2+}$ affinity chromatography was also carried out as described in example 1b. Fractions containing purified His-rRD1-ORF3 were pooled. The His-rRD1-ORF3 were extensively dialysed against 10 mM Tris/HCl, pH 8.5, 3 M urea followed by an additional purification step performed on an anion exchange column (Mono Q) using fast protein liquid chromatography (FPLC) (Pharmacia, Uppsala, Sweden). The purification was carried out in 10 mM Tris/HCl, pH 8.5, 3 M urea and protein was eluted by a linear gradient of NaCl from 0 to 1 M. Fractions containing the His-rRD1-ORF3 were pooled and subsequently dialysed extensively against 25 mM Hepes, pH 8.0 before use.

TABLE 2

Sequence of the rd1-orf3 oligonucleotides[a].

| Orientation and oligonucleotide | Sequences 5'→3' | Position (nt) |
|---|---|---|
| Sense RD1-ORF3f | CTTCCCGGGATGGAAAAAATGTC AC SEQ ID NO: 153) | 2807-2822 |
| Antisense RD1-ORF3r | GATGCCATGGTTAGGCGAAGACGC CGGC SEQ ID NO: 154) | 3103-3086 |

[a]The oligonucleotides were constructed from the Accession number U34484 nucleotide sequence (Mahairas et al., 1996). Nucleotides (nt) underlined are not contained in the nucleotide sequence of RD1-ORF's. The positions correspond to the nucleotide sequence of Accession number U34484.

The nucleotide sequences of rd1-orf3 from M. tuberculosis H37Rv are set forth in SEQ ID NO: 87. The deduced amino acid sequences of rd1-orf3 are set forth in SEQ ID NO: 88.

Example 1C

Identification of CFP8A, CFP16 and CFP23

Identification of CFP16.

ST-CF was precipitated with ammonium sulphate at 80% saturation. The precipitated proteins were removed by centrifugation and after resuspension washed with 8 M urea. CHAPS and glycerol were added to a final concentration of 0.5% (w/v) and 5% (v/v) respectively and the protein solution was applied to a Rotofor isoelectrical Cell (BioRad). The Rotofor Cell had been equilibrated with a 8M urea buffer containing 0.5% (w/v) CHAPS, 5% (v/v) glycerol, 3% (v/v) Biolyt 3/5 and 1% (v/v) Biolyt 4/6 (BioRad). Isoelectric focusing was performed in a pH gradient from 3-6. The fractions were analyzed on silver-stained 10-20% SDS-PAGE. Fractions with similar band patterns were pooled and washed three times with PBS on a Centriprep concentrator (Amicon) with a 3 kDa cut off membrane to a final volume of 1-3 ml. An equal volume of SDS containing sample buffer was added and the protein solution boiled for 5 min before further separation on a Prep Cell (BioRad) in a matrix of 16% polyacrylamide under an electrical gradient. Fractions containing well separated bands in SDS-PAGE were selected for N-terminal sequencing after transfer to PVDF membrane.

Isolation of CFP8A

ST-CF was precipitated with ammonium sulphate at 80% saturation and redissolved in PBS, pH 7.4, and dialysed 3 times against 25 mM piperazin-HCl, pH 5.5, and subjected to chromatofocusing on a matrix of PBE 94 (Pharmacia) in a column connected to an FPLC system (Pharmacia). The column was equilibrated with 25 mM piperazin-HCl, pH 5.5, and the elution was performed with 10% PB74-HCl, pH 4.0 (Pharmacia). Fractions with similar band patterns were pooled and washed three times with PBS on a Centriprep concentrator (Amicon) with a 3 kDa cut off membrane to a final volume of 1-3 ml and separated on a Prepcell as described above.

N-Terminal Sequencing

Fractions containing CFP8A and CFP16 were blotted to PVDF membrane after Tricine SDS-PAGE (Ploug et al, 1989). The relevant bands were excised and subjected to N-terminal amino acid sequence analysis on a Procise 494 sequencer (Applied Biosystems). The fraction containing CFP25A was blotted to PVDF membrane after 2-DE PAGE (isoelectric focusing in the first dimension and Tricin SDS-PAGE in the second dimension). The relevant spot was excised and sequenced as described above.

The following N-terminal sequences were obtained:

```
CFP8A:
DPVDDAFIAKLNTAG         (SEQ ID NO: 155)

CFP16:
AKLSTDELLDAFKEM         (SEQ ID NO: 156)
```

N-Terminal Homology Searching in the Sanger Database and Identification of the Corresponding Genes.

The N-terminal amino acid sequence from each of the proteins was used for a homology search using the blast program of the Sanger *Mycobacterium tuberculosis* database: http://www.sanger.ac.uk/projects/m-tuberculosis/TB-blast-server.

For CFP8A and CFP16 the following information was obtained:

CFP8A: A sequence 80% identical to the 15 N-terminal amino acids was found on contig TB_1884. The N-terminally determined sequence from the protein purified from culture filtrate starts at amino acid 32. This gives a length of the mature protein of 98 amino acids corresponding to a theoretical MW of 9700 Da and a pI of 3.72 This is in good agreement with the observed MW on SDS-PAGE at approximately 8 kDa. The full length protein has a theoretical MW of 12989 Da and a pI of 4.38.

CFP16: The 15 aa N-terminal sequence was found to be 100% identical to a sequence found on cosmid MTCY20H1.

The identity is found within an open reading frame of 130 amino acids length corresponding to a theoretical MW of CFP16 of 13440.4 Da and a pI of 4.59. The observed molecular weight in an SDS-PAGE gel is 16 kDa.

Use of Homology Searching in the EMBL Database for Identification of CFP23.

Homology searching in the EMBL database (using the GCG package of the Biobase, Århus-DK) with the amino acid sequences of two earlier identified highly immunoreactive ST-CF proteins, using the TFASTA algorithm, revealed that these proteins (CFP21 and CFP25) belong to a family of fungal cutinase homologs. Among the most homologous sequences were also two *Mycobacterium tuberculosis* sequences found on cosmid MTCY13E12. The first, MTCY13E12.04 has 46% and 50% identity to CFP25 and CFP21 respectively. The second, MTCY13E12.05, has also 46% and 50% identity to CFP25 and CFP21. The two proteins share 62.5% aa identity in a 184 residues overlap. On the basis of the high homology to the strong T-cell antigens CFP21 and CFP25, respectively, it is believed that CFP19A and CFP23 are possible new T-cell antigens.

The first reading frame encodes a 254 amino acid protein of which the first 26 aa constitute a putative leader peptide that strongly indicates an extracellular location of the protein. The mature protein is thus 228 aa in length corresponding to a theoretical MW of 23149.0 Da and a Pi of 5.80. The protein is named CFP23.

The second reading frame encodes an 231 aa protein of which the first 44 aa constitute a putative leader peptide that strongly indicates an extracellular location of the protein. The mature protein is thus 187 aa in length corresponding to a theoretical MW of 19020.3 Da and a Pi of 7.03. The protein is named CFP19A.

The presence of putative leader peptides in both proteins (and thereby their presence in the ST-CF) is confirmed by theoretical sequence analysis using the signalP program at the Expasy molecular Biology server Searching for Homologies to CFP16 and CFP23 in the EMBL Database.

The amino acid sequences derived from the translated genes of the individual antigens were used for homology searching in the EMBL and Genbank databases using the TFASTA algorithm, in order to find homologous proteins and to address eventual functional roles of the antigens.

CFP16: RpIL gene, 130 aa. Identical to the *M. bovis* 50s ribosomal protein L7/L12 (acc. No P37381).

CFP23: CFP23 has between 38% and 46% identity to several cutinases from different fungal sp.

In addition CFP23 has 46% identity and 61% similarity to CFP25 as well as 50% identity and 63% similarity to CFP21 (both proteins are earlier isolated from the ST-CF).

Cloning of the Genes Encoding CFP8A, CFP16 and CFP23

The genes encoding CFP8A, CFP16 and CFP23 were all cloned into the expression vector pMCT6, by PCR amplification with gene specific primers, for recombinant expression in *E. coli* of the proteins.

PCR reactions contained 10 ng of *M. tuberculosis* chromosomal DNA in 1× low salt Taq+ buffer from Stratagene supplemented with 250 mM of each of the four nucleotides (Boehringer Mannheim), 0.5 mg/ml BSA (IgG technology), 1% DMSO (Merck), 5 pmoles of each primer and 0.5 unit Taq+ DNA polymerase (Stratagene) in 10 ml reaction volume. Reactions were initially heated to 94° C. for 25 sec. and run for 30 cycles of the program; 94° C. for 10 sec., 55° C. for 10 sec. and 72° C. for 90 sec, using thermocycler equipment from Idaho Technology.

The DNA fragments were subsequently run on 1% agarose gels, the bands were excised and purified by Spin-X spin columns (Costar) and cloned into pBluescript SK II+-T vector (Stratagene). Plasmid DNA was hereafter prepared from clones harbouring the desired fragments, digested with suitable restriction enzymes and subcloned into the expression vector pMCT6 in frame with 8 histidines which are added to the N-terminal of the expressed proteins. The resulting clones were hereafter sequenced by use of the dideoxy chain termination method adapted for supercoiled DNA using the Sequenase DNA sequencing kit version 1.0 (United States Biochemical Corp., USA) and by cycle sequencing using the Dye Terminator system in combination with an automated gel reader (model 373A; Applied Biosystems) according to the instructions provided. Both strands of the DNA were sequenced.

For cloning of the individual antigens, the following gene specific primers were used:

```
CFP8A: Primers used for cloning of cfp8A:
CFP8A-F:
                              (SEQ ID NO: 157)
CTGAGATCTATGAACCTACGGCGCC CFP8A-R:
                              (SEQ ID NO: 158)
CTCCCATGGTACCCTAGGACCCGGGCAGCCCCGGC
```

CFP8A-F and CFP8A-R create BglII and NcoI sites, respectively, used for the cloning in pMCT6.

```
CFP16: Primers used for cloning of cfp16:
OPBR-104:
CCGGGAGATCTATGGCAAAGCTCTCCACCGACG    (SEQ ID NO: 159)

OPBR-105:
CGCTGGGCAGAGCTACTTGACGGTGACGGTGG    (SEQ ID NO: 160)
```

OPBR-104 and OPBR-105 create BglII and NcoI sites, respectively, used for the cloning in pMCT6.

CFP23: Primers used for cloning of cfp23:
OPBR-86:
CCTTGGGAGATCTTTGGACCCCGGTTGC    (SEQ ID NO: 161)

OPBR-87:
GACGAGATCTTATGGGCTTACTGAC    (SEQ ID NO: 162)

OPBR-86 and OPBR-87 both create a BglII site used for the cloning in pMCT6.

Expression/Purification of Recombinant CFP8A, CFP16 and CFP23 Proteins.

Expression and metal affinity purification of recombinant proteins was undertaken essentially as described by the manufacturers. For each protein, 1 l LB-media containing 100 µg/ml ampicillin, was inoculated with 10 ml of an overnight culture of XL1-Blue cells harbouring recombinant pMCT6 plasmids. Cultures were shaken at 37° C. until they reached a density of $OD_{600}$=0.4-0.6. IPTG was hereafter added to a final concentration of 1 mM and the cultures were further incubated 4-16 hours. Cells were harvested, resuspended in 1× sonication buffer+8 M urea and sonicated 5×30 sec. with 30 sec. pausing between the pulses.

After centrifugation, the lysate was applied to a column containing 25 ml of resuspended Talon resin (Clontech, Palo Alto, USA). The column was washed and eluted as described by the manufacturers.

After elution, all fractions (1.5 ml each) were subjected to analysis by SDS-PAGE using the Mighty Small (Hoefer Scientific Instruments, USA) system and the protein concentrations were estimated at 280 nm. Fractions containing recombinant protein were pooled and dialysed against 3 M urea in 10 mM Tris-HCl, pH 8.5. The dialysed protein was further purified by FPLC (Pharmacia, Sweden) using a 6 ml Resource-Q column, eluted with a linear 0-1 M gradient of NaCl. Fractions were analyzed by SDS-PAGE and protein concentrations were estimated at $OD_{280}$. Fractions containing protein were pooled and dialysed against 25 mM Hepes buffer, pH 8.5.

Finally the protein concentration and the LPS content were determined by the BCA (Pierce, Holland) and LAL (Endosafe, Charleston, USA) tests, respectively.

Example 2

Species Distribution of cfp21, cfp23 and rd1-orf3

Presence of cfp21, cfp23 and rd1-orf3 in Different Mycobacterial Species.

The Southern blotting was carried out as described previously (Oettinger and Andersen, 1994) with the following modifications: 2 µg of genomic DNA was digested with PvuII, electrophoresed in an 0.8% agarose gel, and transferred onto a nylon membrane (Hybond N-plus; Amersham International plc, Little Chalfont, United Kingdom) with a vacuum transfer device (Milliblot, TM-v; Millipore Corp., Bedford, Mass.).

The cfp21, cfp23 and rd1-orf3 gene fragments were amplified by PCR from the recombinant pMCT6 plasmids encoding the individual genes. The primers used (same as the primers used for cloning) are described in example 1a and 1b. The results are summarized in Table 3.

TABLE 3

Interspecies analysis of the cfp21 and rd1-orf3 genes by Southern blotting.

| Species and strain | cfp21 | cfp23 | rd1-orf3 |
|---|---|---|---|
| 1. *M. tub.* H37Rv | + | + | + |
| 2. *M. bovis* | + | + | + |
| 3. *M. bovis* BCG Danish 1331 | N.D. | + | − |
| 4. *M. bovis* BCG Japan | + | + | − |
| 5. *M. avium* | + | + | − |
| 6. *M. kansasii* | − | + | − |
| 7. *M. marinum* | + | + | − |
| 8. *M. scrofulaceum* | + | + | − |
| 9. *M. intercellulare* | + | + | − |
| 10. *M. fortuitum* | − | + | − |
| 11. *M. xenopi* | + | + | − |
| 12. *M. szulgai* | + | + | − |

+, positive reaction; −, no reaction, N.D. not determined.

Example 3

Total Extraction of Proteins from Dead *M. tuberculosis* Bacteria 1.5×10⁹ bacteria/ml *M. tuberculosis* was heat treated at 55° C. for 1.5 hours and checked for sterility. 10 ml of these heat killed bacteria was centrifuged at 2000 g for 40 min; the supernatant was discharged and the pellet resuspended in PBS containing 0.5% Tween 20 and used as the antigen source. The pellet was sonicated with 20 rounds of 90 seconds and centrifuged 30 min at 5000 g to remove unbroken cells. The supernatant containing soluble proteins as well as cell wall and cell membrane components was extracted twice with 10% SDS to release proteins inserted in the cell wall and membrane compartments. After a centrifugation at 20.000 g for 30 min the supernatant was precipitated with 8 volume of cold acetone and resuspended in PBS at a protein concentration of 5 mg/ml and named: Somatic Proteins Extract (SPE).

Example 3A

Subcellular Fractionation of *Mycobacterium tuberculosis*

1.5×10⁹ colony forming units (CFU/ml) of *M. tuberculosis* H37Rv were inactivated by heat-killing at 60° C. for 1.5 hour. The heat-killed *Mycobacteria* was centrifuged at 3,000×g for 20 min; the supernatant was discarded and the pellet was resuspended in cold PBS. This step was repeated twice. After the final wash, the pellet was resuspended in a homogenizing buffer consisting of PBS supplemented with 10 mM EDTA and 1 mM of phenylmethylsulfonyl fluoride in a ratio of 1 ml buffer per 0.5 g of heat-killed *Mycobacteria*. The sample was sonicated on ice for 15 min (1-min-pulser-on/10-sec-pulser off) and subsequently lysed three times with a French Pressure Cell at 12,000 lb/in². The lysate was centrifuged at 27,000×g for 20 min; the pellet was washed in homogenizing buffer and recentrifuged. The pooled supernatants contained a mixture of cytosol and membrane components, while the pellet represented the crude cell wall.

Preparation of Cell Wall

The cell wall pellet, resuspended in homogenizing buffer, was added RNase and DNase to a final concentration of 1 mg/ml and incubated overnight at 4° C. The cell wall was washed twice in homogenizing buffer, twice in homogenizing buffer saturated with KCl, and twice with PBS. Soluble proteins were extracted from the cell wall by a 2 hour incubation with 2% SDS at 6° C. The insoluble cell wall core was removed by a centrifugation at 27,000×g for 20 min and the SDS-extraction was repeated. Finally, the pooled supernatants were precipitated with 6 volumes of chilled acetone and resuspended in PBS.

Preparation of Cytosol and Membrane:

To separate the cytosol and the membrane fraction, the pooled supernatants were ultracentrifugated at 100,000×g for 2 hours at 5° C. The cytosol proteins in the supernatant were precipitated with acetone and resuspended in PBS. The pellet, representing the membrane fraction, was washed in PBS, ultracentrifugated, and finally resuspended in PBS.

Triton X-114 Extraction of Cell Wall and Membrane:

To prepare protein fractions largely devoid of lipoarabinomannan, the cell wall and the membrane fraction were subjected to extraction with precondensed Triton X-114. Triton X-114 was added to the protein sample at a final concentration of 4%. The solution was mixed on ice for 60 min and centrifuged at 20,000×g for 15 min at 4° C. The pellet containing residual insoluble material was extracted once more (membrane) or twice (cell wall), while the supernatant was warmed to 37° C. to condense the Triton X-114. After centrifugation of the supernatant at 12,000×g for 15 min, the aqueous phase and detergent phase were separated. The aqueous phase and detergent phase were washed twice with Triton X-114 and PBS, respectively. The combined aqueous phases and residual insoluble material containing the majority of proteins were pooled, precipitated with acetone, and resuspended in PBS.

Example 4A

Identification of Proteins from the Cytosolic Fraction

Use of Patient Sera to Identify *M. tuberculosis* Antigens

This example illustrates the identification of antigens from the cytosol fraction by screening with serum from *M. tuberculosis* infected individuals in western blot. The reaction with serum was used as an indication that the proteins are recognized immunologically.

Identification of Abundant Proteins

As immunity to tuberculosis is not B-cell but T-cell mediated, reactivity with serum from TB patients was not the only selection criterion used to identify proteins from the cytosol. Further proteins were selected by virtue of their abundance in the cytosol.

The cytosol was precipitated with ammonium sulphate at 80% saturation. The non-precipitated proteins were removed by centrifugation and precipitated proteins were resuspended in 20 mM imidazole, pH 7.0. The protein solution was applied to a DEAE Sepharose 6B column, equilibrated with 20 mM imidazole. Bound protein was eluted from the column using a salt gradient from 0 to 1 M NaCl, in 20 mM imidazole. Fractions collected during elution was analyzed on a silver stained 10-20% SDS-PAGE and on 2 dimensional electrophoresis. Fractions containing well separated bands were selected for 2D electrophoresis and blotted to PVDF, after which spots, visualised by staining with Coomassie Blue, were selected for N-terminal sequencing.

The following N-terminal sequence was obtained

```
For TB15A:
S A Y K T V V V G T D D X S X   (SEQ ID NO: 163)
```

No sequence identity was found, when searching the Sanger database using the blast program. However, when the blast program at Swiss-blast was used, a sequence was obtained.

TB15A

For the determined N-terminal sequence of TB15 a 78% identical sequence was found in CY01B2.28. The X at position 13 of the determined N-terminal sequence corresponds to a G in MTCY01B2.28 and the X at position 15 to a D.

Within the open reading frame the translated protein is 146 amino acids long. The N-terminal sequence of the protein identified in the cytosol starts at amino acid no 2, with the N-terminal Met cleaved off.

This gives a protein of 146 amino acids, which corresponds to a theoretical molecular mass of 15 313 Da and a theoretical pl of 5.60. The observed mass in SDS-PAGE is 16 kDa.

The highest sequence identity, 32% in a 34 amino acid overlap, was found to a conserved protein of *Methanobacterium thermoautotrophicum*.

Example 4B

Identification of Proteins from the Cell Wall

Identification of TB16 TB32 and TB51.

Proteins contained in the cell wall fraction were separated by 2-D electrophoresis. A sample containing 120 mg protein was subjected to isoelectric focusing in a pH gradient from 4 to 7. The second dimension separation (SDS-PAGE) was carried out in a 10-20% acrylamide gradient. After blotting onto a PVDF membrane, proteins could be visualised by Coomassie blue staining.

N-Terminal Sequencing.

The relevant spots were excised from the PVDF membrane and subjected to N-terminal sequencing using a Procise sequencer (Applied Biosystems). The following N-terminal sequences were obtained:

```
TB16:
ADKTTQTIYIDADPG      (SEQ ID NO: 164)

TB32:
SGNSSLGIIVGIDD       (SEQ ID NO: 165)

TB51:
MKSTVEQLSPTRVRI      (SEQ ID NO: 166)
```

N-Terminal Sequence Identity Searching and Identification of the Corresponding Genes.

The N-terminal amino acid sequence from each of the proteins identified was used for a sequence identity search using the tblastn program at NCBI.

The following information was obtained:

TB16:

The 15 aa N-terminal sequence was found to be 100% identical to a sequence found within the *Mycobacterium tuberculosis* sequence MTV021.

The identity is found within an open reading frame of 144 amino acids length corresponding to a theoretical molecular mass of 16294 Da and a pl of 4.64. The apparent molecular mass in an SDS-PAGE gel is 17 kDa.

The amino acid sequence shows some similarity to other hypothetical Mycobacterial proteins.

TB32:

The 14 aa N-terminal sequence was found to be 100% identical to a sequence found within the *Mycobacterium tuberculosis* sequence MTCY1A10.

The identity is found within an open reading frame of 297 amino acids length corresponding to a theoretical molecular mass of 31654 Da and a pI of 5.55. The apparent molecular mass in an SDS-PAGE gel is 33 kDa.

The amino acid sequence shows some similarity to other hypothetical Mycobacterial proteins.

TB51:

The 15 aa N-terminal sequence was found to be 100% identical to a sequence found within the *Mycobacterium tuberculosis* sequence MTV008.

The identity is found within an open reading frame of 466 amino acids length corresponding to a theoretical molecular mass of 50587 Da and a pI of 4.3. The apparent molecular mass in an SDS-PAGE gel is 56 kDa.

The amino acid sequence shows similarities to trigger factor from several organisms. Possible chaperone protein.

Example 4C

Cloning of the Genes Encoding TB15A, TB16, TB32 and TB51

The genes encoding TB15A, TB16, TB32 and TB51 were all cloned into the *E. coli* expression vector pMCT3, by PCR amplification with gene specific primers.

Each PCR reaction contained 10 ng of *M. tuberculosis* chromosomal DNA in 1× low salt Taq+ buffer (Stratagene) supplemented with 250 □M of each of the four nucleotides (Boehringer Mannheim), 0.5 mg/ml BSA (IgG technology), 1% DMSO (Merck), 5 pmoles of each primer, and 0.5 unit Taq+ DNA polymerase (Stratagene) in 10 □l reaction volume. Reactions were initially heated to 94° C. for 25 sec. and run for 30 cycles according to the following program; 94° C. for 10 sec., 55° C. for 10 sec., and 72° C. for 90 sec., using thermocycler equipment from Idaho Technology.

The PCR fragment was ligated with TA cloning vector pCR® 2.1 (Invitrogen) and transformed into *E. coli*. Plasmid DNA was thereafter prepared from clones harbouring the desired fragment, digested with suitable restriction enzymes and subcloned into the expression vector pMCT3 in frame with 6 histidine residues which are added to the N-terminal of the expressed proteins. The resulting clones were hereafter sequenced by cycle sequencing using the Dye Terminator system in combination with an automated gel reader (model 373A; Applied Biosystems) according to the instructions provided. Both strands of the DNA were sequenced.

Expression and metal affinity purification of recombinant proteins was undertaken essentially as described by the manufacturers. For each protein, 1 l LB-media containing 100 μg/ml ampicillin, was inoculated with 10 ml of an overnight culture of XL1-Blue cells harbouring recombinant pMCT3 plasmids. Cultures were shaken at 37° C. until they reached a density of $OD_{600}$=0.4-0.6. IPTG was hereafter added to a final concentration of 1 mM and the cultures were further incubated 4-16 hours. Cells were harvested, resuspended in 1× sonication buffer+8 M urea and sonicated 5×30 sec. with 30 sec. pausing between the pulses.

After centrifugation, the lysate was applied to a column containing 10 ml of resuspended Talon resin (Clontec, Palo Alto, USA). The column was washed and eluted as described by the manufacturers.

After elution, all fractions (1.5 ml each) were subjected to analysis by SDS-PAGE using the Mighty Small (Hoefer Scientific Instruments, USA) system and the protein concentrations were estimated at $OD_{280\ nm}$. Fractions containing recombinant protein were pooled and dialysed against 3 M urea in 10 mM Tris-HCl, pH 8.5. The dialysed protein was further purified by FPLC (Pharmacia, Sweden) using 1 ml HiTrap columns (Pharmacia, Sweden) eluted with a linear salt gradient from 0-1 M NaCl. Fractions were analysed by SDS-PAGE and protein concentrations were estimated at $OD_{280\ nm}$. Fractions containing protein were pooled and dialysed against 25 mM Hepes buffer, pH 8.5.

Finally, the protein concentration and the LPS content were determined by the BCA (Pierce, Holland) and LAL (Endosafe, Charleston, USA) tests, respectively.

For cloning of the individual proteins, the following gene specific primers were used:

```
TB15A: Primers used for cloning of TB15A:
TB15A-F:
                                    (SEQ ID NO: 167)
CTG CCA TGG CTA GGT GGT GTG CAC GAT C TB15A-R:
                                    (SEQ ID NO: 168)
CTG AAG CTT ATG AGC GCC TAT AAG ACC
```

TB15-F and TB15-R create NcoI and HindIII sites, respectively, used for the cloning in pMCT3.

```
TB16: Primers used for cloning OF TB16:
TB16-F:
                                    (SEQ ID NO: 169)
CTG AGA TCT GCG GAC AAG ACG ACA CAG TB16-R:
                                    (SEQ ID NO: 170)
CTC CCA TGG TAC CGG AAT CAC TCA GCC
```

TB16-F and TB16-R create BG/II and NcoI sites, respectively, used for the cloning in pMCT3.

```
TB32: Primers used for cloning of TB32:
TB32-F:
                                    (SEQ ID NO: 171)
CTG AGA TCT ATG TCA TCG GGC AAT TCA TB32-R:
                                    (SEQ ID NO: 172)
CTC CCA TGG CTAC CTA AGT CAG CGA CTC GCG
```

TB32-F and TB32-R create BG/II and NcoI sites, respectively, used for the cloning in pMCT3.

```
TB51: Primers used for cloning of TB51:
TB51-F:
                                    (SEQ ID NO: 173)
CTG AGA TCT GTG AAG AGC ACC GTC GAG TB51-R:
                                    (SEQ ID NO: 174)
CTC CCA TGG GTC ATA CGG TCA CGT TGT
```

TB51-F and TB51-R create BG/II and NcoI sites, respectively, used for the cloning in pMCT3.

Example 5

Evaluation of Immunological Activity of Identified Somatic Proteins

The Use of Polypeptides as Diagnostic Reagents:

A polypeptide has diagnostic potential in humans when it is inducing significantly higher responses in patients with microscopy or culture positive tuberculosis compared to PPD positive or PPD negative individuals with no known history of TB infection or exposure to *M. tuberculosis* but who may or may not have received a prior BCG vaccination, have been exposed to non-tuberculosis mycobacteria (NTM), or be actively infected with *M. avium*. To identify polypeptides capable of discriminating between the above mentioned groups, the level of response and the frequency of positive responders to the polypeptide is compared. By positive responders are meant i) reactivity by human serum or plasma from TB patients with the polypeptide using conventional antibody ELISA/Western blot or ii) in vivo delayed type hypersensitivity response to the polypeptide which is at least 5 mm higher than the response induced by a control material.

The diagnostic potential of polypeptides will initially be evaluated in 10 individuals with TB infection and 10 individuals with no known exposure to virulent *Mycobacteria*. High specificity, >80% will be the most important selection criteria for these polypeptides and a sensitivity >80% is desirable but sensitivity >30% is acceptable as combinations of several specific antigens may be preferred in a cocktail of diagnostic reagent recognized by different individuals.

Skin Test Reaction in TB Infected Guinea Pigs

To identify polypeptides as antigens with the potential as TB diagnostic reagents the ability of the proteins to induce a skin test response will be evaluated in the guinea pig model where groups of guinea pigs have been infected with either *M. tuberculosis* or *M. avium* or vaccinated with BCG.

To evaluate the response in *M. tuberculosis* infected guinea pigs, female outbred guinea pigs will be infected via an ear vein with $1\times10^4$ CFU of *M. tuberculosis* H37Rv in 0.2 ml of PBS or aerosol infected (in an exposure chamber of a Middlebrook Aerosol Generation device) with $1\times10^5$ CFU/ml of *M. tuberculosis* Erdman given rise to 10-15 granulomas per animal in the lung. After 4 weeks skin test will be performed with the polypeptides diluted in 0.1 ml of PBS and 24 hours after the injection reaction diameter is measured.

To evaluate the response in *M. avium* infected guinea pigs, female outbred guinea pigs will be infected intradermally with $2\times10^6$ CFU of a clinical isolate of *M. avium* (Atyp. 1443; Statens Serum Institut, Denmark). Skin test are performed 4 weeks after with the polypeptides diluted in 0.1 ml of PBS and 24 hours after the injection reaction diameter is measured.

To evaluate the response in BCG vaccinated guinea pigs, female outbred guinea pigs will be sensitized intradermally with $2\times10^6$ CFU of BCG (BCG Danish 1331; Statens Serum Institut). Skin test are performed 4 weeks after with the polypeptides diluted in 0.1 ml of PBS and 24 hours after the injection reaction diameter is measured.

If a polypeptide induces a significant reaction in animal infected with *M. tuberculosis* but not in BCG vaccinated guinea pigs this polypeptide may have a potential as a diagnostic reagent to differentiate between BCG vaccinated and *M. tuberculosis* infected individuals, which will hereafter be evaluated in the human population.

If a polypeptide induces a reaction in *M. tuberculosis* infected guinea pigs but not in guinea pigs infected with *M. avium*, this polypeptide may have a potential as a diagnostic reagent with respect to differentiate between an individual infected with *M. tuberculosis* and an individual infected with *Mycobacteria* not belonging to the tuberculosis complex. The polypeptide may also have a potential as a diagnostic reagent to differentiate between a *M. avium* and a *M. tuberculosis* infected individual.

Example 6A

Serological Recognition of the Recombinant Produced Proteins

To test the potential of the proteins as serological antigens sera was collected from 8 TB patients and 4 healthy BCG non-vaccinated controls and were assayed for antibodies recognizing the recombinantly produced proteins in an ELISA assay as follows: Each of the sera was absorbed with Promega *E. coli* extract (S37761) for 4 hours at room temperature and the supernatants collected after centrifugation. 0.5 ug of the proteins in Carbonatbuffer at pH 9.6 were absorbed over night at 5° C. to a polystyrene plate (Maxisorp, Nunc). The plates were washed in PBS-0.05% Tween-20 and the sera applied in a dilution of 1:100. After 1 hour of incubation the plates were washed 3 times with PBS-0.05% Tween-20 and 100 ul per well of peroxidase-conjugated Rabbit Anti-Human IgA, IgG, IgM was applied in a dilution of 1:8000. After 1 hour of incubation the plates were washed 3 times with PBS-0.05% Tween-20. 100 ul of substrate (TMB PLUS, Kem-En-Tec) was added per well and the reaction stopped after 30 min with 0.2 M Sulphuric acid and the absorbance was read at 405 nm. The results are shown in table 4.

TABLE 4

Serological recognition of the proteins by TB patients (n = 8) and healthy controls (n = 4). The percentage of responders as well as the number of persons responding in each group is indicated. The cut-off values for positive responses are OD 0.2 for CFP8A, CFP16, CFP23 and RD1-ORF3, OD 0.25 for CFP21, TB15A and TB16 and OD 0.3 for TB51.

| Protein | Percent (n) responders | Percent (n) positive healthy controls |
|---|---|---|
| CFP8A | 63 (5) | 0 (0) |
| CFP16 | 50 (4) | 0 (0) |
| CFP21 | 80 (6) | 0 (0) |
| CFP23 | 50 (4) | 0 (0) |
| RD1-ORF3 | 25 (2) | 0 (0) |
| TB15A | 25 (2) | 0 (0) |
| TB16 | 100 (8) | 0 (0) |
| TB51 | 13 (1) | 0 (0) |

As shown in table 4 all the proteins are recognized by at least 13% of the tested TB patients. CFP8A, CFP16 and CFP21 are recognized by 50% or more of the TB patients tested and most extraordinary all the tested TB patients recognized TB16. In addition, CFP8A, CFP16, CFP21, CFP23, RD1-ORF3, TB15A, TB16 and TB51 were recognized with a very high OD (>0.5) by some of the TB patients indicating a particular high amount of specific antibodies to these proteins. None of the proteins are recognized by healthy non-BCG vaccinated controls, which demonstrates the potential of these proteins to differentiate between *M. tuberculosis* infected individuals and healthy individuals. All these proteins are therefore excellent diagnostic candidates.

Example 6B

Serological Recognition of Single Recombinant Produced Proteins and Mixtures of the Recombinant Produced Proteins To evaluate the potential of 39 recombinantly produced proteins as serological antigens were sera collected from 42 TB patients and 32 healthy controls and assayed for antibodies recognizing the recombinantly produced proteins in an ELISA assay as follows: Each of the sera was absorbed with Promega *E. coli* extract (S3761) for 4 hours at room temperature and the supernatants collected after centrifugation. 0.5 ug of the proteins in Carbonatbuffer at pH 9.6 were absorbed over night at 5° C. to a polystyrene plate (Maxisorp, Nunc). The plates were washed in PBS-0.05% Tween-20 and the sera applied in a dilution of 1:100. After 1 hour of incubation the plates were washed 3 times with PBS-0.05% Tween-20 and 100 ul per well of peroxidase-conjugated Rabbit Anti-Human IgA, IgG, IgM was applied in a dilution of 1:8000. After 1 hour of incubation the plates were washed 3 times with PBS-0.05% Tween-20. 100 ul of substrate (TMB PLUS, Kem-En-Tec) was added per well and the reaction stopped after 30 min with 0.2 M Sulphuric acid and the absorbance was read at 405 nm.

The results were evaluated for all the 39 tested proteins and on the basis of these results 7 antigens were selected for their superior abilities as serological antigens as shown in Table 5. For comparison has the result for the well known serological antigen 38 kDa also been shown in table 5.

TABLE 5

Serological recognition of the proteins by TB patients (n = 42) and healthy controls (n = 32). The number of responders as well as the calculated sensitivity and specificity is indicated for each antigen. Cut-off is defined as MeanControl + 3 SD for the individual antigen.

| Protein | TB patients | | Healthy controls | | Sensitivity | Specificity |
|---|---|---|---|---|---|---|
| | Positive | High responders* | Positive | High responders* | | |
| CFP8a | 11 | 2 | 1 | 0 | 26% | 96.9% |
| TB15A | 7 | 2 | 1 | 0 | 17% | 96.9% |
| CFP16 | 10 | 6 | 1 | 0 | 24% | 96.9% |
| TB16 | 23 | 9 | 0 | 0 | 55% | 100% |
| CFP21 | 13 | 3 | 1 | 0 | 31% | 96.9% |
| CFP23[a] | 12 | 3 | 1 | 0 | 23% | 97% |
| TB32 | 9 | 2 | 1 | 0 | 21% | 96.9% |
| TB51 | 14 | 5 | 0 | 0 | 33% | 100% |
| RD1-ORF3 | 6 | 5 | 0 | 0 | 14% | 100% |
| 38 kDa | 6 | 2 | 0 | 0 | 14% | 100% |

*High responders defined as OD values > MeanControl + 6 SDControl for each individual antigen.
[a]53 TB patients and 33 healthy controls were assayed for antibodies recognizing CFP23

For a diagnostic reagent for TB it is crucial to have a high specificity in order not to obtain false positive results which may lead to anti-TB treatment of healthy people. We therefore selected the serological antigens on the criteria of either the ability to induce a high specificity (more than 90%) combined with high sensitivity or the ability to enhance the sensitivity of a protein cocktail when combined with other antigens without compromising the high specificity. Also included in table 5 is the 38 kDa antigen which is well documented antigen and is believed to be one of the most promising serological proteins (Cole, R. A., et al 1996). As shown in table 5 the 38 kDa antigen has a sensitivity of 14% in the tested patient group and all the selected antigens shown in table 5 performs similar or with a higher sensitivity that the 38 kDa antigen without compromising the specificity (all selected antigen have a specificity more than 96%). In particular are TB16 and TB51 outstanding with a sensitivity of respectively 55% and 33% and a specificity of 100%. Also important is the fact that all these selected antigens induces a very high response in two or more donors which demonstrates their potency as diagnostic reagents.

For a diagnostic TB reagent it is important to achieve a very high sensitivity and as demonstrated in table 6 this be achieved by combining the antigens identified above. In practice this can be accomplished either by mixing the antigens in the same well in the ELISA plate or by combining the results from multiple wells incubated with the same blood sample. Alternatively the proteins of interests can be produced as recombinant fusions proteins comprising of at least two proteins or B cell epitopes and the resulting fusion molecule can hereafter can used in the serological assays.

The antibody response of tuberculosis is heterogeneous with considerable person-to-person variance to which antigens that are recognized by the antibodies (Lyashcenko, K. et al 1998) and therefore, can it be an advantage to use combinations of proteins (e.g. in protein cocktails) which may increase the sensitivity and be recognized by sera from a high proportion of infected individuals.

TABLE 6

Calculated sensitivity (sens.) and specificity (spec.) of selected antigen combinations

| # | Antigens | Sens. | Spec. |
|---|---|---|---|
| 2 | TB16 + TB51 | 62% | 100% |
| 2 | TB15A + TB16 | 64% | 97% |
| 2 | TB16 + CFP21 | 67% | 97% |
| 3 | TB15A + TB16 + TB51 | 71% | 97% |
| 3 | CFP16 + TB16 + CFP21 | 71% | 94% |
| 3 | TB16 + CFP21 + TB51 | 74% | 97% |
| 3 | TB15A + TB16 + CFP21 | 74% | 94% |
| 4 | CFP16 + CFP17 + CFP21 + TB51 | 64% | 94% |
| 4 | CFP8A + CFP16 + TB16 + CFP21 | 76% | 94% |
| 4 | CFP16 + TB16 + CFP21 + TB51 | 79% | 94% |

For the combinations shown in table 6 it is advantageous to combine from two to four antigens which will give a higher sensitivity than the single antigen and still a high specificity (more than 90%). In particular is the combination of CFP16+TB16+CFP21+TB51 and TB16+CFP21+TB51 and TB15A+TB16+CFP21 very efficient in this study population. The combinations shown in table 6 are only examples and other useful combinations can be envisaged as up to eight antigens may be combined and lead to increased sensitivity. In addition, can other antigens be combined with the above defined proteins for example the 38 kDa antigen which may be combined with any of the above described antigens and may increase the sensitivity. In this respect it is of importance that it has been observed that different populations react to different antigens (Julian, E. et al 2000, Lyashcenko, K. et al 1998) and it may therefore be necessary to define individual combinations for different populations. Therefore, combinations which does not give high sensitivity in the tested study population may be very efficient as diagnostic reagents when tested in another population.

LIST OF REFERENCES

Andersen et al. (1993) J. Immunol. Methods 161: 29-39.
Andersen P. et al., 1995, J. Immunol. 154: 3359-72
Andersen P., 1994, Infect. Immun. 62: 2536-44.
Andersen, P. and Heron, I, 1993, J. Immunol. Methods 161: 29-39.
Andersen, Å. B. et al., 1992, Infect. Immun. 60: 2317-2323.
Barkholt, V. and Jensen, A. L., 1989, Anal. Biochem. 177: 318-322.
Boesen et al (1995). Infection and Immunity 63:1491-1497
Borodovsky, M., and J. McIninch. 1993, Computers Chem. 17: 123-133.
Chang, C. D et al (1978) Nature, 375:515
Cole, R. A., et al 1996, Tuberc. Lung Dis. 77:363-368
Flesch, I. and S. H. E. Kaufmann (1987) J. Immunol. 138(12): 4408-13.
Goeddel et al., (1979) Nature 281:544

Gosselin et al., 1992, J. Immunol. 149: 3477-3481.
Harboe, M. et al., 1996, Infect. Immun. 64: 16-22.
Hochstrasser, D. F. et al., 1988, Anal. Biochem. 173: 424-435
Hopp and Woods (1981) Proc Natl Acad Sci USA. 78(6): 3824-8.
Itakura et al., (1977) Science 198:1056
Jameson and Wolf, (1988) Comput Appl Biosci, 4(1):181-6
Julian, E., et al 2000, Int J Tuberc Lung Dis 4(11):1082-1085.
Kyte and Doolittle, (1982) J Mol Biol, 157(1):105-32
Köhler, G. and Milstein, C., 1975, Nature 256: 495-497.
Li, H. et al., 1993, Infect. Immun. 61: 1730-1734.
Lindblad E. B. et al., 1997, Infect. Immun. 65: 623-629.
Lyashcenko, K., et al 1998, Infection and Immunity 66(8): 3936-3940.
Mahairas, G. G. et al., 1996, J. Bacteriol 178: 1274-1282.
Maniatis T. et al., 1989, "Molecular cloning: a laboratory manual", 2nd ed., Cold Spring Harbor Laboratory, Cold Spring Harbor, N.Y.
Nagai, S. et al., 1991, Infect. Immun. 59: 372-382.
Oettinger, T. and Andersen, Å. B., 1994, Infect. Immun. 62: 2058-2064.
Ohara, N. et al., 1995, Scand. J. immunol. 41: 233-442.
Pal P. G. and Horwitz M. A., 1992, Infect. Immun. 60: 4781-92.
Pearson, W. R. and Lipman D. J., 1988. Proc. Natl. Acad. Sci. USA 85: 2444-2448.
Ploug, M. et al., 1989, Anal. Biochem. 181: 33-39.
Porath, J. et al., 1985, FEBS Lett. 185: 306-310.
Roberts, A. D. et al., 1995, Immunol. 85: 502-508.
Rook, G. A. W. (1990) Res. Microbiol. 141:253-256.
Siebwenlist et al., (1980) Cell, 20: 269
Sørensen, A. L. et al., 1995, Infect. Immun. 63: 1710-1717.
Theisen, M. et al., 1995, Clinical and Diagnostic Laboratory Immunology, 2: 30-34.
Ulmer, J. B. et al., (1993) Curr. Opin. Invest. Drugs, 2:983-989
Valdés-Stauber, N. and Scherer, S., 1994, Appl. Environ. Microbiol. 60: 3809-3814.
Valdés-Stauber, N. and Scherer, S., 1996, Appl. Environ. Microbiol. 62: 1283-1286.
van Dyke M. W. et al., 1992. Gene pp. 99-104.
von Heijne, G., 1984, J. Mol. Biol. 173: 243-251.
Williams, N., 1996, Science 272: 27.
Young, R. A. et al., 1985, Proc. Natl. Acad. Sci. USA 82: 2583-2587.

The invention claimed is:

1. A nucleic acid fragment in isolated form which
   1) comprises a nucleic acid sequence which encodes a polypeptide which
      a) comprises an amino acid sequence as shown in SEQ ID NO: 2,
      b) comprises a subsequence of the amino acid sequence as shown in SEQ ID NO:2 which has a length of at least 6 amino acid residues, said subsequence being immunologically equivalent to the polypeptide defined in a) with respect to the ability of evoking a protective immune response against infections with mycobacteria belonging to the tuberculosis complex or with respect to the ability of eliciting a diagnostically significant immune response indicating previous or ongoing sensitization with antigens obtainable from mycobacteria belonging to the tuberculosis complex, or
      c) comprises an amino acid sequence having a sequence identity with the amino acid sequence defined in a) or the subsequence defined in b) of at least 70% and at the same time being immunologically equivalent to the amino acid sequence defined in a) with respect to the ability of evoking a protective immune response against infections with mycobacteria belonging to the tuberculosis complex or with respect to the ability of eliciting a diagnostically significant immune response indicating previous or ongoing sensitization with antigens obtainable from mycobacteria belonging to the tuberculosis complex; or comprises a nucleic acid sequence complementary thereto.

2. A nucleic acid fragment according to claim 1, wherein said polypeptide comprises an epitope for a T-helper cell.

3. A nucleic acid fragment according to claim 1, wherein the polypeptide is free from any signal sequence.

4. A nucleic acid fragment according to claim 1, wherein said polypeptide
1) induces a release of IFN-γ from primed memory T-lymphocytes withdrawn from a mouse within 2 weeks of primary infection or within 4 days after the mouse has been re-challenge infected with mycobacteria belonging to the tuberculosis complex, the induction performed by the addition of the polypeptide to a suspension comprising about 200.000 spleen cells per ml, the addition of the polypeptide resulting in a concentration of 1-4 µg polypeptide per ml suspension, the release of IFN-γ being assessable by determination of IFN-γ in supernatant harvested 2 days after the addition of the polypeptide to the suspension, and/or
2) induces a release of IFN-γ of at least 300 pg above background level from about 1000,000 human PBMC (peripheral blood mononuclear cells) per ml isolated from TB patients in the first phase of infection, or from healthy BCG vaccinated donors, or from healthy contacts to TB patients, the induction being performed by the addition of the polypeptide to a suspension comprising the about 1,000,000 PBMC per ml, the addition of the polypeptide resulting in a concentration of 1-4 µg polypeptide per ml suspension, the release of IFN-γ being assessable by determination of IFN-γ in supernatant harvested 2 days after the addition of the polypeptide to the suspension; and/or
3) induces an IFN-γ release from bovine PBMC obtained from animals previously sensitized with mycobacteria belonging to the tuberculosis complex, said release being at least two times the release observed from bovine PBMC obtained from animals not previously sensitized with mycobacteria belonging to the tuberculosis complex.

5. A nucleic acid fragment according to claim 1, wherein the sequence identity in c) is at least 80%, at least 85%, at least 90%, at least 92%, at least 94%, at least 96%, or at least 98%.

6. A nucleic acid fragment comprising a nucleic acid sequence which encodes a polypeptide according to claim 1, wherein said polypeptide is a fusion polypeptide comprising at least one amino acid sequence or subsequence as defined in claim 1 and at least one fusion partner.

7. A nucleic acid fragment comprising a nucleic acid sequence which encodes a polypeptide according to claim 6 wherein the fusion partner is selected from the group consisting of:
(a) a polypeptide fragment obtained from a virulent mycobacterium; and
(b) at least one immunogenic portion, of the polypeptides in (a).

8. A nucleic acid fragment according to claim 1, which is a DNA fragment.

9. A nucleic acid fragment according to claim 1, which has a length of at least 20, at least 25, at least 30, at least 35, at least 40, at least 45, at least 50, at least 55, at least 60, at least 65, at least 70 or at least 80 nucleotides.

10. A nucleic acid fragment according to claim 1, which is more than 70% identical with a nucleic acid fragment which has a nucleotide sequence as defined in SEQ ID NO: 1.

11. A vaccine comprising a nucleic acid fragment according to claim 1, the vaccine effecting in vivo expression of antigen by an animal, including a human being, to whom the vaccine has been administered, the amount of expressed antigen being effective to confer substantially increased resistance to infections with mycobacteria of the tuberculosis complex in an animal, including a human being.

12. A vaccine for immunizing an animal, including a human being, against tuberculosis caused by mycobacteria belonging to the tuberculosis complex, comprising as the effective component a non-pathogenic microorganism, wherein at least one copy of a DNA fragment comprising a DNA sequence encoding a polypeptide as defined in claim 1 has been incorporated into the genome of the microorganism in a manner allowing the microorganism to express and optionally secrete the polypeptide.

13. A vaccine according to claim 12, wherein the microorganism is a bacterium.

14. A vaccine according to claim 13, wherein the bacterium is selected from the group consisting of the genera *Mycobacterium, Salmonella, Pseudomonas* and *Escherichia*.

15. A vaccine according to claim 14, wherein the microorganism is Mycobacterium Bovis BCG.

16. A vaccine according to claim 15, wherein at least 2 copies of a DNA fragment comprising a DNA sequence encoding a polypeptide have been incorporated into the genome of the microorganism, wherein the polypeptide
a) comprises an amino acid sequence as shown in SEQ ID NO: 2,
b) comprises a subsequence of the amino acid sequence as shown in SEQ ID NO:2 which has a length of at least 6 amino acid residues, said subsequence being immunologically equivalent to the polypeptide defined in a) with respect to the ability of evoking a protective immune response against infections with mycobacteria belonging to the tuberculosis complex or with respect to the ability of eliciting a diagnostically significant immune response indicating previous or ongoing sensitization with antigens obtainable from mycobacteria belonging to the tuberculosis complex, or
c) comprises an amino acid sequence having a sequence identity with the amino acid sequence defined in a) or the subsequence defined in b) of at least 70% and at the same time being immunologically equivalent to the amino acid sequence defined in a) with respect to the ability of evoking a protective immune response against infections with mycobacteria belonging to the tuberculosis complex or with respect to the ability of eliciting a diagnostically significant immune response indicating previous or ongoing sensitization with antigens obtainable from mycobacteria belonging to the tuberculosis complex; or comprises a nucleic acid sequence complementary thereto.

17. A vaccine according to claim 16, wherein the number of copies is at least 5.

18. A replicable expression vector which comprises a nucleic acid fragment according claim 1.

19. A vector according to claim 18, which is an autonomously replicating vector.

20. A vector according to claim 19, which is selected from the group consisting of a virus, a bacteriophage, a plasmid, a cosmid and a microchromosome.

21. A vector according to claim 18, which is able to become integrated into the genome of the host cell.

22. A vector according to claim 18, which comprises a DNA segment encoding a reporter gene product useful for identification of heterologous gene products and/or a resistance gene such as an antibiotic resistance gene.

23. A transformed cell harboring at least one vector according to claim 18.

24. A transformed cell according to claim 23, which is a bacterium belonging to the tuberculosis complex, such as a *M. tuberculosis bovis* BCG cell.

25. A transformed cell according to claim 23, which expresses a polypeptide comprising:
   a) an amino acid sequence as shown in SEQ ID NO: 2,
   b) a subsequence of the amino acid sequence as shown in SEQ ID NO:2 which has a length of at least 6 amino acid residues, said subsequence being immunologically equivalent to the polypeptide defined in a) with respect to the ability of evoking a protective immune response against infections with mycobacteria belonging to the tuberculosis complex or with respect to the ability of eliciting a diagnostically significant immune response indicating previous or ongoing sensitization with antigens obtainable from mycobacteria belonging to the tuberculosis complex, or
   c) an amino acid sequence having a sequence identity with the amino acid sequence defined in a) or the subsequence defined in b) of at least 70% and at the same time being immunologically equivalent to the amino acid sequence defined in a) with respect to the ability of evoking a protective immune response against infections with mycobacteria belonging to the tuberculosis complex or with respect to the ability of eliciting a diagnostically significant immune response indicating previous or ongoing sensitization with antigens obtainable from mycobacteria belonging to the tuberculosis complex; or comprises a nucleic acid sequence complementary thereto.

26. A method for producing a polypeptide as defined in claim 1, comprising inserting a nucleic acid fragment according to claim 1 into a vector which is able to replicate in a host cell, introducing the resulting recombinant vector into the host cell, culturing the host cell in a culture medium under conditions sufficient to effect expression of the polypeptide, and recovering the polypeptide from the host cell or culture medium; or isolating the polypeptide from a short-term culture filtrate as defined in claim 1; or isolating the polypeptide from whole mycobacteria of the tuberculosis complex or from lysates or fractions thereof; or synthesizing the polypeptide by solid or liquid phase peptide synthesis.

27. A method for immunizing an animal, including a human being, against tuberculosis caused by mycobacteria belonging to the tuberculosis complex, comprising administering to the animal the vaccine according to claim 13.

28. A method according to claim 27, wherein the vaccine is administered by the parenteral (such as intravenous and intraarterially), intraperitoneal, intramuscular, subcutaneous, intradermal, oral, buccal, sublingual, nasal, rectal or transdermal route.

29. A composition for diagnosing tuberculosis in an animal, including a human being, comprising a nucleic acid fragment according to claim 1, optionally in combination with a means for detection.

30. A method for determining the presence of mycobacterial nucleic acids in a sample, comprising incubating the sample with a nucleic acid fragment according to claim 1, and detecting the presence of hybridized nucleic acids resulting from the incubation.

31. A method for effecting in vivo expression of an antigen by an animal comprising administering thereto the nucleic acid sequence according to claim 1, where in said expression confers resistance to infections with mycobacteria of the tuberculosis complex.

32. The fusion partner of claim 7, wherein said polypeptide fragment is selected from the group consisting of ESAT-6, MPB64, MPT64, TB10.4, CFP10, RD1-ORF5, RD1, ORF2, Rv1036, Ag85A, Ag85B, Ag85C, 19 KDa lipoprotein, MPT32, MPB59 and alpha-crystallin.

33. A nucleic acid fragment comprising a nucleic acid sequence which encodes a polypeptide according to claim 6 wherein the fusion partner is selected from the group consisting of:
   a) a polypeptide, which comprises an amino acid sequence as shown in SEQ ID NO: 2,
   b) a polypeptide, which comprises a subsequence of the amino acid sequence as shown in SEQ ID NO:2 which has a length of at least 6 amino acid residues, said subsequence being immunologically equivalent to the polypeptide defined in a) with respect to the ability of evoking a protective immune response against infections with mycobacteria belonging to the tuberculosis complex or with respect to the ability of eliciting a diagnostically significant immune response indicating previous or ongoing sensitization with antigens obtainable from mycobacteria belonging to the tuberculosis complex, or
   c) a polypeptide, which comprises an amino acid sequence having a sequence identity with the amino acid sequence defined in a) or the subsequence defined in b) of at least 70% and at the same time being immunologically equivalent to the amino acid sequence defined in a) with respect to the ability of evoking a protective immune response against infections with mycobacteria belonging to the tuberculosis complex or with respect to the ability of eliciting a diagnostically significant immune response indicating previous or ongoing sensitization with antigens obtainable from mycobacteria belonging to the tuberculosis complex; or comprises a nucleic acid sequence complementary thereto.

34. A vaccine according to claim 15, wherein the microorganism is *Mycobacterium bovis* BCG strain: Danish 1331.

35. A method for producing a polypeptide as defined in claim 1, comprising inserting a nucleic acid fragment according to claim 1 into a vector which is able to replicate in a host cell, introducing the resulting recombinant vector into the host cell, culturing the host cell in a culture medium under conditions sufficient to effect expression of the polypeptide, and recovering the polypeptide from the host cell or culture medium; or isolating the polypeptide from a short-term culture filtrate as defined in claim 1; or isolating the polypeptide from cell wall containing fractions of the tuberculosis complex.

36. A nucleic acid fragment according to claim 1, wherein the sequence identity in c) is 100%.

37. A nucleic acid fragment according to claim 7, wherein the immunogenic portion is a T-cell epitope.

* * * * *

UNITED STATES PATENT AND TRADEMARK OFFICE
CERTIFICATE OF CORRECTION

PATENT NO. : 8,076,469 B2
APPLICATION NO. : 11/934048
DATED : December 13, 2011
INVENTOR(S) : Peter Andersen et al.

It is certified that error appears in the above-identified patent and that said Letters Patent is hereby corrected as shown below:

On the cover page item [30]

The following priority applications should be listed as follows: --Continuation of application No. 11/196,018, filed on Aug. 2, 2005, now abandoned, which is a division of application No. 10/138,473, filed on May 2, 2002, now Pat. No. 6,982,085, which is a continuation-in-part of application No. 10/060,428, filed on Jan. 29, 2002, now abandoned, which is a continuation-in-part of application No. 09/415,884, filed on Oct. 8, 1999, now abandoned. Application No. 10/138,473, filed on May 2, 2002, now Pat. No. 6,982,085, is also a continuation-in-part of application No. 09/791,171, filed on Feb. 20, 2001, now abandoned, which is a division of application No. 09/050,739, filed on Mar. 30, 1998, now Pat. No. 6,641,814.

Provisional application No. 60/116,673, filed on Jan. 21, 1999, provisional application No. 60/070,488, filed Jan. 5, 1998, and provisional application No. 60/044,624, filed on Apr. 18, 1997.--

Signed and Sealed this
Eighteenth Day of September, 2012

David J. Kappos
*Director of the United States Patent and Trademark Office*